(12) United States Patent
Harlev et al.

(10) Patent No.: US 11,751,937 B2
(45) Date of Patent: Sep. 12, 2023

(54) ABLATION CATHETERS AND RELATED SYSTEMS AND METHODS

(71) Applicant: Affera, Inc., Watertown, MA (US)

(72) Inventors: Doron Harlev, Watertown, MA (US); Ian Matthew Collier, Watertown, MA (US)

(73) Assignee: AFFERA, INC., Watertown, MA (US)

( * ) Notice: Subject to any disclaimer, the term of this patent is extended or adjusted under 35 U.S.C. 154(b) by 203 days.

(21) Appl. No.: 16/633,133

(22) PCT Filed: Jul. 24, 2018

(86) PCT No.: PCT/US2018/043529
§ 371 (c)(1),
(2) Date: Jan. 22, 2020

(87) PCT Pub. No.: WO2019/023259
PCT Pub. Date: Jan. 31, 2019

(65) Prior Publication Data
US 2020/0229866 A1    Jul. 23, 2020

Related U.S. Application Data

(60) Provisional application No. 62/536,877, filed on Jul. 25, 2017.

(51) Int. Cl.
*A61B 18/14* (2006.01)
*A61B 18/00* (2006.01)

(52) U.S. Cl.
CPC .......... *A61B 18/1492* (2013.01); *A61B 2018/00029* (2013.01); *A61B 2018/00577* (2013.01);
(Continued)

(58) Field of Classification Search
CPC .. A61B 2018/00577; A61B 2018/1465; A61B 2018/00738; A61B 2018/00029;
(Continued)

(56) References Cited

U.S. PATENT DOCUMENTS 3,888,249 A    6/1975    Spencer et al.
5,250,034 A   10/1993    Appling et al.
(Continued)

FOREIGN PATENT DOCUMENTS

EP    2724683 A1    4/2014
EP    3178431 A1    6/2017
(Continued)

OTHER PUBLICATIONS

ISA, "PCT Application No. PCTUS18/43563, International Search Report and Written Opinion dated Oct. 17, 2018", 11 pages.
(Continued)

*Primary Examiner* — Khadijeh A Vahdat
*Assistant Examiner* — Marina Delaney Templeton
(74) *Attorney, Agent, or Firm* — TAROLLI, SUNDHEIM, COVELL & TUMMINO L.L.P.

(57) ABSTRACT

An ablation catheter having a deformable tip is disclosed herein. In some implementations, the ablation catheter includes a catheter body and a deformable tip secured to the catheter body. In these and other implementations, the catheter body can include a fluid delivery lumen. In these and other implementations, the deformable tip includes one or more valves that are configured to open in response to deformation of the deformable tip. In these and still other implementations, the ablation catheter is configured to permit liquid communication between an interior of the deformable tip and an exterior of the deformable tip. In some implementations, RF energy is transmitted from the interior of the deformable tip to the exterior of the deformable tip via liquid exiting the deformable tip.

22 Claims, 32 Drawing Sheets

(52) U.S. Cl.
CPC .............. *A61B 2018/00738* (2013.01); *A61B 2018/00815* (2013.01); *A61B 2018/00839* (2013.01); *A61B 2018/00875* (2013.01); *A61B 2018/1417* (2013.01); *A61B 2018/1465* (2013.01); *A61B 2018/1472* (2013.01); *A61B 2218/002* (2013.01)

(58) Field of Classification Search
CPC ...... A61B 18/1492; A61B 2018/00267; A61B 2018/1472; A61M 25/0074; A61M 25/0075; A61M 25/008; A61M 2025/0076; A61M 2025/0079; A61M 2025/0081
See application file for complete search history.

(56) References Cited

U.S. PATENT DOCUMENTS

| | | | |
|---|---|---|---|
| 5,797,903 | A | 8/1998 | Swanson et al. |
| 5,830,213 | A * | 11/1998 | Panescu ............. A61B 18/1492 606/41 |
| 7,163,533 | B2 | 1/2007 | Hobbs et al. |
| 9,125,668 | B2 | 9/2015 | Subramaniam et al. |
| 10,105,179 | B2 | 10/2018 | Harlev et al. |
| 2002/0156430 | A1* | 10/2002 | Haarala ............. A61M 25/0075 604/247 |
| 2004/0176743 | A1* | 9/2004 | Morris ............. A61M 25/0075 604/537 |
| 2008/0086073 | A1 | 4/2008 | McDaniel |
| 2009/0076498 | A1* | 3/2009 | Saadat ............. A61B 18/1492 606/41 |
| 2010/0016848 | A1 | 1/2010 | Desai |
| 2010/0204560 | A1* | 8/2010 | Salaheih ............ A61B 18/1492 600/373 |
| 2010/0256629 | A1* | 10/2010 | Wylie ............. A61B 18/1492 606/41 |
| 2011/0190751 | A1 | 8/2011 | Ingle et al. |
| 2013/0085493 | A1* | 4/2013 | Bloom .............. A61B 18/1492 606/41 |
| 2013/0138077 | A1* | 5/2013 | O'Day ............. B26F 1/0015 604/500 |
| 2013/0158536 | A1* | 6/2013 | Bloom .............. A61B 18/1492 606/41 |
| 2013/0211379 | A1 | 8/2013 | Clair et al. |
| 2014/0012209 | A1* | 1/2014 | Sansoucy ......... A61M 25/0075 604/247 |
| 2014/0081111 | A1 | 3/2014 | Zaya et al. |
| 2014/0364848 | A1* | 12/2014 | Heimbecher ...... A61B 18/1206 606/41 |
| 2015/0105764 | A1 | 4/2015 | Rizq et al. |
| 2015/0196740 | A1 | 7/2015 | Mallin et al. |
| 2015/0216580 | A1 | 8/2015 | Mihalik |
| 2015/0351652 | A1* | 12/2015 | Marecki ............. A61B 18/1492 600/374 |
| 2016/0051321 | A1 | 2/2016 | Amr et al. |
| 2017/0035498 | A1 | 2/2017 | Boden et al. |
| 2017/0042614 | A1 | 2/2017 | Salahieh et al. |
| 2017/0119454 | A1* | 5/2017 | Rioux ............... A61B 18/1482 |
| 2017/0143201 | A1 | 5/2017 | Claude et al. |
| 2017/0354463 | A1 | 12/2017 | Mori |
| 2018/0280080 | A1 | 10/2018 | Govari et al. |

FOREIGN PATENT DOCUMENTS

| | | |
|---|---|---|
| EP | 3238646 A2 | 11/2017 |
| WO | 2019023259 A1 | 1/2019 |
| WO | 2019023280 A1 | 1/2019 |

OTHER PUBLICATIONS

ISA, "PCT Application No. PCTUS18/43529, International Search Report and Written Opinion dated Mar. 15, 2019", 17 pages.
Simmons et al., "Comparison of Gold Versus Platinum Electrodes on Myocardial Lesion Size Using Radiofrequency Energy," 1996, 6 pages.

* cited by examiner

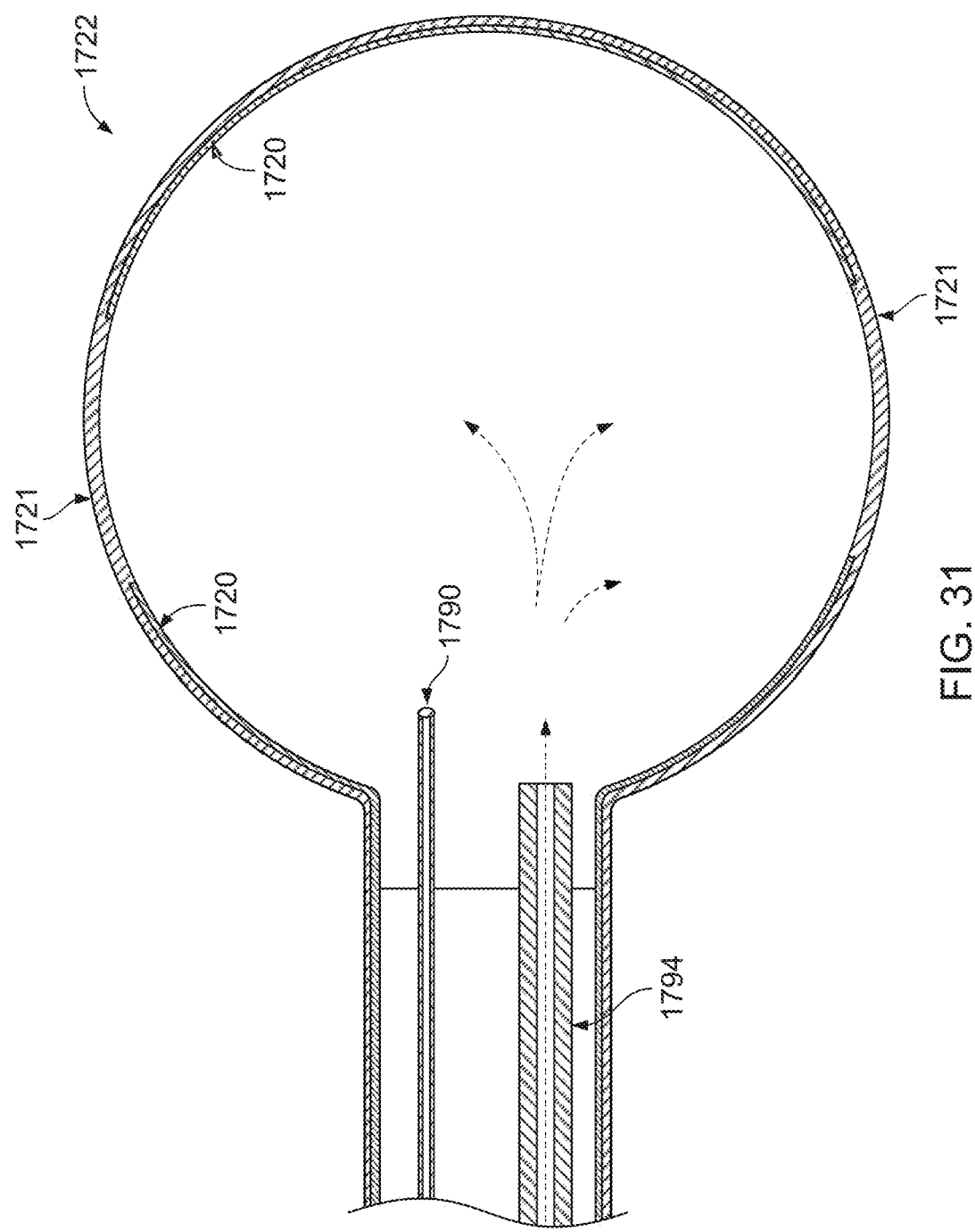

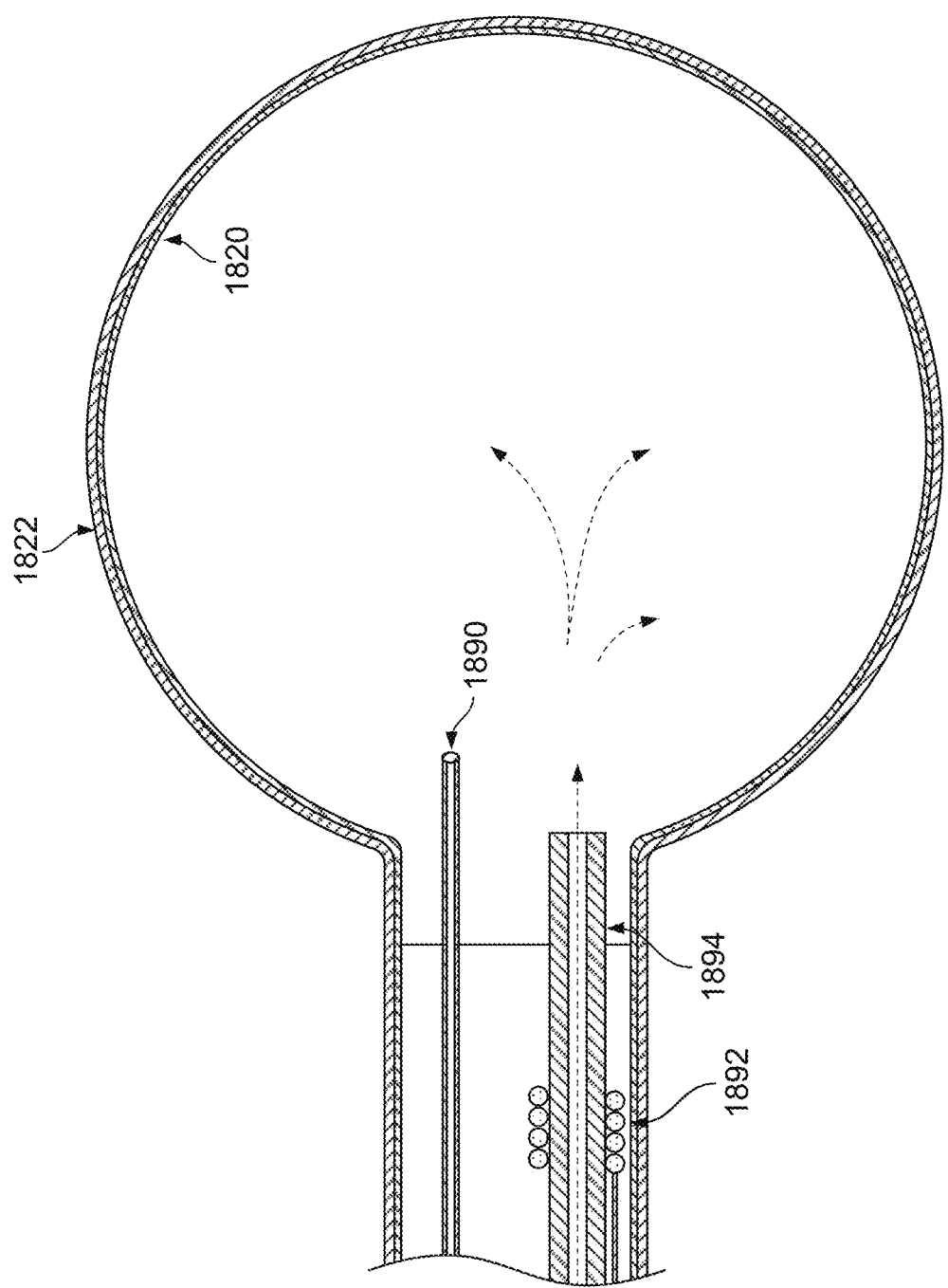

ABLATION CATHETERS AND RELATED SYSTEMS AND METHODS

CROSS REFERENCE TO RELATED APPLICATIONS

The present application is a 35 U.S.C. § 371 U.S. National Phase application of International Application No. PCT/US2018/043529, filed Jul. 24, 2018, which claims the benefit of U.S. Provisional Patent Application No. 62/536,877, filed Jul. 25, 2017, which are incorporated herein by reference in their entireties.

TECHNICAL FIELD

The present technology is generally related to ablation catheters and related systems and methods.

BACKGROUND

Abnormal rhythms, generally referred to as arrhythmia, can occur in the heart. Cardiac arrhythmias develop when abnormal conduction in the myocardial tissue modify the typical heartbeat pattern. Radio frequency ("RF") catheter ablation can be used to form lesions that interrupt the mechanism of abnormal conduction to terminate certain arrhythmias.

DESCRIPTION OF DRAWINGS

The disclosure will be understood more fully from the detailed description given below and from the accompanying drawings of various implementations of the disclosure. The drawings, however, should not be taken to limit the disclosure to the specific implementations, but are for explanation and understanding only.

FIG. 31 is a cross-sectional view of the distal end region of an ablation catheter having a conformable tip with two discrete regions including ablation electrode in the form of a conductive layer applied to its inner surface.

FIG. 32 is a cross-sectional view of the distal end region of an ablation catheter that includes a heating element around an irrigation lumen extending through a shaft of the catheter.

DETAILED DESCRIPTION

A. Overview

Figure 1:
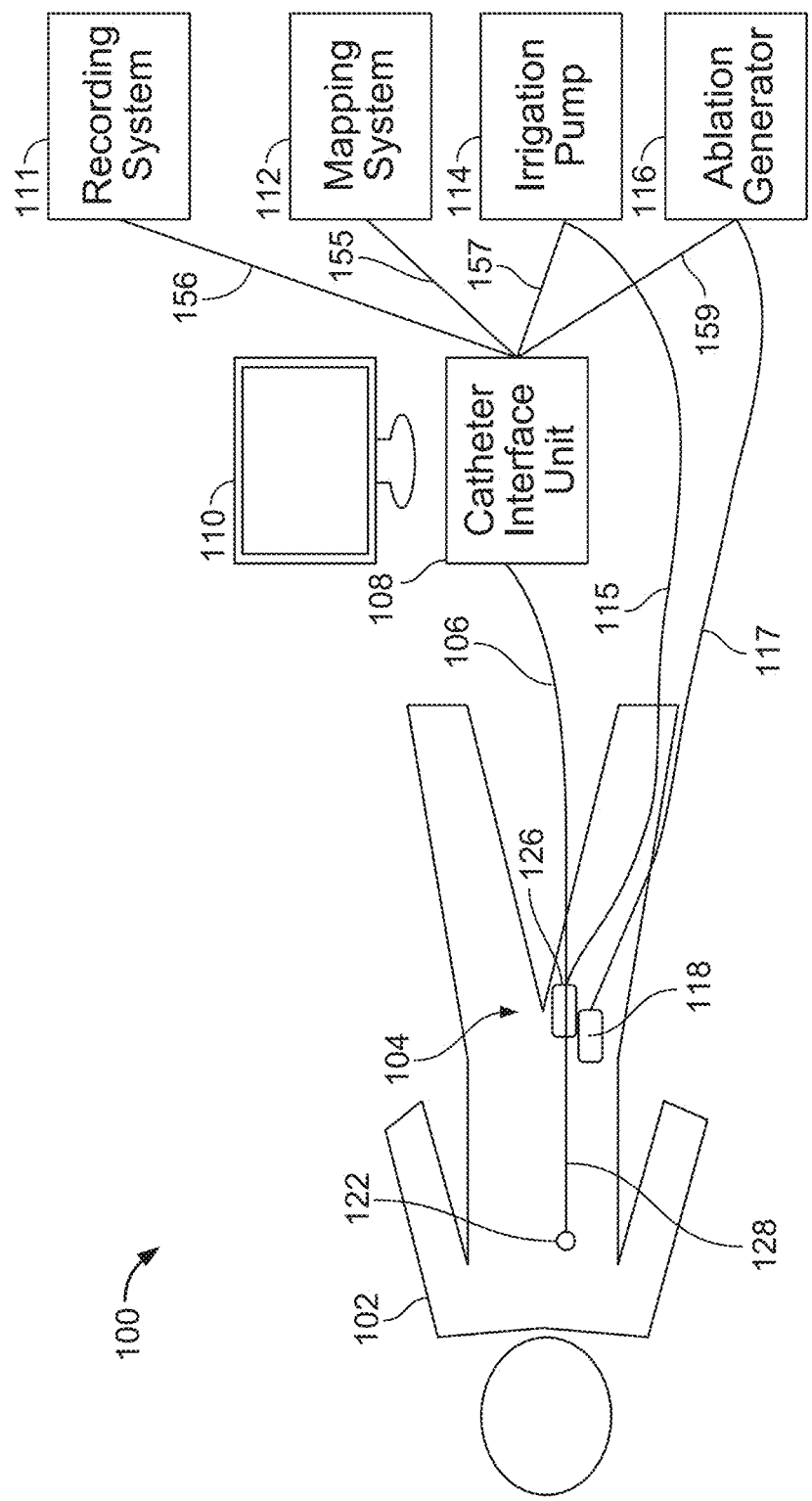
FIG. 1 schematically illustrates an ablation system configured in accordance with an implementation of the present technology during an ablation treatment.

The present disclosure is generally directed to devices, systems, and methods of delivering ablation energy to an anatomic structure of a patient in any one or more of various different medical procedures in which ablation energy is delivered to tissue at a treatment site within a patient. For the sake of clarity of explanation, the devices, systems, and methods of the present disclosure are described in the context of cardiac ablation procedures. However, unless otherwise specified or made clear from the context, the devices, systems, and methods of the present technology can be utilized in additional medical procedures including, but not limited to, ablating tumors in cancer treatment and electro-surgery procedures in which tissue is cut and substantially simultaneously cauterized to avoid or minimize bleeding.

Many of the ablation catheters described herein can be used to form larger lesions than most conventional ablation catheters. The size of non-collapsible ablation catheter tips, which are utilized by most conventional ablation catheters, is limited by the size of the sheath through which the ablation catheter is passed to introduce the ablation catheter into the patient's vasculature. Lesions that can be formed by such ablation catheters are, in turn, limited by the approximate surface area of the tip that comes into contact with targeted tissue and the amount of energy that can be safely delivered from the relatively small tip. In contrast with such conventional ablation catheters, the tips of many of the ablation catheters described herein are collapsible and expandable and can thus be delivered in a collapsed state through a sheath and then expanded to a larger size after delivery into the patient. Because these tips are capable of expanding to sizes (e.g., diameters) larger than the sheaths through which they are delivered and by conforming their shape to tissue to further increase the tip tissue surface area, a greater surface area of the tip, as compared to tips of many conventional ablation catheters, can be placed in contact with tissue of the patient, allowing a greater amount of energy to be delivered to the tissue. This can enable the formation of lesions having increased widths (e.g., diameters) and, in many cases, increased depths.

In certain implementations, the tip is conformable to the tissue being treated. This is expected to help ensure that a large surface area of the tip contacts the tissue even when the tissue being treated is not flat or smooth. Lesion characteristics are difficult to control using many conventional ablation catheters. One reason for this is that many conventional ablation catheter tips tend to be small and rigid. Depending on the surface topography of the tissue to be treated and the relative orientation between the catheter tip and tissue, it can be difficult to obtain a consistent amount of surface area interfacing with tissue. In some cases, the topography of the tissue can, for example, cause only a small area of the tip to contact the tissue (e.g., by causing only an edge region of the tip to contact the tissue.) The conformability of many of the catheter tips described herein can help to avoid outcomes like this. Thus, these catheter tips tend to provide larger and/or more consistently sized lesions.

In many implementations, the catheter tip includes shape-activated valves that allow liquid (e.g., saline) within the catheter tip to flow out of the catheter tip toward tissue in contact with the catheter tip while limiting the amount of liquid (e.g., saline) that flows out of regions of the tip that are not in contact with the tissue. This design can help to ensure that most of the energy being delivered by the ablation catheter is used to ablate the tissue intended to be ablated. In addition, treatments can be carried out more efficiently with such a design. For example, because most of the energy is being directed to the tissue being treated, many of the catheters described herein can create lesions that are larger than lesions created by most conventional ablation catheters while using the same amount of energy or even less energy than those conventional catheters.

The catheter tip, in many implementations, is able to selectively irrigate areas that come into contact with tissue, while providing substantially less irrigation in areas that do not. This is expected to ensure that sufficient irrigation is available in the area engaging tissue in order to avoid overheating and clot formation at the tip-tissue interface. Many existing devices have a uniform irrigation hole pattern. As a result, areas of the tip electrode that come into contact with tissue impede fluid flow and receive less irrigation, which can lead to excessive heating, blood coagulation and steam pop in certain circumstances.

In many cases, shape activated valves are distributed throughout the catheter tip in a manner to allow liquid to escape the catheter tip in any of multiple different directions around the tip. The liquid can, for example, be emitted from the distal end of the catheter tip when the distal end is brought into contact with tissue, and can be emitted from a side region of the catheter tip when the side region is brought into contact with tissue. Excluding the region occupied by the shaft body, the liquid can be emitted from the proximal end of the tip when the proximal end of the tip adjacent to the shaft body is brought into contact with tissue. This permits energy to be selectively delivered to tissue contacting the catheter tip regardless of the relative orientation between the catheter tip and tissue. Moreover, in many cases, the energy can be delivered via these different tip regions with about the same tissue-tip contact geometry such that lesions of about the same size and shape can be formed in tissue adjacent the distal end of catheter tip, adjacent the proximal region of the catheter tip, or somewhere in between. This versatility of the catheter tip is expected to allow a single ablation catheter to achieve highly consistent lesions regardless of the catheter body or tip orientation required to access the target region of tissue. Lesion consistency is also expected to be improved with a conformal tip because much of the tissue surface where the lesion is applied is covered with the tip and irrigation flow is predictable. In contrast, with conventional ablation catheters, lesion size is affected by blood flow that convectively cools the tissue surface. Because blood flow varies greatly between different areas of the heart, this contact and/or cooling leads to variability in lesion size. Lesion consistency can also be improved because the conformal tip conforms to tissue surface, providing a larger area for engagement. As such, it is likely that relative motion between the tip and tissue will be reduced. In contrast, with a conventional catheter, the catheter can become dislodged altogether and/or move in response to a heartbeat and/or respiration, and catheter movement can cause variability in lesion size.

In some implementations, the surface area of the catheter tip that contacts the tissue during treatment is larger than the surface area of many conventional ablation catheter tips, and/or the catheter tip is softer than such conventional catheters. This design can allow a greater force to be applied to the tissue by the catheter tip without damaging (e.g., perforating) the tissue because the force is distributed over a greater area leading to a more uniform and lower maximum pressure.

The configuration of the sensors in many of the ablation catheters described herein allows for improved feedback related to certain characteristics of the lesion being formed by the ablation catheter. The temperature sensors (e.g., thermistors) of many of the ablation catheters described herein, for example, are thermally insulated from the ablation electrode (e.g., conductive ink) that generates the energy to be delivered to the tissue for ablation. In many cases, the ablation electrode is located along an inner surface of the tip material, and the temperature sensor is located along an outer surface of the tip material or is embedded within the tip material. As a result, the thermally insulating material of the tip inhibits the temperature sensor from detecting heat conduction to or from the inside of the ablation electrode. In addition, the catheter tip can conform to the tissue in many implementations, which can help to ensure that the temperature sensor, or a thermally conductive material to which the temperature sensor is attached, directly contacts the tissue being ablated. This can further help to improve the accuracy with which the temperature sensor can detect the temperature of the tissue being ablated. As a result of this design, many of the ablation catheters described herein can achieve more accurate tissue temperature measurements than conventional ablation catheters that include a single temperature sensor coupled to a rigid, sometimes actively cooled, ablation tip. In those conventional ablation catheters, the temperature sensor tends to detect the temperature of the ablation tip (as opposed to that of the tissue alone).

Many of the ablation catheters described herein include sensing electrodes that can provide improved electrograms and lesion progress feedback as compared to certain conventional ablation catheters. The sensing electrodes of ablation catheters described herein, for example, can be positioned on the outer surface of an ablation catheter tip that is conformable to tissue. The conformability of the catheter tip can help ensure that the sensing electrodes directly contact the tissue being ablated, which is expected to improve the quality of electrograms and accuracy with which the lesion size can be estimated based on measured impedance values between those electrodes and the return electrode. In addition, when measuring the impedance between the ablation electrode and a return path, the shape activated valves ensure that most of the current path flows through tissue under treatment. Because impedance decreases as the lesion is formed, the impedance value can be used to assess the size of the lesion. Many conventional ablation catheters utilize a measured impedance between the ablation electrode (e.g., the electrode tip) and the return electrode. Because the ablation electrodes of most conventional ablation catheters do not conform to the tissue being ablated and/or do not include shape-activated valves, a significant portion of the RF current path does not flow through tissue under treatment, rendering the impedance value less directly related to that of treated tissue.

Many of the ablation catheter systems described herein allow for improved detection and monitoring of contact between the ablation catheter tip and the tissue to be ablated. In certain implementations, for example, the ablation catheter tip is conformable to tissue and includes a radiopaque material. As a result, deformation of the tip resulting from contact with the tissue to be treated can be easily visualized and detected under fluoroscopy.

In some implementations, the ablation catheter tip is equipped with sensing electrodes that can be used to monitor the shape and/or internal fluid volume of the catheter tip. This information can be used to monitor the degree and location of contact between the catheter tip and the tissue (sometimes referred to as tip to tissue coupling) and can thus be used to assess certain characteristics, such as size and depth, of the resulting lesion. This can provide the physician with greater control over catheter manipulation and the size of the lesion that is formed.

In some implementations, electrodes are also positioned on an inner surface of the catheter tip. These electrodes can advantageously be used to detect the state of the catheter tip (e.g., a shape of the catheter tip and/or a level of contact between the catheter tip and tissue) and the state of valves in the distal tip (e.g., whether those valves are open or closed). In some examples, these inner electrodes can be used in combination with one or more electrodes positioned on an outer surface of the catheter tip to detect the state of the catheter tip and the state of valves in the distal tip.

In certain implementations, the catheter incudes a concentric electrode that has a central conductive component surrounded by an annular conductive component. Due to this arrangement, the bipolar signals constructed with these two electrodes can reduce or minimize noise and far field effect in collected signals that allow for improved electrograms. Such electrodes can, for example, provide bipolar electrograms that are more consistent across electrode to tissue orientation than those produced with conventional bipolar electrodes.

Furthermore, by driving current between the two concentric electrodes and monitoring values resulting from the driven current (e.g., impedance values, voltage values, current values, etc.), this arrangement can allow for improved detection of contact between the catheter tip (e.g., a region of the catheter tip including the concentric electrode) and tissue.

In some implementations, a pressure sensor can be placed in communication with fluid at the catheter tip. The pressure sensor can be used to detect tissue contact and/or to provide feedback to a pump to reach a desired level of irrigation.

Certain details are set forth in the following description and in FIGS. 1-43 to provide a thorough understandings of various implementations of the disclosure. Other details describing well-known structures and systems often associated with ablation catheters and related systems and methods, however, are not set forth below to avoid unnecessarily obscuring the description of various implementations of the disclosure.

Many of the details, dimensions, angles, and other features shown in FIGS. 1-43 are merely illustrative of particular implementations of the disclosure. Accordingly, other implementations can have other details, dimensions, angles, and features without departing from the spirit or scope of the present disclosure. In addition, those of ordinary skill in the art will appreciate that further implementations of the disclosure can be practiced without several of the details described below.

B. Selected Implementations of Ablation Catheters and Related Systems and Methods FIG. 1 schematically illustrates an ablation system 100 configured in accordance with the present technology during a cardiac ablation treatment being performed on a patient 102. The ablation system 100 includes an ablation catheter 104 that is connected via an extension cable 106 to a catheter interface unit 108. The catheter interface unit 108 can be a computing device that has a display 110, as described in more detail below. A mapping system 112, a recording system 111, an irrigation pump 114, and an ablation generator 116 are connected to the catheter interface unit 108. The irrigation pump 114 is also removably and fluidly connected to the ablation catheter 104 via fluid line 115. The ablation generator 116 is also connected via a wire or cable 117 to a return electrode 118 that is attached to the skin of the patient 102. The recording system 111 can be used throughout the ablation treatment as well as before or after the treatment. The mapping system 112 can be used prior to or during an ablation treatment in order to map the cardiac tissue of the patient 102 and determine which region or regions of the cardiac tissue require ablation.

During a subsequent ablation treatment, the ablation generator 116 controls and provides energy, e.g., RF energy (e.g., electrical energy in the radiofrequency (RF) range (e.g., 350-600 kHz)) to an ablation electrode 120 (shown in FIGS. 3 and 4) applied to the inner surface of a conformable distal tip 122 of the ablation catheter 104. At the same time, the irrigation pump 114 pumps saline to the distal tip 122 of the ablation catheter 104 where it contacts the ablation electrode 120. Shape activated valves 124 (shown in FIGS. 2, 3, and 5) are provided in multiple different portions of the distal tip 122. Each of the shape activated valves 124, as will be discussed in greater detail below, is configured to open when the portion of the distal tip 122 in which that valve is located is brought into contact with tissue of the patient 102. The saline is released from the distal tip 122 via the open valve(s) 124 and serves to cool environment and as a conduit to deliver the energy generated by the ablation generator 116 to the tissue adjacent the open valve(s) 124. The energy travels through the blood and tissue of the patient 102 to the return electrode 118 and in the process ablates the region(s) of tissue adjacent the open valves 124 of the distal tip 122.

Because the distal tip 122 is designed so that only the valves 124 in those regions of the distal tip 122 that are deformed (e.g., due to contact with tissue) are fully opened to permit the saline to pass therethrough, the undesired application of energy to surrounding blood of the patient will be reduced. By directing the saline to a specific targeted tissue region to be treated, this tip design can also increase the efficiency with which the RF ablation treatment can be carried out. For example, less energy can be delivered to the distal tip 122, as compared to the amount of energy required to be delivered to the ablation catheter of many conventional catheters that indiscriminately emit energy from the ablation electrode in all directions, to carry out the RF ablation treatment on the targeted tissue. At the same time, the fully open valves 124 help to ensure that a sufficient volume of saline is delivered to the targeted tissue, which would otherwise be heated the most and is therefore in the greatest need of irrigation. This helps to prevent the targeted tissue from overheating and thus helps to prevent the generation of steam pop and/or blood coagulation. As will be discussed in greater detail below, by directing or guiding the saline toward the targeted tissue and limiting the amount of saline directed to non-targeted tissue regions, the distal tip 122 can also allow for more accurate tracking of the progression of the lesion. For example, impedance values that are measured between the ablation electrode in the distal tip 122 and the return electrode 118 will be more closely correlated with the state of the tissue being treated.

Figure 2:
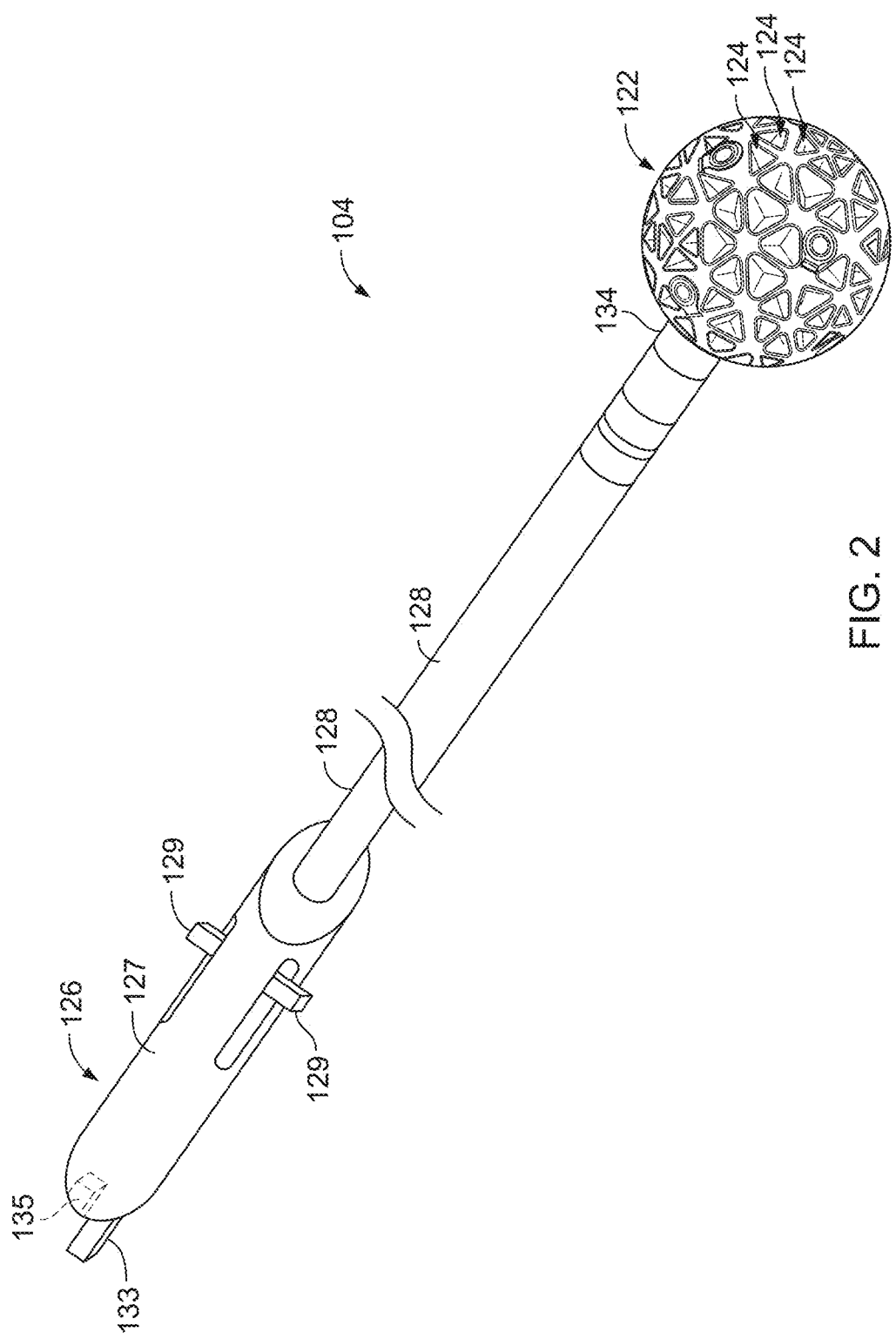
FIG. 2 is a perspective view of an ablation catheter of the ablation system shown in FIG. 1.

Referring to FIG. 2, a handle 126 of the ablation catheter 104 is attached to a proximal end region of a catheter shaft 128, and the distal tip 122 is attached to a distal end region of the catheter shaft 128. The handle 126 includes a housing 127 and lever mechanism 129. The lever mechanism 129 can be operated to deflect the distal end region of the catheter shaft 128. The proximal end region of the handle 126 includes a fluid line connector (e.g., a luer connector) 133 to which the fluid line 115 extending from the irrigation pump 114 can be connected for delivering saline the ablation catheter 104. The proximal end region of the handle 126 also includes an electrical connector 135 to which the extension cable 106 extending from the catheter interface unit 108 can be connected for delivering electrical energy from the ablation generator 116 to the ablation catheter 104 and for allowing electrical and temperature data to be delivered from the distal tip 122 to the ablation generator 116 via the catheter interface unit 108.

The handle 126 can be attached to the proximal end region of the catheter shaft 128 using any of various attachment techniques, such as adhesive bonds, thermal bonds, and mechanical connections. The shaft includes a tube that is in fluid communication with the fluid line 115 extending from the irrigation pump 114 and serves to carry saline from the proximal end of the ablation catheter 104 to the distal tip 122. The shaft also includes electrical wires that carry signals from various sensors on the distal tip 122 to the catheter interface unit and that carry electrical power from the ablation generator to the distal tip 122. The shaft further includes wires that are attached at their distal ends to a ring secured to a distal end region of the catheter shaft 128 and that are attached at their proximal ends to the lever mechanism 129 of the handle 126 to allow the user to apply tension to the wires to deflect the distal end region of the catheter 104 for steering purposes.

In some cases, a magnetic position sensor is also positioned in the distal end region of the catheter shaft 128. The position sensor can, for example, include one or more coils configured to detect signals emanating from magnetic field generators. One or more coils for determining position with five or six degrees of freedom can be used. The magnetic field detected by the position sensor can be used to determine the position of the distal end of the catheter shaft 128.

The distal end region of the catheter shaft 128 includes electrodes 134. These can be used for measuring unipolar and bipolar electrograms. The same electrodes can be separately or concurrently used to support an impedance or current based localization system. A location signal, either passively measured or driven between these electrodes and another node, can be used to determine electrode and/or catheter location. In addition, the electrodes can be used to relate location signals (e.g. potential field measurement and/or impedance) measured through them, with locations determined using an independent localization system (e.g. a magnetic localization system described above) to support a hybrid magnetic and impedance based localization.

Figure 3:
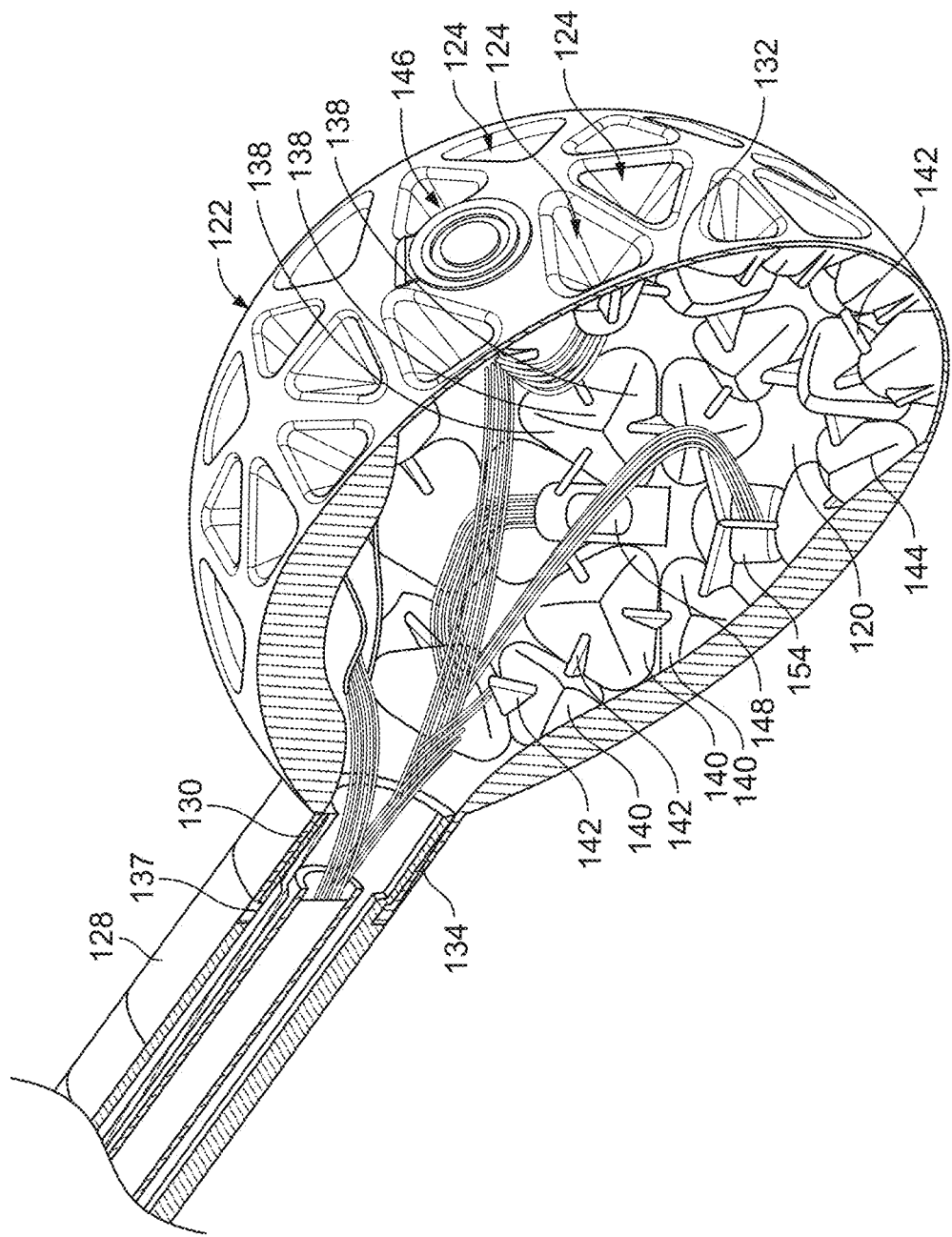
FIGS. 3 and 4 are perspective and side cross-sectional views, respectively, of a distal end region of the ablation catheter shown in FIG. 2.
Figure 4:
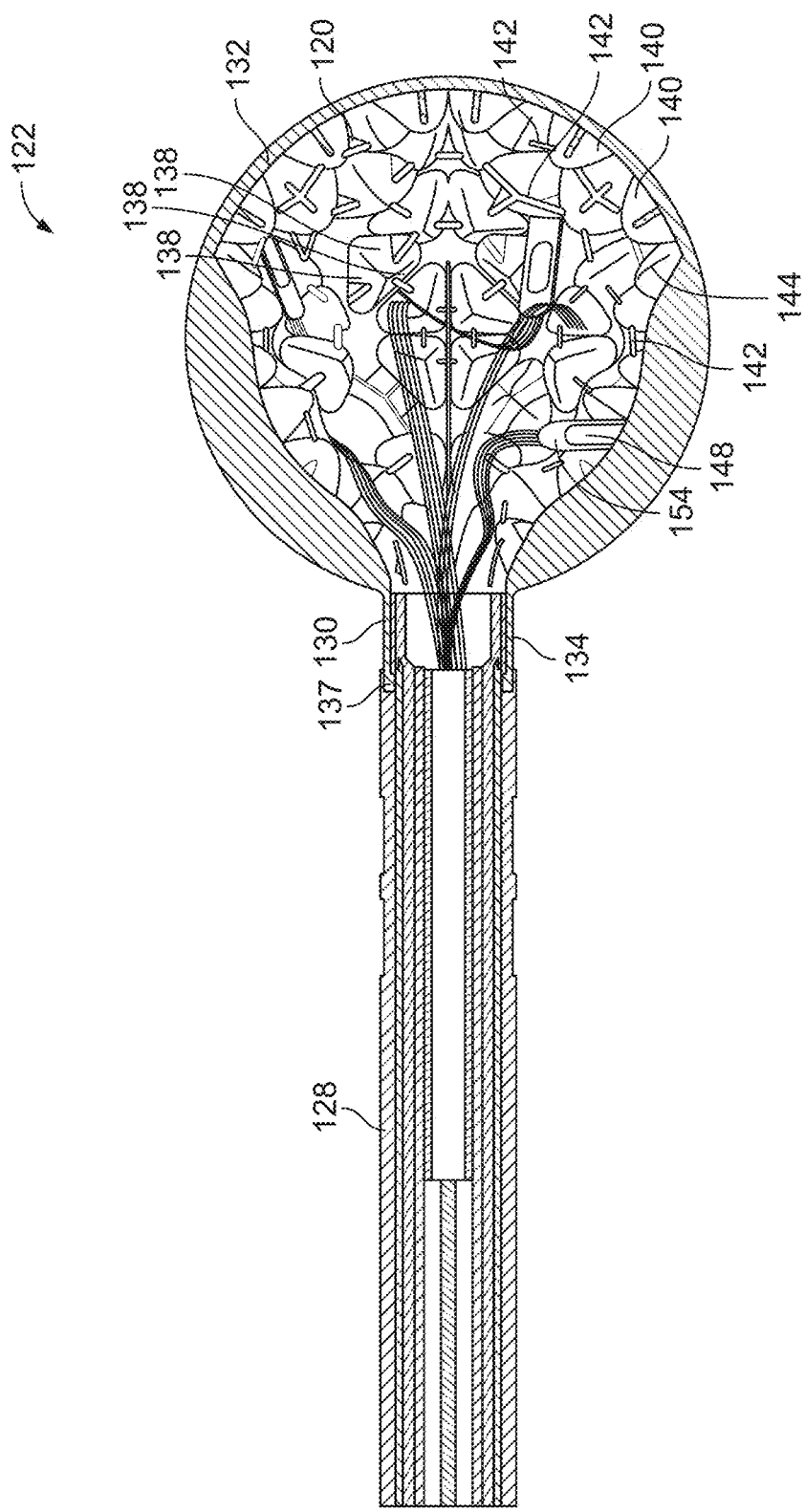

As shown in FIGS. 3 and 4, the outer surface of the distal end region of the catheter shaft 128 is attached to the inner surface of a neck 130 of the distal tip 122. A metallic electrode 134 is positioned over the neck 130 of the distal tip 122 to apply a compression force between the inner surface of the neck 130 and the outer surface of the catheter shaft 128. The metallic electrode 134 can, for example, be swaged to the neck 130. A projection 137 extends from the inner surface of the neck 130 and sits within a recess formed in the catheter shaft 128 to provide the neck 130 and the catheter shaft 128 with a further mechanical connection that helps to prevent axial movement of the distal tip 122 relative to the catheter shaft 128. Alternatively, or additionally, the inner surface of the neck 130 can include a recess that receives a projection extending from the outer surface of the catheter shaft 128 to provide a mechanical connection between those components. Alternatively, or additionally, an appropriate (e.g. RTV silicone) adhesive can be used to bond the neck and/or the protrusion to the distal end of the shaft.

The catheter shaft 128 can be formed of any of various different biocompatible materials that provide the catheter shaft 128 with sufficient pushability and flexibility to allow the catheter shaft 128 to be navigated through blood vessels of a patient. Examples of suitable materials from which the catheter shaft 128 can be formed include polyether block amide sold under the trademark PEBAX and commercially available from Arkema, Inc. of King of Prussia, nylon, polyurethane, thermoplastic polyurethanes sold under the trademark PELLETHANE, and commercially available from Lubrizol Corp. of Wickliffe, Ohio, and/or silicone. In certain implementations, the catheter shaft 128 includes multiple different materials along its length. The materials can, for example, be selected to provide the catheter shaft 128 with increased flexibility at the distal end, when compared to the proximal end of the catheter shaft 128, which can help to provide the catheter shaft 128 with sufficient levels of pushability and flexibility to allow the catheter shaft 128 to traverse tortuous blood vessels, while still allowing flexing and steering of the distal end. The catheter shaft 128 can also include a tubular braided element that provides torsional stiffness while maintaining bending flexibility to one or more regions of the catheter shaft 128.

The ablation catheter 104 is typically provided with a sheath (e.g., an insertion sheath) 139 (shown in FIG. 8) that can be positioned around the distal end region of the catheter shaft 128 and the distal tip 122 to constrain the distal tip 122 in a collapsed position. Constraining the distal tip 122 in a collapsed configuration in this way permits the distal tip 122 to be inserted into a patient via an introducer sheath prior to carrying out an ablation treatment. After being used to position the collapsed distal tip 122 within the introducer sheath, the insertion sheath 139 can be proximally retracted from the distal tip 122.

Figure 5:
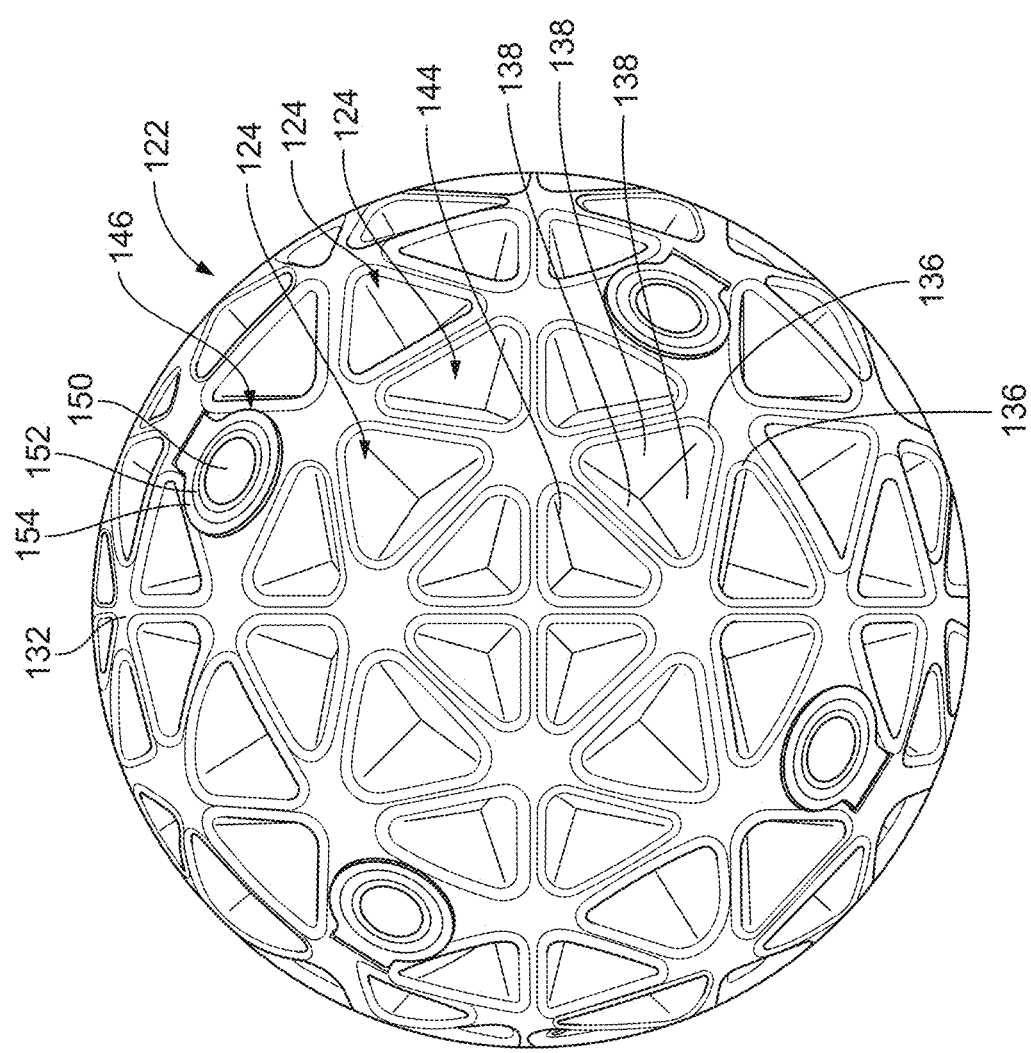
FIG. 5 is an enlarged view of a conformable tip of the ablation catheter shown in FIG. 2.

Referring now to FIGS. 3-5, which show the distal tip 122 in a nominal or expanded state, the distal tip 122 includes a generally spherical body 132 that extends distally from the neck 130. The spherical body 132 is capable of conforming to tissue. In addition, the spherical body 132 is collapsible to a size (e.g., diameter) significantly smaller than the size (e.g., diameter) of the spherical body 132 in its nominal or expanded state. As will be discussed below, the collapsibility of the spherical body 132 allows the distal tip 122 to be delivered via a sheath (e.g., an 8F introducer sheath) and through the vasculature of the patient to a treatment site and then allowed to elastically expand to a significantly larger diameter, which allows for the formation of larger lesions than many conventional ablation catheters that do not include collapsible and expandable ablation tips.

The spherical body 132 can be any size that allows the distal tip 122 to be delivered to a region of tissue to be treated and that is capable of generating a lesion of a size desired by the operator (e.g., physician). In certain implementations, the spherical body 132 of the distal tip 122 has a diameter of 2.0 mm to 25 mm (e.g., 5 mm, 10 mm, and 12 mm). The wall thickness of the spherical body 132 can have a thickness of 10 μm to 1000 μm (e.g., 25 μm to 800 μm, 25 μm to 400 μm, 50 μm-500 μm, 100 μm-1000 μm, and so forth).

The spherical body 132 of the distal tip 122 can be formed of one or more biocompatible materials that allow the spherical body 132 to conform to tissue and to be collapsed within a sheath while also providing sufficient strength or rigidity to permit shape activation of the valves 124. In some implementations, the material from which the spherical body 132 and the neck 130 are formed has a durometer of 10 shore A to 70 shore D (e.g., 40 shore A). In certain implementations, the spherical body 132 and the neck 130 include one or more of silicone, fluorosilicone, urethane, polyethylene, a polycarbonate-based thermoplastic urethane sold under the trademark CHRONOFLEX and commercially available from AdvanSource Biomaterials of Wilmington, Mass., a biocompatible elastomer solder under the trademark CHRONOPRENE, also commercially available from AdvanSource Biomaterials, PEBAX, Nylon, polyurethane, etc. In some implementations, the material from which the spherical body 132 is formed can be loaded with a radiopaque additive, such as a barium sulfate additive. The radiopaque additive permits the spherical body 132 to be visualized using fluoroscopy during an ablation treatment.

In some implementations, the spherical body 132 is formed of a material that has a relatively high thermal conductivity and a relatively low electrical conductivity. The spherical body 132 can, for example, be formed of a polymer, such as silicone, that is loaded with a material, such as barium sulfate or bismuth. Adding certain materials with high thermal conductivity to the polymer body can increase the thermal conductivity of the body, which can help to distribute heat throughout the material of the distal tip 122 and prevent localized hot spots.

In certain implementations, the spherical body 132 has a diameter of 10 mm, a wall thickness of 150 μm, and is formed of silicone loaded with barium sulfate. It has been found that such a construction allows the distal tip 122 to be retracted through an 8F introducer sheath for delivery into the patient and enables operation of the shape activated valves 124 under normal conditions of use.

As shown in FIG. 5, the spherical body 132 of the distal tip 122 forms multiple triangular or tetrahedral depressions 136 that extend inwardly from the outer surface of the distal tip 122. More specifically, the depressions or recesses 136 are formed by the outer surfaces of three triangular walls 138 that extend inwardly (i.e., toward the interior of the spherical body 132). These walls 138, as shown in FIGS. 3 and 4, project inwardly into the interior volume of the spherical body 132 to form projections 140 in the shape of tetrahedrons. Each wall 138 of each projection 140 is structurally connected to an adjacent wall 138 of a neighboring projection 140 by a rib 142. The ribs 142 extend between the inner surfaces (i.e., the surfaces exposed in the interior volume of the spherical body 132) of the walls 138 of the various neighboring projections 140.

Still referring to FIGS. 3 and 4, a slit 144 is formed in a boundary region between each of the triangular walls 138 within each of the projections 140. Each of the slits 144 extends inwardly from a point near the outer surface of the spherical body 132 to the apex of the tetrahedron projection 140 where it connects with the other two slits 144 in the projection 140 to form the shape activated valve 124. As a result of this slit configuration, each of the walls 138 of a given projection 140 is permitted to move relative to the two other walls 138 of the projection 140. Movement of the walls 138 relative to one another allows the slits 144 to increase and decrease in size and thus permits the shape activated valves 124 to be opened and closed.

Figure 6:
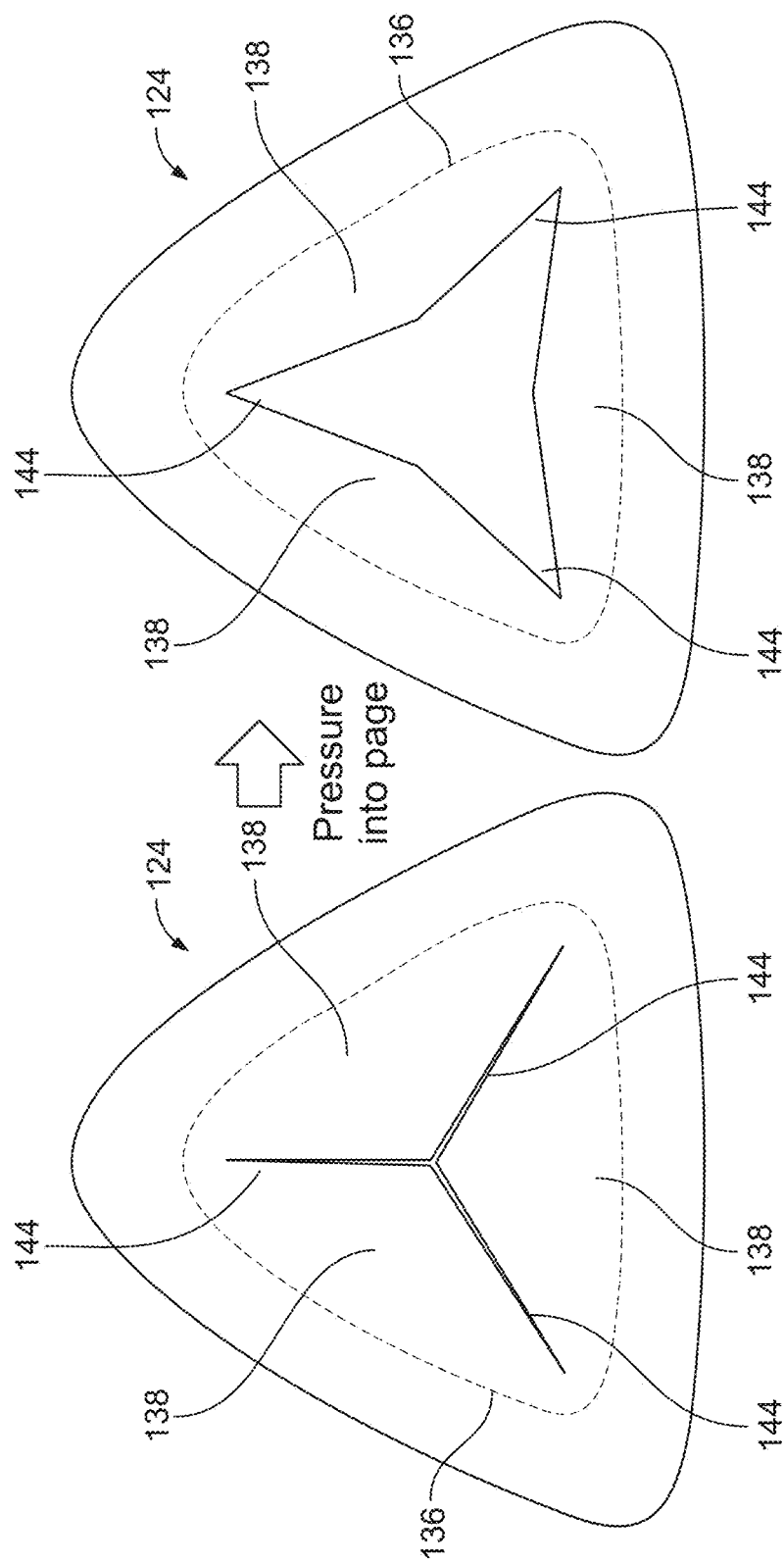
FIG. 6 illustrates a shape activated valve in a closed state (left) and in an open state (right).

Referring to FIG. 6, as a normal force is applied to the outer surface of the distal tip 122 in the vicinity of one of the shape activated valves 124, one or more of the three side walls 138 move away from each other, thereby increasing the size of the slits 144 and opening the valve 124. As the region of the distal tip 122 contacted by the tissue deforms from its normal nominal shape to a deformed, more concave shape, the inner and outer surfaces of the distal tip 122 bend at different bending radii. Due to the deformation of the wall of the distal tip 122 in this way, the inner surface experiences tensile forces, while the outer surface experiences compressive forces. The tension at the inner surface of the distal tip 122 causes the walls 138 of the valves 124 experiencing the tensile force to move away from one another. Because the side wall regions that form the slits 144 are radially inwardly spaced from the outer surface of the distal tip 122, those side wall regions tend to experience tensile forces in response to radially inward deformations of the distal tip 122. This helps to ensure that the slits 144 widen to open the valves 124 as the distal tip 122 is deformed.

The ribs 142 that extend between walls 138 of adjacent valves 124 provide the valve walls with increased rigidity for valve function, while also occupying a relatively small volume. This permits the average wall thickness of the distal tip 122 to be kept very small (e.g., 0.15 mm), which provides the distal tip 122 with high flexibility and the ability to be collapsed to small sheath diameters (e.g., 2 mm to 3 mm). Thus, the ribs 142 help to ensure that the distal tip 122 is collapsible to an extent that the catheter 104 can be navigated through blood vessels of the patient and can then be expanded to its normal, spherical shape at a treatment site. The thin wall structure of the distal tip 122, which is permitted in part by the presence of the ribs 142, provides the distal tip 122 with sufficient flexibility to be deformed by relatively small forces (e.g., 1 to a 100 grams, 20 to 100 grams, 30 to 100 grams, 40 to 100 grams, 75 to 100 gram, and so forth) applied to the distal tip 122 during ablation treatments as a result of contact between the distal tip 122 and the tissue being ablated.

Due to the tension experienced at the inner surface of the distal tip 122 as the distal tip 122 is radially inwardly deformed, the ribs 142 associated with those valves 124 in the regions experiencing the tension also tend to pull the side walls 138 to which the ribs 142 are attached away from the center regions of the valves 124, thereby widening the slits 144. In this way, the ribs 142 can help to facilitate opening of the valves 124. The ribs also help to prevent the valves 124 from opening in response to internal fluid pressure within the distal tip 122.

The tetrahedral recesses 136 formed by the outer surfaces of the side walls 138 provide relief to portions of the outer surface of the distal tip 122 that experience compression during radially inward deformation of the distal tip 122. The tetrahedral recesses 136 also act to counter any tendency of the valve to close near the outer surface due to these compression, resulting in a reduction the force required to deform the distal tip 122 and open the valves 124 in the deformed region of the distal tip 122.

The structure of the distal tip 122 can allow the valves 124 to be opened with very little force applied to the distal tip 122. As discussed below, the ability of the valves 124 to reliably open in this manner can help to ensure that the valves 124 in the region(s) of the distal tip 122 that contact(s) tissue during treatment will allow saline to exit those valves 124 and carry energy, e.g., electromagnetic energy and RF energy, to the adjacent tissue to ablate the tissue. Because only the valves 124 in deformed regions of the distal tip 122 tend to fully open, the design of the distal tip 122 tends to restrict the release of saline (and thus the energy carried by the saline) largely to regions of the distal tip 122 in proximity to tissue deforming the distal tip 122. The valves 124 that are in undeformed regions of the distal tip 122 tend to remain closed. As a result, the amount of saline and energy delivered to the surrounding area not in contact with the distal tip 122 is limited and wasted energy, e.g., energy directed away from the tissue, is minimized.

In addition, limiting the amount of saline (and energy carried by the saline) that is released from those closed valves 124 helps to ensure that most of the electrical energy delivered to the saline by the ablation generator is transmitted to the tissue desired to be ablated via the open valves 124 resulting in an efficient treatment. Carrying out the treatment efficiently in this manner (i.e., without significant energy losses to locations that are not desired to be treated) allows the use of relatively low power ablation generators. In many cases, for example, the same ablation generators that are used to power conventional ablation catheters having rigid ablation tips of much smaller diameters than the expanded distal tip 122 can be used to carry out procedures using the ablation catheter 104.

Limiting the amount of saline delivered into the patient in this way also helps to prevent patients from becoming overloaded with fluid and can prevent additional treatments and complications that are associated with excess fluid in patients.

In addition, more efficient delivery of energy to tissue can enable standard ablation generators to produce larger lesions than those produced by standard ablation catheters, with rigid ablation electrodes. As larger areas of tissue are engaged, more current is required to achieve the requisite current density in the tissue targeted for treatment. Using the same energy limits, while directing all or most of the available current toward the targeted tissue enables a larger area to be ablated relative to the area that would be ablated by most ablation catheters.

Figure 7:
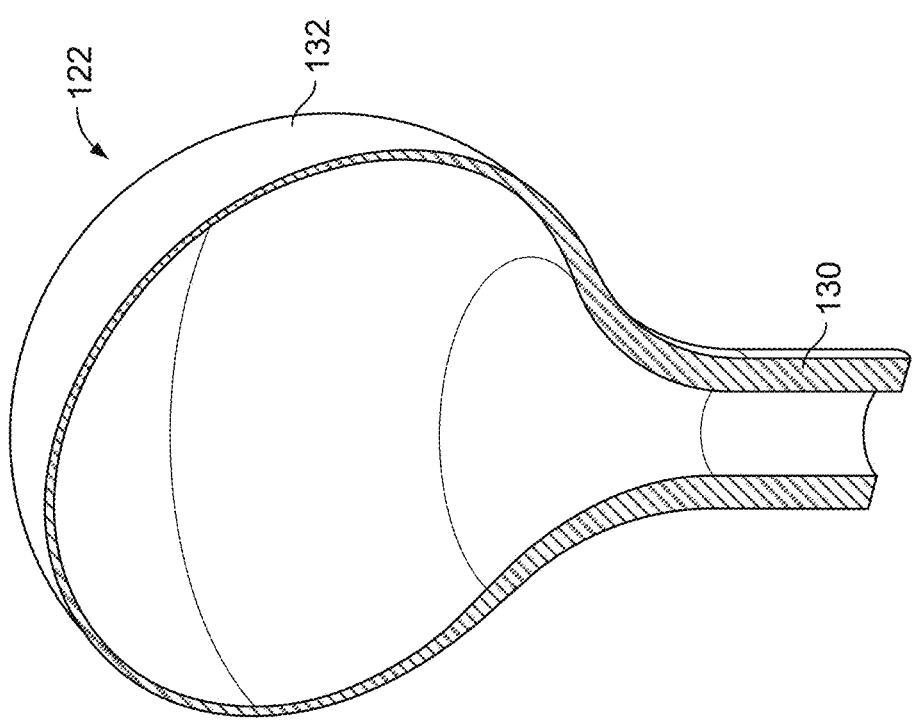
FIG. 7 is a simplified cross-sectional view of the conformable tip of the catheter shown in FIG. 2, showing a change in a wall thickness along the conformable tip.

To help ensure that the contact region of the distal tip 122 experiences deformation upon contacting tissue, the neck 130 and the proximal end region of the spherical body 132 have a greater wall thickness than the distal portion of the spherical body 132, as shown in FIG. 7, which illustrates a simplified cross-section of the distal tip 122. Specifically, the wall thickness is greatest at the neck 130 and gradually decreases up to about the mid-point (i.e., the equator) of the spherical body 132. The thicker proximal end region and of the distal tip 122 and neck 130 act as a support structure to limit proximal movement of the proximal end region of the distal tip 122 in response to a proximal force being applied to the distal end portion of the distal tip 122 or in response to a bending moment be applied from a lateral force in the case of side-contact.

As the ablation catheter 104 is advanced distally into contact with tissue, a proximal axial force will be applied to the distal end of the distal tip 122. Alternatively, as the tip is flexed into side-contact with tissue, a lateral force at the contact region will result in a bending moment at the neck. The added axial and bending stiffness provided by the thickened walls at the proximal end region of the distal tip 122 inhibits (e.g., prevents) deformation of the proximal end region of the distal tip 122 resulting from these forces and thus permits localized deformation at the tissue contact region of the distal tip 122. The localized deformation in the tissue contact region of the distal tip 122 causes the valves 124 within the deformed region to open and thus allows saline carrying energy to escape through those valves during treatment to ablate tissue adjacent the deformation. The valves 124 in the undeformed regions of the distal tip 122 will remain closed, thereby limiting the escape of saline and energy to tissue and bodily fluids other than the tissue adjacent the deformed distal end region of the distal tip 122.

The distal half of the spherical body 132 in FIG. 7 has an approximately constant wall thickness that is less than the neck 130 and the proximal half of the spherical body 132. In other implementations, the wall thickness can increase again in the distal end region of the spherical body 132. This can, for example, increase the ease with which the distal tip can be manufactured using certain manufacturing techniques (e.g. injection or blow-molding.)

Without added support in the proximal end region of the distal tip 122, a proximal axial force and/or a lateral force applied to the distal tip 122, might cause the spherical body 132 to shift and/or bend without causing a localized deformation at the distal end of the distal tip 122. This could result in none of the valves 124 being opened or could even result in certain valves 124 at the proximal end of the distal tip 122 being opened while the valves 124 at the distal end of the distal tip 122 remain closed. In addition, if the proximal end region bends, a reduced surface of the distal tip engages tissue. As a result, the tissue desired to be treated adjacent the distal end region of the distal tip 122 would not be ablated, and electric current would be ineffectually directed through the open proximal valves. The support provided by the thickened wall in the proximal end region of the distal tip 122 can prevent this from occurring.

Referring again to FIGS. 3 and 4, the ablation electrode 120 of the ablation catheter 104 is in the form of a continuous conductive layer applied to the inner surface of the distal tip 122. The ablation electrode 120 coats the inner surface of the spherical body 132 and the neck 130 of the distal tip. The ablation electrode 120 is flexible and thus permits the distal tip 122 to expand and collapse without affecting the ability of the ablation electrode 120 to carry energy. The ablation electrode 120 can include one or more conductive materials, such as silver, carbon, gold, silver-coated glass beads, graphene, etc.

The neck 130 of the distal tip 122, as described above, is connected to the distal end region of the catheter shaft 128. The ablation electrode is electrically connected to the ablation generator via an electrical wire that passes through a lumen of the catheter shaft. The distal end of the wire contacts the ablation electrode and is electrically connected to the electrical connector 135 in the handle 126 of the ablation catheter 104 and can thus carry electrical signal delivered by the ablation generator 116 to the ablation electrode 120. In some cases, an electrically conductive adhesive can be used to electrically connect and secure the ablation electrode to the electrical wire. An electrically conductive adhesive can also be used between the neck 130 and the catheter shaft 128 to secure those components together while enabling energy to freely pass between those components. In other cases, an external compressive force, e.g., a compressive force provided by the electrode 134, can also secure the ablation electrode to the electrical wire by compressing the ablation electrode 120 on the inner surface of the neck 130 against an electrically conductive member, e.g., a wire, exposed along the outer surface of the distal end region of the catheter shaft 128. A component with an insulating outer surface (e.g. a plastic tube) can also be situated beneath the inner surface of an electrically conductive member, e.g., a wire.

During use, as described in greater detail below, the ablation generator 116 delivers energy to the ablation electrode 120 via an electrically conductive member, e.g., a wire. As saline is pumped into the interior of the distal tip 122 by the irrigation pump 114 and the saline exits the open valves 124 of the distal tip 122, the energy is carried from the ablation electrode 120 to tissue of the patient adjacent the open valves 124 by the saline. Because the ablation electrode carries the RF signal very close to the valves, it minimizes the impedance added by passing the current through saline. This, in turn, minimizes energy loss and heating of the saline.

As shown in FIGS. 3-5, the distal tip 122 includes multiple outer sensing electrodes 146, multiple inner sensing electrodes 148, and multiple thermistors. The outer sensing electrodes 146, as will be explained in greater detail below, can be used to detect electrical signals emitted from other electrodes of the distal tip and/or to detect electrical signals emitted from the heart of the patient during use. Referring to FIG. 5, each of the outer electrodes 146 includes a central conductive component 150 and an annular conductive component 152 that surrounds the central conductive component. The conductive components 150, 152 are attached to flexible printed circuits 154, which are attached to the body of the distal tip 122. Each of the conductive components 150, 152 is connected to a wire that extends through the catheter shaft 128 to the catheter interface unit 108 for transferring data signals from the conductive components 150, 152 to the control unit (e.g., processor) in the catheter interface unit 108.

The conductive components 150, 152 are typically thin pieces of thermally and electrically conductive materials. Examples of suitable materials from which the conductive components 150, 152 can be formed include copper, gold, nickel, etc. In certain implementations, the conductive components can be coated with a specialized coating, such as sputtered or electroplated iridium oxide. This coating can reduce the electrical impedance of the saline-electrode interface, thereby reducing noise pickup for cardiac waveforms with micro-volt scale amplitudes.

The central conductive component 150 typically has the same surface area as the annular conductive component 152. This can permit the conductive components to have identical impedance to the surrounding blood and can limit noise when used to provide bipolar intracardiac electrograms. In some implementations, each of the conductive components has a surface area of 0.25 mm$^2$ to 1 mm$^2$ (e.g., 0.5 mm$^2$).

The concentric design of the conductive components 150, 152 reduces and in some cases eliminates the effect on the collected signal of the electrode pair orientation relative to tissue when the electrode is pressed against the tissue. Because the distal tip conforms to a tissue surface, the concentric electrodes can be pressed flat against a tissue surface, which further reduces orientation impact on bipolar signal constructed with the pair. In addition, the far field effect is minimized because the relatively small size and close spacing between the electrodes helps to ensure that they measure signals from the underlying tissue. The insulating deformable material of the distal tip also minimizes the far field effect of signal pickup from neighboring tissue. Furthermore, the separation of these electrodes from the ablation electrode reduces noise pickup during ablation. In combination, these properties provide localized electrograms that are consistent and easily interpreted. Conventional bipolar electrode pairs often have mismatched surface area (e.g., where the surface area of the ablation electrode exceeds the surface area of the other electrodes) leading to added noise, a bipolar signal whose amplitude and sign are dependent on tip-tissue orientation, larger electrode sizing resulting in more far-field signal from adjacent tissue, and more noise as ablative energy is delivered to one electrode in the pair.

The thermistors are attached to the inner surfaces of the flexible printed circuit 154, opposite the central conductive components 150 of the outer electrodes 146. Each of the thermistors can be used to detect the temperature of its associated outer electrode 146. Any of various types of thermistors and thermocouples can be used. In certain implementations, the thermistors are discrete negative temperature coefficient elements. Because the thermistors are separated from the outer electrodes 146 by only the thin flexible printed circuit material (e.g. polyimide) with relatively high thermal conductance and are separated from the ablation source by the thicker distal tip material (e.g. silicone) with relatively low thermal conductance, the electrical resistance of the thermistors can be used to accurately estimate the temperatures of the outer electrodes 146. Since the outer electrodes 146 are exposed along the outer surface of the distal tip 122 and can be placed in direct contact with tissue of the patient during use, their temperature can provide an accurate indication of the tissue temperature during treatment. Tissue temperature has been found to be a good indicator of ablation lesion formation. In some implementations, temperature data from the thermistors can be used as a safety control to stop ablation delivery if overheating (e.g. >90° C.) occurs.

As shown in FIGS. 3 and 4, the inner electrodes 148 are metal pads that are attached to the inner surfaces of flexible printed circuits 154, which are attached to the body of the distal tip 122. The inner electrodes 148 can be formed of the same material and can have the same surface area of the outer electrodes 146 in order to match the impedance of the outer electrodes 146. The inner electrodes 148 can be used to generate and/or measure electrical signals. As will be described in greater detail below, these signals can be used to determine the shape and/or interior volume of the distal tip 122 during treatment. In addition, they can be used to determine the open/closed state of nearby valves.

The flexible printed circuits 154 to which the outer electrodes 146, the inner electrodes 148, and the thermistors are attached can be formed on one or more biocompatible substrates, such as polyimide or parylene. Metallization layers can include copper or gold. Outer layer can include materials such as polyimide, parylene and others. In some examples, the insulated layer of the distal tip can include a metallization or conductive ink layer that functions as a conductor. In some cases, electrodes can be selectively applied onto one or more layers of the distal tip.

After forming the spherical body 132 and the neck 130 of the distal tip 122, the material of the spherical body 132 can be cut in desired regions to form the slits 144 of the valves 124. The slits 144 can be formed using any of various suitable cutting techniques, including laser cutting, and mechanical cutting (e.g., using a lance).

The various electrodes 146, 148 and thermistors can then be attached to the distal tip 122 using a compliant adhesive, such as a RTV silicone. Alternatively or additionally, the various electrodes and thermistors can be attached to the distal tip via mechanical retaining features (e.g. tabs) added to the perimeter of the flexible circuits that can be inserted into mating hole or slot features molded into the tip. Alternatively or additionally, the electrodes and thermistors can be molded or overmolded into the distal tip during its manufacture. Alternatively, staples or sutures, e.g., of Nylon, can be used to fasten the electrodes and thermistors to the tip.

In some implementations, an additional thermistor can be mounted in thermal contact with the ablation electrode or somewhere inside the tip in thermal communication with the saline. Temperature data from this thermistor can be used as a safety control to stop ablation delivery if overheating (e.g. >90° C.) occurs.

In certain implementations, a pressure sensor (e.g., a MEMS piezo-resistive element) for measuring internal fluid pressure can also be provided in the distal tip 122. The internal fluid pressure sensor can be connected to the catheter interface unit 108 via a wire or cable to transmit pressure data to the control unit of the catheter interface unit 108. This pressure data can be used by the control unit to control the flow rate of saline delivered to the distal tip 122 by the irrigation pump 114. The pressure data can also be used to indicate whether the distal tip 122 is in contact with tissue and to indicate the state of the various valves 124. For example, when the tip is pressed against tissue, causing the valves to open, the resulting fluid pressure drop could be used along with other information to assess the extent of contact. This pressure sensor can be used to titrate irrigation and/or initiate one or more pressure relief functions, e.g., activating one or more pressure relief valves (not shown). Furthermore, such pressure drops would not be as apparent if measured with a sensor at the proximal end of the irrigation lumen due to that lumen's high fluid flow resistance (as a long, narrow tube). As such, it is advantageous for this reason to have a pressure sensor near the tip, on the other side of that resistive lumen. In an example with a uniform hole pattern, rather than shape activated valves, the pressure sensor will indicate the amount of surface area engaging with tissue. Holes pressed against tissue will experience greater resistance to flow and subsequently cause an increase in pressure. The increase in pressure for a given flow will provide an indication of amount of coupling between the tip and tissue.

Referring again to FIG. 1, the catheter interface unit 108 acts as the interface between the ablation catheter 104 and other instrumentation of the ablation system 100. In some implementations, the catheter interface unit 108 acts as a control unit for controlling the ablation system 100. The mapping system 112, the recording system 111, the irrigation pump 114, and the ablation generator 116 are connected to the catheter interface unit 108 via electrical cables 155, 156, 157, and 159, respectively.

The catheter interface unit 108 is operably connected to the ablation generator 116 such that the catheter interface unit 108 can receive data from the various sensors and/or control the output of or communicate with the ablation generator 116 according to a predetermined scheme and/or user input. The catheter interface unit 108 can be a computing device that is running a general purpose operating system (e.g., a Unix-like operating system such as Linux). The catheter interface unit 108 can include any suitable logic processor (e.g., control circuit), hardware, software, firmware, or any other logic control adapted to perform the features discussed herein. In some implementations, the ablation generator 116 includes its own controller for controlling the generator based on data received from the sensors at the distal tip 122.

The catheter interface unit 108 can also include a current source that can generate a signal at a frequency above the cardiac band (e.g., 5 kHz). The signal can be a sinusoidal signal with an amount of current below the stimulation threshold of cardiac tissue. For example, at 5 kHz, 50 µA can be safely used in the cardiac chamber. The signal can be generated as current driven between various sets of electrodes on the catheter 104, or between those electrodes and the ablation return electrode, and/or between those electrodes and other cutaneous electrodes while collecting corresponding data in response to this current on other driven and passive electrodes. In order to drive multiple sets of electrodes and generate corresponding measurements, various multiplexing schemes such as time division, frequency division, code division and any combination thereof can be used. The current source and acquisition hardware can be implemented using discrete analog circuitry to modulate and demodulate the signals, and can also use digital to analog and analog to digital conversion to perform some of these tasks digitally using elements such as a central processing unit, digital signal processor, field programmable gate array, etc.

As an alternative to or in addition to driving current between electrodes, a sinusoidal or square wave voltage can be driven between them. For example, the catheter interface unit 108 can include a voltage source that can generate a sinusoidal or square wave voltage signal at a particular frequency, thereby resulting in a current having a particular magnitude (e.g., a magnitude below the stimulation threshold of cardiac tissue).

The catheter interface unit 108 includes a user interface panel, which typically includes the display 110, indicators, and switches to permit the operator to monitor and control delivery of energy to the catheter 104 from the ablation generator 116. The catheter interface unit 108 can also include a computer interface module such as a touchscreen and/or keyboard and mouse. The catheter interface unit 108 can display a variety of information related to the ablation procedure. For example, the catheter interface unit 108 can display a digital readout of the actual power, voltage and current being delivered, the calculated impedance (e.g., based on measured current and voltage) between the ablation electrode 120 and the return electrode 118 during the delivery of energy, the measured tissue temperature on the various sensors, the number of times the ablation generator 116 has been activated, and/or the total elapsed time during which energy has been delivered to the patient. In some cases, the catheter interface unit 108 displays data that represents the shape of the distal tip 122 or the shape and/or progress of the lesion being generated by the ablation catheter 104. This information can be represented in graph form, as two-dimensional images, and in three-dimensional surface representing the distal tip. The information can also be transferred to a mapping system and be represented in a three-dimensional electro-anatomical context.

The irrigation pump 114 is a pumping mechanism that can be connected to a saline reservoir and operated to cause the saline to flow through the catheter 104 and exit the distal tip 122. In some cases, the irrigation pump 114 contains the fluid reservoir for storing the saline, while in other cases, the irrigation pump 114 can be connected to a separate source of saline, such as a saline bag. The irrigation pump 114 can, for example, be a peristaltic pump.

The mapping system 112 includes a mapping signal processor that can be connected to the sensing electrodes of the ablation catheter 104 to detect electrical activity of the heart. This electrical activity can be evaluated to analyze an arrhythmia and to determine where to deliver the ablation energy as a therapy for the arrhythmia.

As discussed above, the return electrode 118 can be separately connected to the ablation generator 116 via the cable 117. The return electrode 118 is configured for attachment to a patient's skin surface to complete the circuit necessary for the application of energy to the tissue of the patient. During treatment, RF power that is supplied by the ablation generator 116 is transmitted through tissue of the patient, between the ablation electrode 120 in the distal tip 122 of the catheter 104 and the return electrode 118, to heat the tissue in the immediate vicinity of the tip to a temperature sufficient to cause ablation. The heating of the tissue can be controlled by the catheter interface unit 108 or ablation generator 116, through controlling the amount of energy generated by the ablation generator 116 and the amount of irrigation delivered by the pump. The RF power that is supplied can be chosen such that the desired amount of tissue ablation occurs.

A method of using the ablation system 100 to perform a cardiac ablation treatment will now be described. Depending on the specific arrhythmia, the location or region of tissue targeted for ablation can be anatomically guided or determined by mapping the relevant chamber or chambers of interest. Subsequently, those regions of cardiac tissue can be ablated in the manner described below. In some cases, the ablation catheter 104 and/or a mapping catheter performs mapping function before and/or during an ablation treatment.

Figure 8:
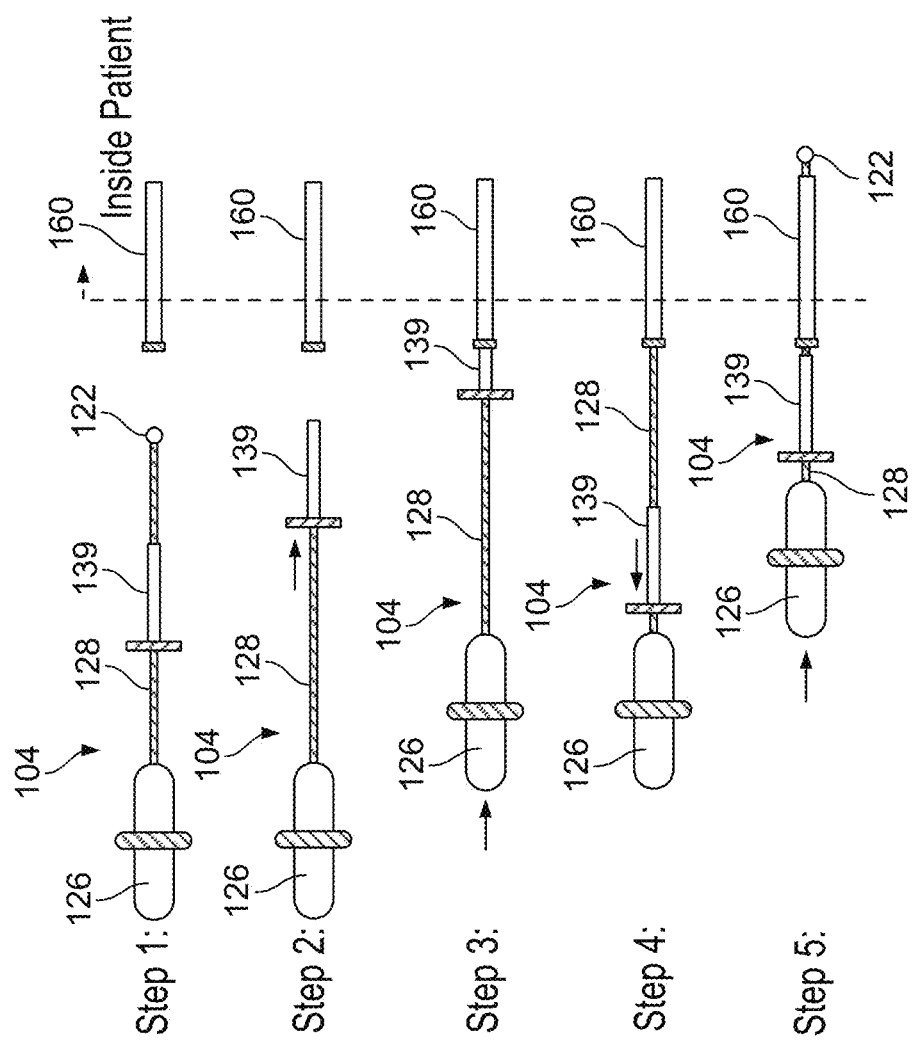
FIG. 8 schematically illustrates a method of inserting the ablation catheter shown in FIG. 2 into a patient.

To perform a cardiac ablation treatment, the distal end of the ablation catheter 104 is first introduced into the patient, typically via a femoral vein or artery. FIG. 8 schematically illustrates a series of steps carried out to introduce the ablation catheter 104 into the patient. In step 1, an introducer sheath 160 is positioned within a blood vessel of the patient (e.g., the femoral artery of the patient) and the ablation catheter 104 is positioned for insertion into the introducer sheath 160. As a second step, the user grasps the handle 126 of the catheter 104 and distally advances the insertion sheath 139 along the catheter shaft 128 until the insertion sheath 139 surrounds the distal tip 122. As the insertion sheath 139 is advanced over the distal tip 122, the distal tip 122 collapses to a diameter capable of being inserted into the introducer sheath 160. The user then, in step 3, inserts the insertion sheath 139 containing the distal tip 122 into the introducer sheath 160 and distally advances the catheter 104. In step 4, after positioning the distal tip 122 within the introducer sheath 160, the distal tip 122 is advanced out of the insertion sheath that is then left surrounding a proximal portion of the catheter shaft 128 throughout the remainder of the treatment. As a fifth step, the catheter is advanced through the introducer sheath 160 and the patient's vasculature until the distal tip 122 reaches the treatment site in the heart of the patient. As the distal tip 122 is extended distally beyond the introducer sheath 160, the distal tip 122 of the catheter is allowed to expand to its nominal configuration.

The advancement of the ablation catheter 104 through the patient's blood vessels and into the patient's heart is typically viewed under fluoroscopy. While the ablation catheter 104 is being passed through the introducer sheath and blood vessels of the patient and into the patient's heart chamber, saline is typically delivered from the irrigation pump 114 to the distal tip 122. Fluid weeps from the distal tip 122 via the closed valves 124 at a low rate (e.g., about 2 ml/min), e.g., during catheter manipulation and mapping, before ablation is initiated or after ablation is completed.

After being positioned in the desired region of the heart, the ablation catheter 104 is advanced into contact with the region of the tissue to be ablated. As discussed above, fluoroscopy can be used to visualize the contact between the distal tip 122 of the ablation catheter 104 and the patient's tissue. Due to the conformability of the distal tip 122, contact with the tissue causes the distal tip 122 to deform. This deformation can be clearly viewed under fluoroscopy. The position sensor within the distal end region of the catheter shaft 128, in combination with the mapping system visualization, can also be used to assist the user in determining whether the distal tip 122 is properly positioned. In addition, the amplitude of the cardiac electric signal (e.g., ECG) detected by the tip surface electrodes will increase as the electrode contacts the heart tissue. The user typically advances the catheter 104 until the distal tip 122 has deformed by an amount equal to ¼ to ½ of the diameter of the distal tip 122 in the undeformed state. This deformation increases the surface area of the distal tip 122 that contacts the tissue and thus increases the surface area of the tissue region that will be ablated. Other methods to determine tip to tissue contact described in this disclosure can also serve to verify proper catheter placement prior to ablation initiation.

When the user is ready to initiate the ablation process, he or she activates the ablation generator 116, causing the ablation generator 116 to deliver energy to the ablation electrode 120 on the inner surface of the distal tip 122. Before the ablation generator 116 is activated, the speed of the irrigation pump 114 is also increased to cause the saline to flow at an increased rate (e.g., 15 ml/min to 30 ml/min). The activation of the ablation generator 116 and the speed increase of the irrigation pump 114 can be triggered via an input device (e.g., button, knob, touchscreen, etc.) of the catheter interface unit 108 and/or of the ablation generator 116. As the saline delivered through the catheter 104 exits the open valves 124 in the regions of the distal tip 122 that are deformed due to contact with the tissue, the energy is transmitted via the saline to the tissue adjacent the open valves 124, thereby ablating that tissue.

In addition to serving as a conduit that carries the energy to the tissue of the patient, the saline also provides a cooling function. The saline can, for example, cool the portions of the tissue nearest the distal tip 122, which tend to receive the lowest cooling due to blood flow and thus absorb the most heat. The saline can help to prevent that tissue from overheating, potentially leading to steam pop, and can help to prevent blood interfacing with the ablation energy from coagulating.

As the tissue is being ablated, the signals of the electrodes 146, 148 thermistors of the distal tip 122, and a pressure sensor are read by the control unit in the catheter interface unit 108 via the cable bundles that extend through the catheter shaft 128. This data can be processed by the control unit in several different ways to assess a state of the distal tip (e.g., the degree of contact between the distal tip 122 and the tissue or a shape of the distal tip 122) and to monitor the progress of the lesion being created by the energy.

The thermistors detect the temperatures of their associated outer electrodes 146 and transmit that temperature data to the control unit of the catheter interface unit 108. The control unit of the catheter interface unit 108 receives the temperature data and uses that data to determine which of those electrodes 146 are in contact with or in close proximity to the tissue being ablated. The thermistors associated with the outer electrodes 146 that are in contact with or in close proximity to the tissue being ablated will detect a greater temperature than the outer electrodes 146 that are farther away from the tissue being ablated. This is because energy is directed towards tissue via the valves and blood flow cools the tip where it is not in contact with tissue. Thus, the control unit can determine which regions of the distal tip 122 are contacting or nearly contacting the tissue by determining which of the outer electrodes 146 have the highest temperatures.

The control unit can also assess the progress of the lesion being generated based on the temperature data received from the thermistors. The design of the distal tip 122 and its outer electrodes 146 and thermistors, as discussed above, allow for accurate temperature readings of the outer electrodes 146 in direct contact with the tissue being ablated and thus in conjunction with power, duration, impedance and tissue coupling parameters allow for more accurate assessment of various characteristics, such as size, shape, and depth, of the lesion being created. The various sensors, in combination with the methods by which they are driven, interrogated, and/or analyzed can provide information indicative of the state of the tip. Information indicative of the state of the tip can be detected by the various sensors described herein, for example, by the inner and outer electrodes, and can be based on impedance measurements between the ablation tip and the return electrode and pressure sensor. The state of the tip can be assessed based on, for example, its shape and the extent and/or locations of open valves. These characteristics in turn can be used to assess the level of coupling between the catheter tip and tissue, and as a safety mechanism indicating a failure. For example, the location and extent of shape deformation can indicate a level of tissue contact and/or coupling. Providing this information, in combination with additional information, can aid to verify proper catheter placement prior to ablation onset. During ablation, this information in addition to knowledge of other parameters such as, for example, temperature, power, and duration, can be used to assess the dimensions of lesion formation. For example, information related to lesion formation can be collected using the temperature sensors and electrodes, and can also be computed using information collected by these sensors. In addition, a change in this information can indicate an undesirable event, such as inadvertent catheter movement of the catheter during ablation.

Current driven across the external and internal electrodes 146, 148 or impedance values measured using voltages detected across the external and internal electrodes 146, 148 can be used to determine whether valves 124 located near those electrodes 146, 148 are in an open or closed state. That information can, in certain circumstances, be used to determine the shape of the distal tip 122. In regions of the distal tip 122 in which the shape activated valves 124 are open, a current is driven between one of the external electrodes 146 and its corresponding internal electrode 148. As the current is driven between the external electrode 146 and its associated internal electrode 148, a detected voltage across those electrodes 146, 148 that is above a threshold voltage is indicative of a closed valve, while a detected voltage across those electrodes 146, 148 that is below a threshold voltage is indicative of an open valve. In circumstances in which the current driven between the external and internal electrodes 146, 148 is not constant, it can be beneficial to calculate the impedance between the external and internal electrodes 146, 148 to determine the state of the nearest valves 124. The impedance can be calculated from the known current driven between the external and internal electrodes 146, 148 at a given time and the voltage detected across those electrodes 146, 148 at that time. A calculated impedance that is above a threshold impedance is indicative of a closed valve, while a calculated impedance that is below a threshold voltage is indicative of an open valve. In addition to determining which of the various valves 124 are open in this way, this information can also allow the shape of the distal tip 122 to be estimated. In some implementations, particular impedance values (or, e.g., combinations of particular impedance values between various electrodes) can correspond to open/closed states of various values. In this way, the open/closed states of the values can be mapped to an impedance profile of the electrodes.

The determination in the manner described above of which valves 124 are open and which valves 124 are closed can also be used for other reasons. For example, this information can be used to confirm that all valves 124 within a deformed region of the distal tip 122 that is in contact with tissue are in fact open, as would be expected. A determination that one or more of the valves 124 in a deformed region of the distal tip 122 has not opened can be indicative of an error in either the determination of the state of the distal tip 122 or the determination of the valve state.

The internal electrodes 148 alone can also be used to determine the shape of the distal tip 122 and thus to determine whether and to what extent certain regions of the distal tip 122 are in contact with the tissue. For example, the control unit can cause a current to be driven from one of the internal electrodes 148 to another of the internal electrodes 148 and the voltage across those electrodes can be monitored. The particular electrodes through which the current is driven can be controlled using various multiplexing schemes, as described above. The distance between those electrodes can be determined based on the voltage detected. For example, as the distance between two electrodes decreases, the detected voltage across those electrodes will decrease, and vice versa. In this way, by repeating this process across the different pairs of internal electrodes an approximate shape of the distal tip 122 can be determined based on the voltage detected across the electrodes 148.

In some implementations, a current is driven from one of the internal electrodes 148 to another of the internal electrodes 148 while other internal electrodes 148 (referred to in this case as passive electrodes) detect a voltage. The voltages detected by the passive electrodes can be used to determine the approximate shape of the distal tip 122 by fitting the measurements collected by them to either a lookup table or a mathematical model mapping these measurements to various shapes.

It should be appreciated that the outer electrodes can also be used to determine shape in a manner similar to the one described above.

It should further be appreciated that by determining the catheter tip shape, saline volume at the tip can also be estimated as the volume of the shape. Furthermore, saline volume can be estimated independently of the specific shape using data collected by the various tip electrodes. Saline volume provides an indication of tip to tissue coupling. The smaller the volume of saline, the more deformed that tip is and therefore, the more coupled it is to the tissue surface.

The outer electrodes 146 can also be used to generate unipolar and bipolar electrograms.

Additionally, the impedance between the outer electrodes 146 and the return electrode 118 can be used to assess lesion progress. As the tissue is ablated adjacent a particular outer electrode 146, the impedance between that outer electrode 146 and the return electrode 118 decreases. Thus, the measured impedance values between the various outer electrodes 146 and the return electrode 118 can be used to provide feedback on the ablation lesion. When a constant current is used, a detected voltage across the outer electrode 146 and the return electrode 118 is proportional to the impedance and can thus be used to provide feedback on lesion progress. In some implementations, lesion progress can be assessed simultaneously with tissue ablation. For example, a 500 kHz signal can be used for ablation, and a 5 kHz signal can be used to assess lesion progress so that the signals can be distinguished.

The impedance between the ablation electrode 120 and the return electrode 118 can also be used to assess lesion progress. As tissue is ablated between the ablation electrode 120 and the return electrode 118, tissue impedance decreases and therefore impedance between those electrodes decreases. Thus, the measured impedance values between the ablation electrode 120 and the return electrode 118 can be used to provide feedback on lesion progress. As noted above, when a constant current is used, a detected voltage across the ablation electrode 120 and the return electrode 118 is proportional to the impedance. Various multiplexing schemes can be used to control which electrodes are used for ablation and which electrodes are used for assessing lesion progress.

Additionally, the signal resulting from the ablation signal (e.g., the 500 kHz ablation signal) emanating from the ablation electrode 120 to the return electrode 118 can be analyzed on inner electrodes 148 and outer electrodes 146. The amplitude and phase of the difference between electrodes 146 and 148 can be analyzed similar to a 4-wire resistance measurement. Reduction in amplitude and a phase change are indicative of impedance change in nearby tissue, which in itself, is indicative of tissue temperature and lesion progress.

The concentric design of the outer electrodes also allows determining whether they are in tissue contact. By driving a current between two outer electrodes and measuring the impedance between them, electrode-tissue contact can be determined. Since the impedance of tissue is roughly 2.5 times that of blood, there will be approximately a 2.5 impedance rise between the concentric electrodes when in contact with tissue relative to a state where they are largely in blood contact. In order to determine tissue contact, baseline impedance values can be saved when the tip is confirmed not to be in contact with tissue. This can be done guided by fluoroscopy, the shape detection, or other means. This can be done automatically by the software, or initiated by the computer operator. Alternatively, typical values can also be stored in the computer program. Once the impedance value between the two concentric electrodes exceeds a certain threshold, for example 1.5 times baseline, contact between the electrodes and tissue can be indicated to the physician.

The control unit of the catheter interface unit 108 can process the above-discussed data from the thermistors, the internal electrodes 148, the external electrodes 146, and the return electrode 118 in any of the various ways discussed above to determine or approximate the shape of the distal tip 122 and/or characteristics of the lesion created. The control unit can then generate and output signals to the display 110 of the catheter interface unit 108 that are representative of the shape of the distal tip 122 and/or the characteristics of the lesion. The shape of the distal tip 122 and/or the characteristics of the lesion can then be displayed on the display 110 of the catheter interface unit 108. The physician can use this image to better understand the type of contact the distal tip 122 is making with the tissue and the size and shape of the lesion being formed.

Figure 9:
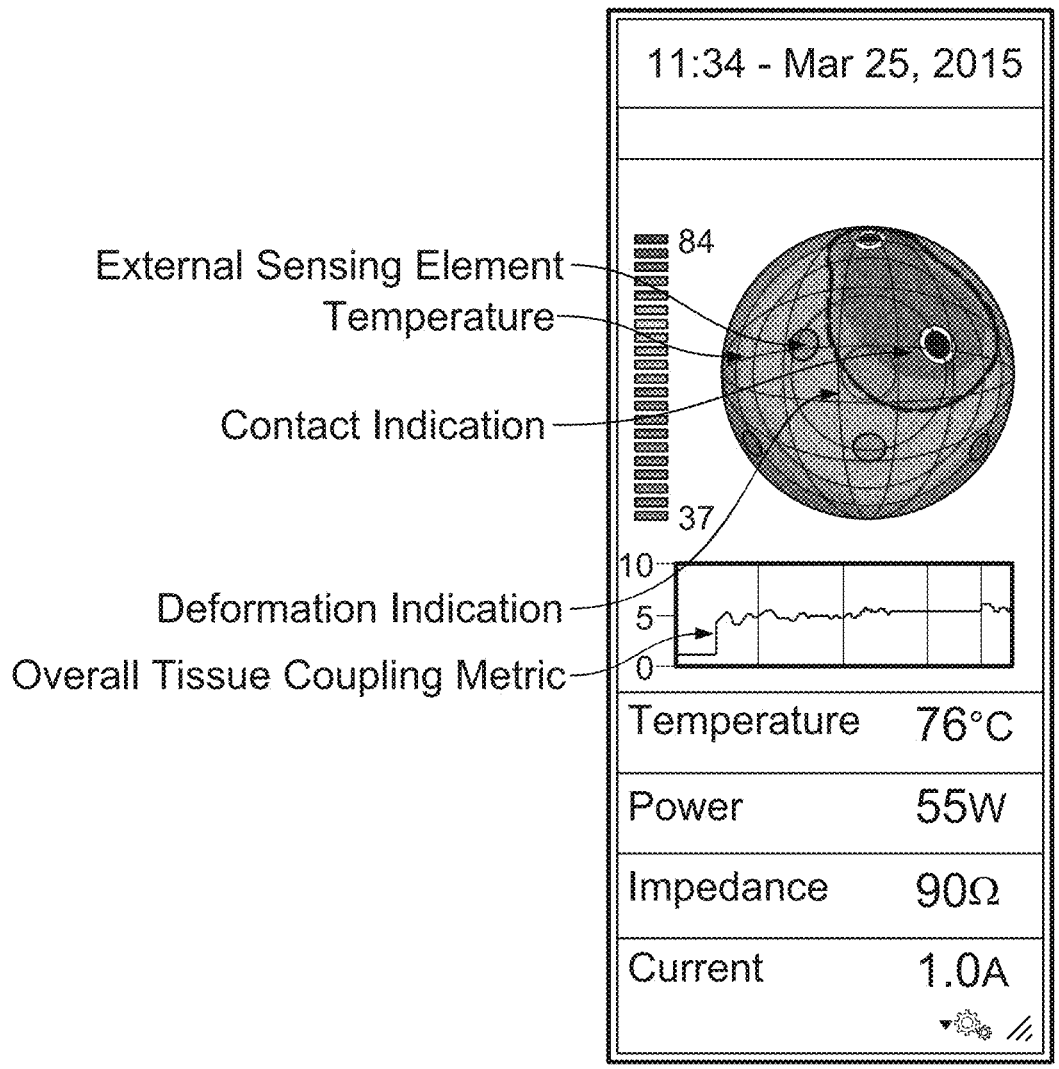
FIGS. 9 and 10 are examples of screen shots of a monitor of the ablation system shown in FIG. 1 during treatment.
Figure 10:
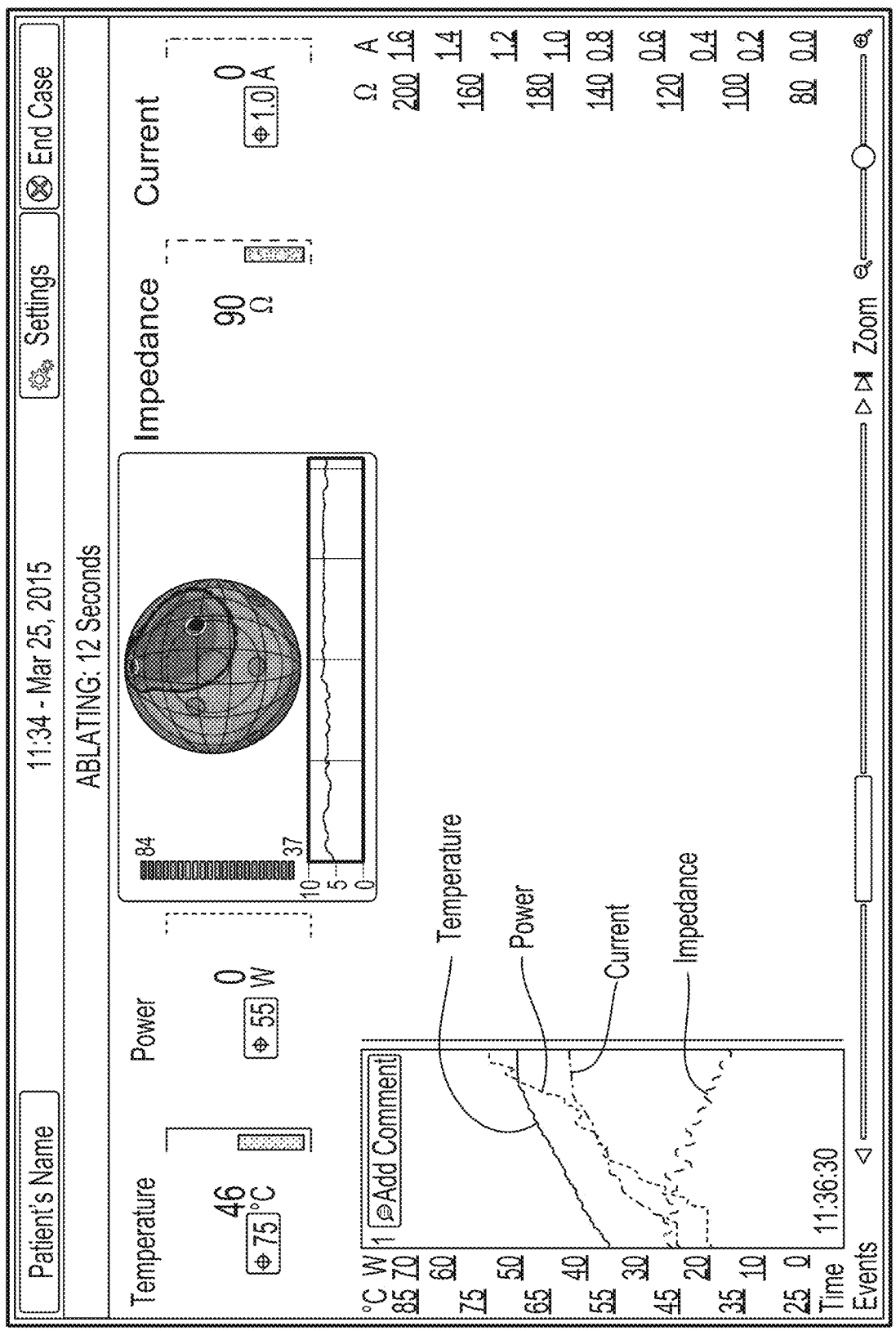

FIGS. 9 and 10 are examples of screen shots from the monitor of the ablation system during an ablation treatment. Referring first to FIG. 9, the monitor displays a graphic representation of the distal tip 122 with markings that represent the various electrodes of the distal tip 122. Two of those electrodes are surrounded by a marking (e.g., an annular ring of a different color than the displayed electrodes) that indicates those particular electrodes are in contact with tissue. In some implementations, for example, the electrodes are colored in black while the surrounding markings are colored in white. However, other color schemes and other types of graphical representations can alternatively or additionally be used. The remaining electrodes include no such surrounding marking, thereby indicating that those electrodes are not in contact with tissue.

The various different regions of the distal tip 122 are displayed in different colors, depending on the detected temperatures of those regions. In some implementations, for example, the warmest detected temperature regions are displayed in red, the coolest detected temperature regions are displayed in blue, and regions of intermediate temperatures are displayed as some relative combination of red and blue or as other colors, such as green and yellow. This graphical representation of the temperature of the distal tip 122 can also serve as a tool to determine which portions of the distal tip 122 are in contact with tissue as the portions of the distal tip 122 in contact with the tissue will allow saline (and thus electrical energy) to flow through open valves to the tissue, thereby resulting in elevated temperatures.

A vertical temperature scale is provided to the left of the graphical representation of the distal tip 122 in FIG. 9. In this case, the maximum detected temperature (or a rounded temperature value near the maximum detected temperature) is provided at the top of the scale and the minimum detected temperature (or a rounded temperature value near the minimum detected temperature) is provided at the bottom of the scale. The scale includes multiple different hash marks along its length that are visually distinguishable from one another. Typically, for example, the hash marks are different colors that correspond to the various displayed colors on the graphical representation of the distal tip 122. By looking at the maximum and minimum temperatures of the scale, the user can readily determine or estimate the temperature associated with each of the different hash marks along the scale. In this way, the user can use the scale to determine or estimate the temperature of tissue or other environment adjacent the various different regions of the distal tip 122.

In addition to the color gradient describes above, a deformed region of the distal tip 122 (e.g., the region of the distal tip 122 that is in contact with tissue) is demarcated by a dashed line. This can further help the user to visualize the area of tissue contact and thus the area of the lesion being formed.

In some implementations, the valves of the distal tip 122 are displayed at appropriate locations on the distal tip 122. In such implementations, the valves that are determined to be open can be displayed differently than the valves determined to be closed. For example, the open valves can be displayed in one color while the closed valves are displayed in a different color. Alternatively, the valves can be displayed in a way that represents the way the valves actually look in their closed and open positions.

As shown in FIG. 9, a graph is provided beneath the graphical representation of the distal tip 122 for showing a tissue coupling metric over time. The tissue coupling metric value at any given time can, for example, be determined by determining values of the various outer electrodes. In this case, the electrodes that are determined to be in contact with tissue are assigned a value of 10, while the electrodes that are not in contact with tissue are assigned a value of 0. The average value across the various outer electrodes can then be determined and displayed as the tissue coupling metric over time. This value can provide the user with an indication of the degree of contact between the distal tip 122 and the patient's tissue. In some implementations, the control unit of the system is also configured to disable ablation until the tissue coupling metric reaches or exceeds a predetermined minimum value that indicates sufficient contact between the distal tip 122 and the patient's tissue. The predetermined minimum value can, for example, be 4 on the scale of 0 to 10.

Still referring to FIG. 9, the maximum temperature across the different sensors, power, impedance, and current associated with the ablation system is also displayed beneath the graphical representation of the distal tip 122.

FIG. 10 shows an alternative arrangement for the display of the ablation system. This screen displays much of the same information displayed in the screen shot of FIG. 9. However, rather than being arranged vertically along the screen, that information is displayed horizontally along a top region of the screen. A status bar above that data indicates the status of the ablation system. In this example, the status bar indicates that the system has been performing ablation for 12 seconds. The display illustrated in FIG. 10 also includes a graph that shows the progression of the detected temperature, power, impedance, and current over time.

An image representing the shape of the distal tip 122 and characteristics of the lesion during treatment can also be displayed on the monitor. The physician can use this information to confirm that the distal tip 122 remains in proper contact with the tissue throughout the treatment. The physician can, for example, use this information to help ensure that the distal tip 122 is deformed (e.g., by an amount equal to at least ¼ to ½ of its diameter in its undeformed state) throughout the treatment. The depiction of temperature within the treated tissue (e.g., by the use of a color gradient representing a range of temperatures or some other graphic representation of temperature) can also help the physician to understand the area and depth of the tissue that is being ablated.

In some implementations, the image or video displayed on the display 110 depicts the regions of the tissue according to their temperature using an isothermal map. For example, darker regions of the image can represent hotter tissue regions, while lighter regions represent cooler tissue regions. Alternatively, different colors can be used to represent the different tissue temperatures. For example, red regions of the image can represent hotter tissue regions, while blue regions of the image represent cooler tissue regions. The physician can use this information to better understand the size, particularly the depth, of the lesion being created. Thus, this can help to ensure that lesions of a desired depth are generated during the treatment. When data from the sensors of the ablation catheter 104 are combined with data collected form the recording/mapping system, these graphical representations of the distal tip 122 and the tissue being ablated can further ensure that desired levels of energy are reaching the specific regions of tissue intended to be ablated. This can be particularly beneficial when the region of tissue to be ablated is thick.

Since the area of contact with the endocardium is actively cooled with irrigation, permanent lesions can sometimes not form on the endocardium. This effect is referred to as endocardial sparing and is undesirable when applying a permanent ablation lesion. The following describes a titration of power and flow in order to maximize lesion size and avoid endocardial sparing. In the first phase, lasting approximately 30 s, high (e.g. 15-30 mL/min) flow could be used with a lower power setting (e.g. 20 W). This phase helps heat the immediate endocardial tissue, reducing its impedance, thus allowing deeper penetration of power in the second phase. Once heating and impedance drop is accomplished, a second phase, lasting approximately 30 s, with the same flow and higher power (e.g. 40 W) can be applied. In this phase the highest power and the most energy is delivered, making this phase primarily responsible for the lesion's eventual depth. Subsequently, a third phase targets endocardial tissue lasting approximately 30 s, where both power and flow are lowered (5-10 mL/min and 20 W) is entered. Due to the lower flow, the endocardium receives less cooling and is more likely to be included in the permanent lesion. In order to avoid steam pop and char formation, power is also lowered in this phase. The transition between the phases can be done suddenly (e.g. in a single step) or gradual (e.g. over a short period of time). This sequence in its entirety can be programmed in advance into the ablation generator, or catheter interface unit and implemented by the system. Alternatively, this sequence can be manually implemented by hospital staff as the lesion is delivered. While specific time periods, power settings, and flow settings have been described for the ablation phases, others could be used.

While certain implementations have been described above, other implementations are possible. For example, while the thermistors of the distal tip 122 have been described as being attached to portions of the flexible printed circuit 154 opposite the central conductive components 150 of the various outer electrodes 146, the thermistors can alternatively or additionally be attached to portions of the flexible printed circuit 154 opposite the annular conductive components 152 of the outer electrodes 146. The thermistors can alternatively be directly connected to one of the conductive components 150, 152 of the outer electrodes 146 (e.g., via openings formed in the flexible printed circuit 154).

In addition, while the outer and inner electrodes 146, 148 and, in some cases, the thermistors have been described as being attached to discrete flexible circuit pads, in certain implementations, the outer and inner electrodes 146, 148 and the thermistors are attached to flexible printed circuit strips that extend from the catheter shaft along the distal tip. These strips could themselves be discrete elements, or branches of a single flexible circuit.

Various forms of thermistor and thermocouples can be implemented. For example, rather than discrete components, these can be applied to the flexible printed circuit as thin film or ink applied as part of the flexible printed circuit manufacturing process. Furthermore, rather than on the flexible printed circuit, these elements can be applied directly to the distal tip. For example, the thermistors and thermocouples could be formed directly using appropriate thermistive or conductive materials, e.g., conductive inks, on the distal tip.

While external electrodes have generally been described as circular and/or concentric, other shapes can be used and/or relative locations can be used. For example, the electrodes could be oval or rectilinear, or positioned in close, but not concentric, proximity. In some examples, the external electrodes can be individual electrodes and/or individual parts (e.g., pieces of metal, assembled on the distal tip.)

While the ribs of the distal tip 122 have been described as being circumferentially offset from the slits, in certain implementations, the ribs are aligned with the slits.

Additionally, while the distal tip 122 has been described as including shape activated valves that include three slits formed in sidewalls that form a tetrahedral recess in the body of the distal tip, other types of shape activated valves can alternatively or additionally be used. For example, a greater number of slits (e.g., six slits) or a smaller number of slits (e.g., one slit or two slits) can be used to form the valves. In addition, the slit or slits can be formed in recesses having shapes different than the tetrahedral recesses described above. In some implementations, the slit or slits are formed in portions of the body of the distal tip that are not recessed at all. Several examples of distal tips that include different types of shape contact valves and that can be used on the ablation catheter 104 in place of the distal tip 122 described above will now be described.

Figure 12:
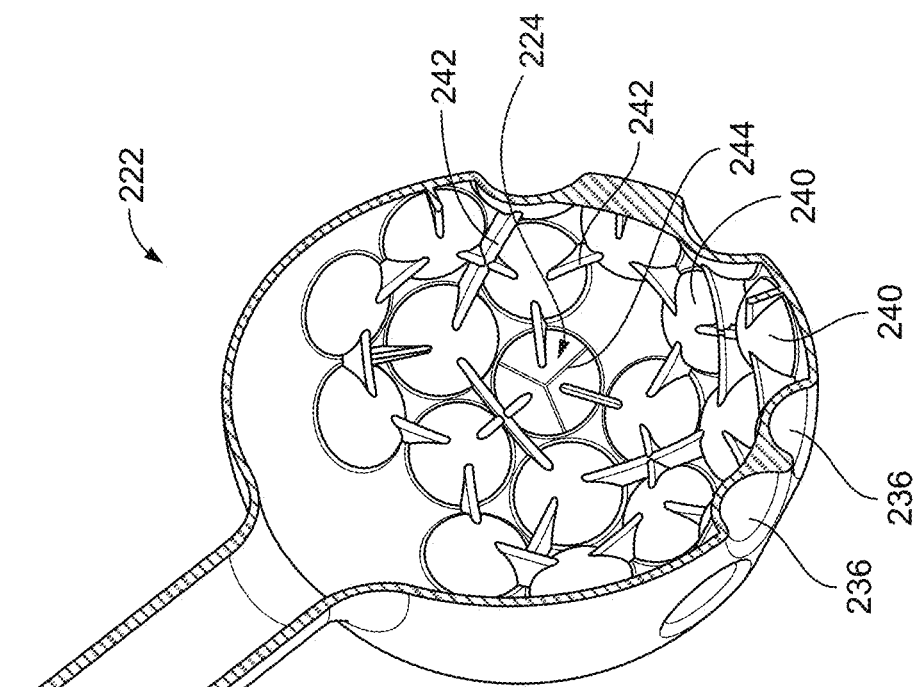
FIGS. 11 and 12 are perspective and cross-sectional views, respectively, of an alternative conformable tip, which includes hemispherical recessed regions.
Figure 11:
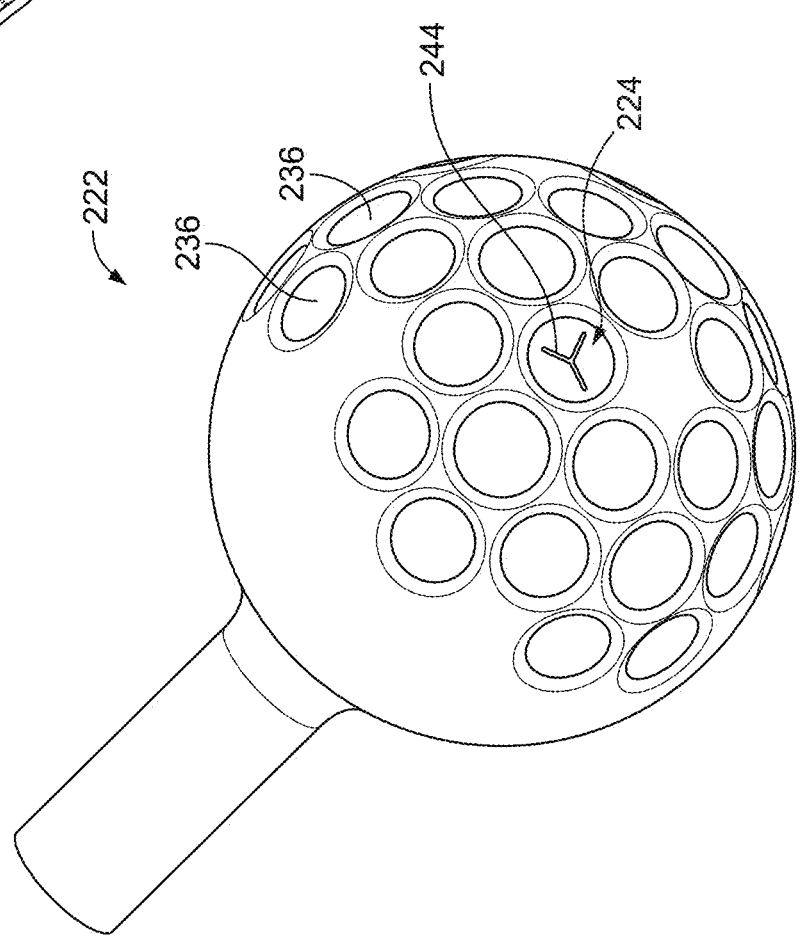

As shown in FIGS. 11 and 12, a distal tip 222 includes hemispherical dimples or recesses 236. For simplicity, only one of the recesses 236 in these figures is illustrated as including slits 244 for forming shape activated valves 224. However, it should be understood that each of the recesses 236 would typically include slits for forming shape activated valves. The recesses 236 include three slits 244 that extend outwardly from a center point in much the same way as the slits 144 of the distal tip 122 discussed above. The slits 244 are circumferentially spaced apart from one another by about 120 degrees. As shown in FIG. 12, ribs 242 extend between the inwardly extending hemispherical projections 240 of the distal tip 222. The ribs 242 are circumferentially spaced apart from one another by about 120 degrees and are circumferentially spaced from the nearest slits 244 by about 60 degrees. In much the same way as the ribs 142 described above with respect to the distal tip 122, the ribs 242 help to provide the valve walls with sufficient rigidity to maintain their shape during local deformations, resulting in valve opening. Any of the various manufacturing techniques described above with respect to the distal tip 122 can be used to form the distal tip 222.

While the distal tips discussed above have ribs that extend inwardly from the inner surfaces of those distal tips, the distal tips can alternatively include no such ribs. As an example, the distal tip 222 illustrated in FIGS. 11 and 12 can alternatively be formed without ribs. In some implementations, this version of the distal tip is molded with hemispherical projections that extend outwardly from the outer surface of the distal tip. After forming slits in those outwardly extending projections, the distal tip can be inverted (i.e., turned inside out). By inverting the distal tip in this way, the inner surface of the resulting inverted distal tip will be in compression since its internal circumference will be slightly smaller than its initial outer circumferences when it formed for the outer surface of the pre-inverted tip. This compression can function to bias the valves to a closed position, making it less likely that liquid will leak through the closed valves during use.

Figure 14:
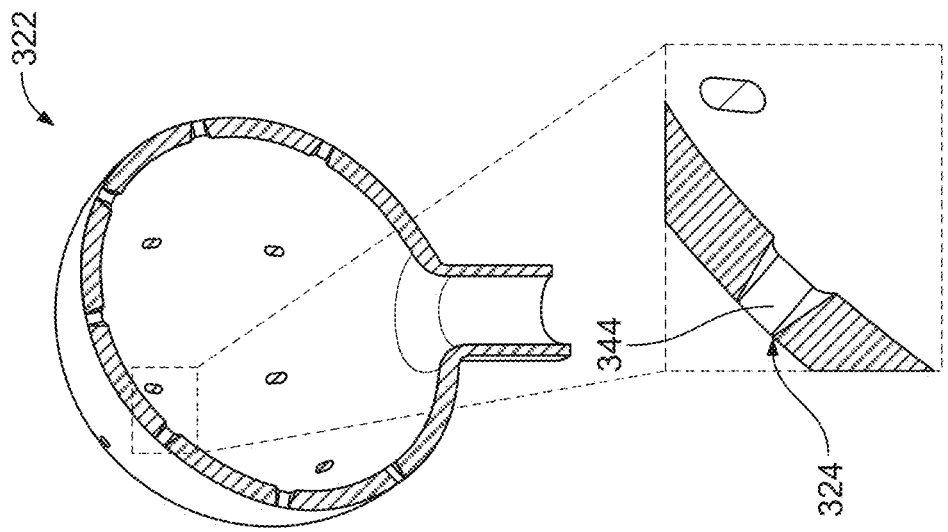
FIGS. 13 and 14 are perspective and cross-sectional views, respectively, of a conformable tip, which includes inwardly flared slits.
Figure 13:
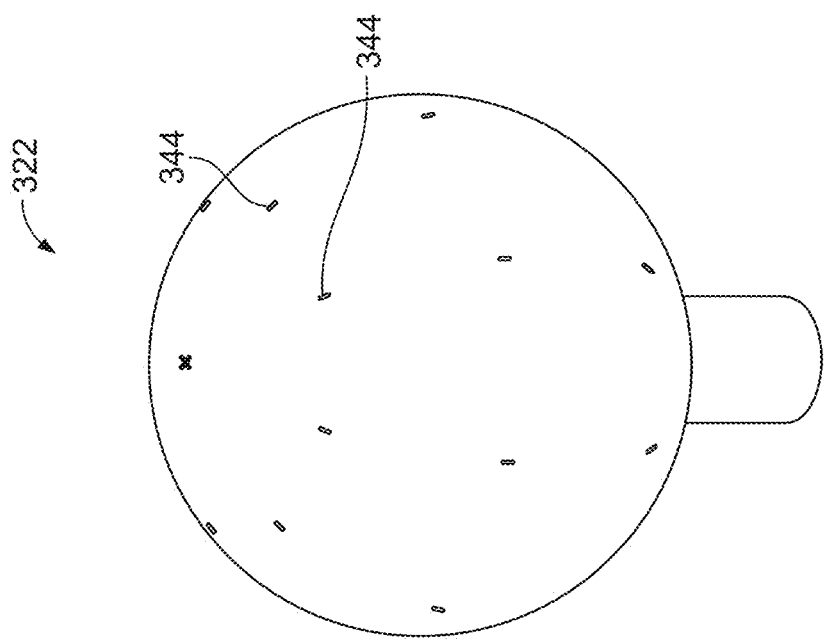

In addition, while each of the distal tips described above include recesses that extend inwardly from the outer surface of those distal tips, the distal tips can alternatively include no such recesses. As shown in FIGS. 13 and 14, for example, a distal tip 322, which includes a slightly thicker wall than some of the distal tips discussed above, includes smooth inner and outer surfaces with slits 344 extending therethrough. The wall thickness of the spherical body portion of the distal tip can range from 0.15 mm to 1.5 mm. As showed in FIG. 14, the slits 344 flare inward from the inner surface towards the outer surface of the distal tip, as manufactured. Prior to attaching the distal tip 322 to the ablation catheter shaft 128, the distal tip can be inverted (i.e., turned inside out). Due to the slight change in circumference of the surface that initially forms the outer surface of the distal tip 322 and ultimately forms the inner surface of the inverted distal tip 322 used in the ablation catheter 104, the inner surface of the inverted distal tip 322 experiences compression forces that bias the valves 324 to a closed position. As discussed above, this helps to prevent liquid from leaking from the closed valves 324 during use.

Figure 15:
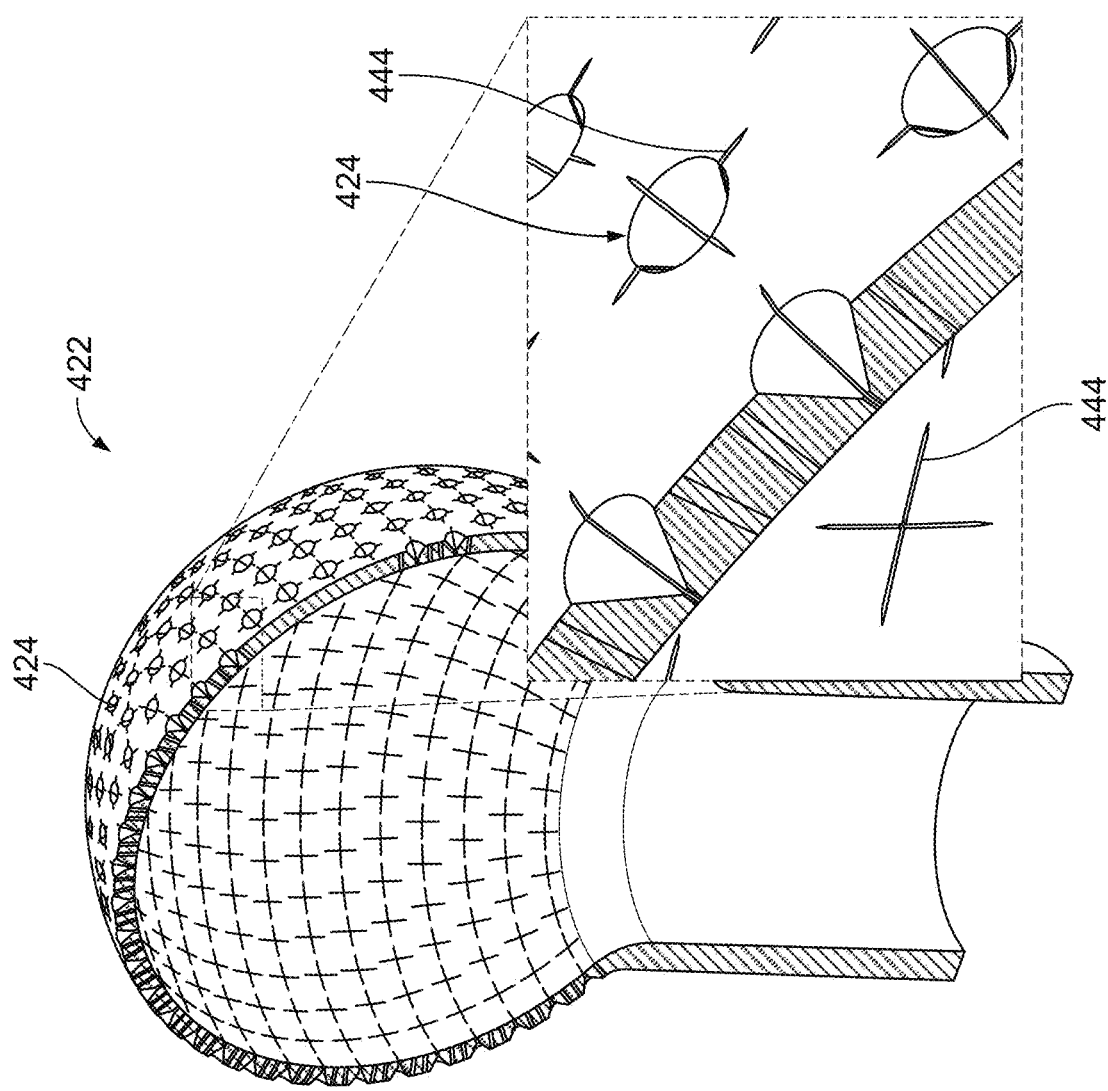
FIG. 15 is a cross-sectional view of a conformable tip, which includes cross-slits, relieved near their intersection on the external surface.

FIG. 15 illustrates a distal tip 422 that is similar to the distal tip 322 of FIGS. 13 and 14 in that a relatively thicker wall is utilized for valve function. Intersecting cross slits 444 are formed in the wall of the distal tip 422. The slits 444 cut through from the inner surface to the outer surface of the distal tip 422. The conical feature at the outer surface of the distal tip 422 is positioned to leave an open hole for fluid passage when a radially inward force is applied to the outer surface of the distal tip 422. For example, the radius of curvature of the outer surface will decrease, thereby placing the outer surface in compression. The material at outer edge of the cone will bear the compressive load of the outer surface during bending. At the same time, tension is created at the inner surface of the distal tip 422, causing the initially narrow slit regions (e.g., closed slit regions) to widen, thereby opening the valve 424. In other words, as the structure is locally pressed inward, the valves will pivot where the slits come together at the edge of the reliefs at the outer surface. The conical voids will ensure that a hole is open at the outer surface to allow fluid to pass as the slits at the inner surface spread apart.

Figure 16:
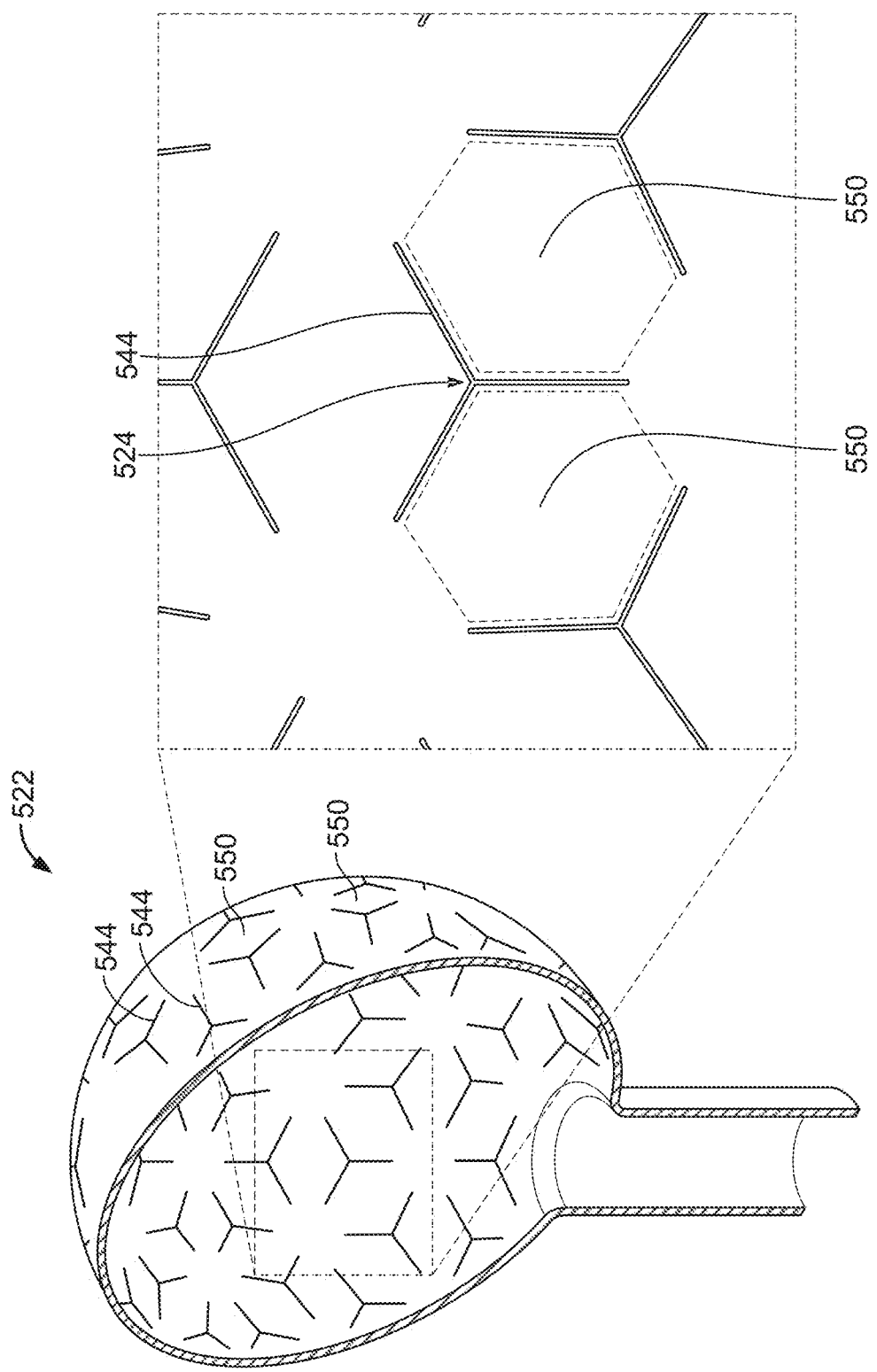
FIG. 16 is a cross-sectional view of a conformable tip, which includes three-legged slits.
Figure 17:
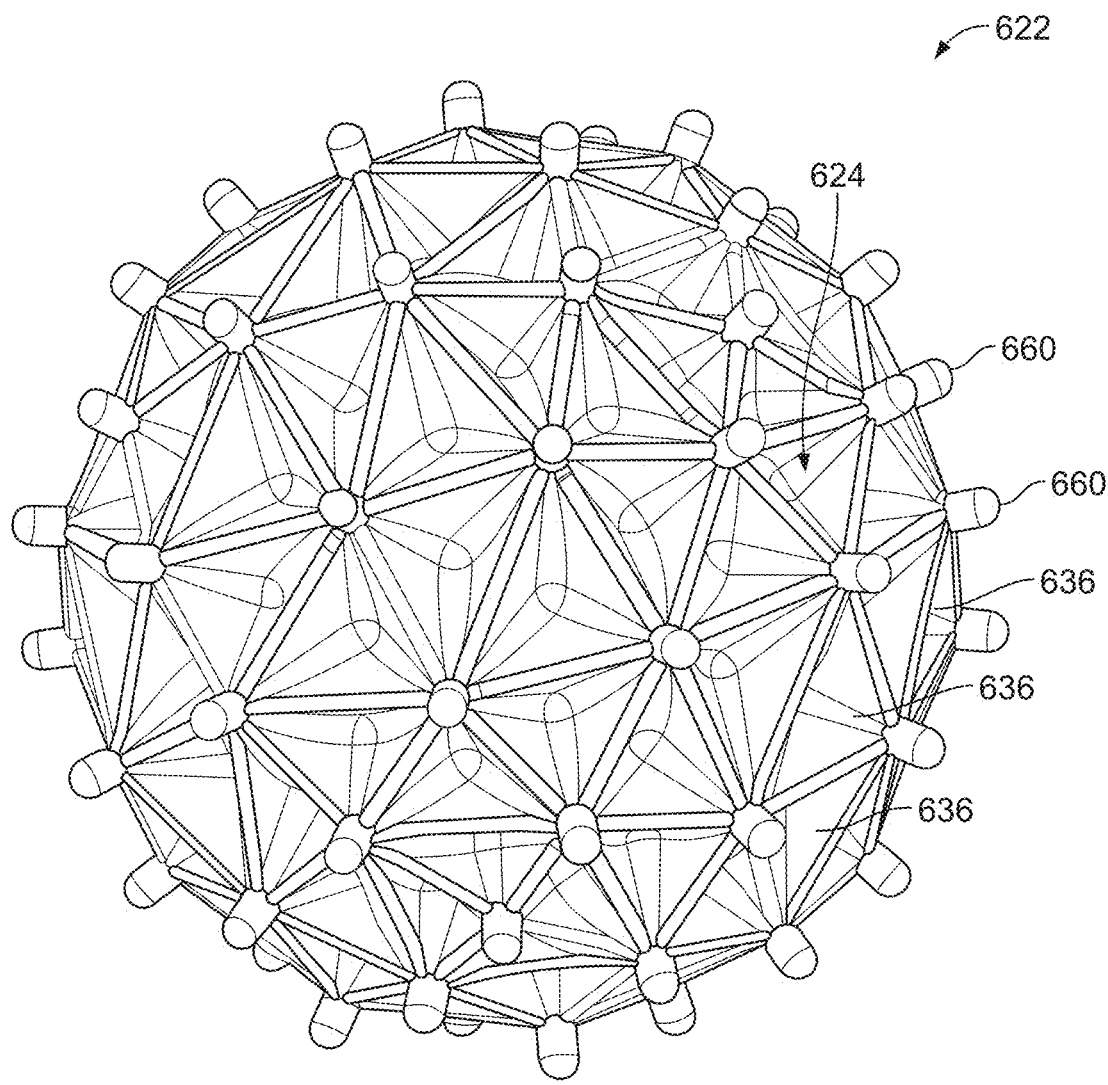
FIG. 17 is a perspective view of a conformable tip, which includes projections extending from its outer surface.

FIG. 16 illustrates another distal tip 522 similar to the distal tips 322 and 422 discussed above. The distal tip 522 includes smooth inner and outer surfaces, and the wall of the distal tip 522 includes multiple 3-legged slits 544 (also referred to as trifurcations) that form shape activated valves 524. The slits 544 within each of the slit groupings are circumferentially spaced from each other by about 120 degrees. The slit groupings are arranged in a manner such that hexagonal regions 550 that are free of slits are formed between many of the adjacent slit groupings. As radially inward forces are applied to the outer surface of the distal tip 522, these hexagonal regions 550 tend to remain in their baseline nominal curvature. However, neighboring hexagonal regions 550 will move relative to one other while retaining their nominal configurations. This relative movement of the neighboring planar regions 550 causes the valves 524 to open in response to deformation of the distal tip.

Although not shown in FIG. 16, the distal tip 522 can include projections that extend outwardly from the outer surface of the distal tip 522 in the hexagonal regions 550 between the groupings of slits 544. The projections can amplify the extent of displacement of the hexagonal regions 550 in response to a radially inward force applied to the outer surface of the distal tip 522. This can facilitate opening of the valves 524 in response to such forces.

Figure 39:
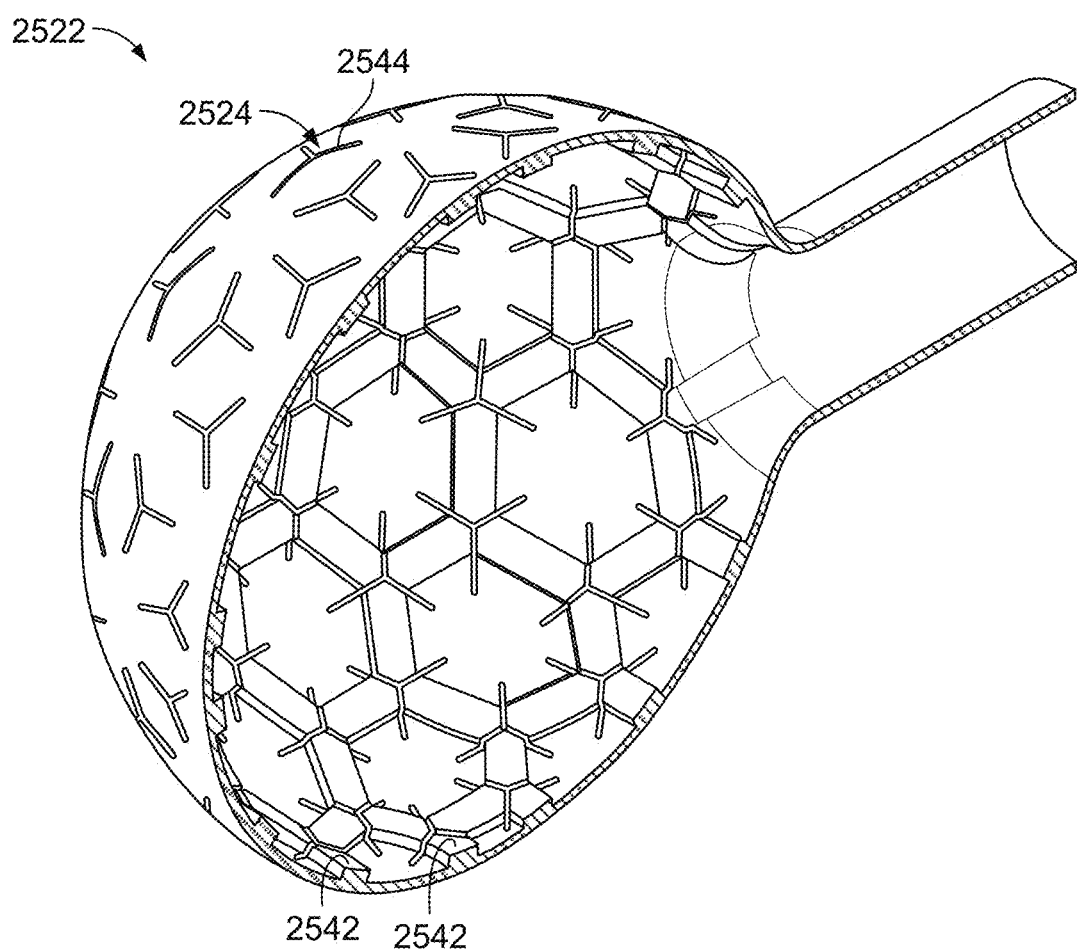
FIG. 39 is a cross-sectional view of a conformable tip, which includes three-legged slits and raised regions extending between slit groupings.

FIG. 39 illustrates a distal tip 2522 that is very similar in design to the distal tip 522 of FIG. 16. The distal tip 2522 includes a smooth outer surface, and the wall of the distal tip 2522 includes multiple 3-legged slits 2544 (also referred to as trifurcations) that form shape activated valves 2524. Unlike the distal tip 522 of FIG. 16, the distal tip 2522 includes raised regions 2542 that extend between intersection points of neighboring 3-legged slits 2544. The raised regions 2542 are hexagonal in shape and have a greater wall thickness than the other regions of the wall of the distal tip 2522. As a result, the raised regions 2542 provided greater stiffness to regions of the wall extending between neighboring 3-legged slits 2544. This construction helps to ensure that, as radially inward forces are applied to the outer surface of the distal tip 2522, the portions of the wall including the raised regions 2542 maintain their shape while moving relative to one other to open the valves 2524 formed by the 3-legged slits 2544. The distal tip 2522 can also include projections (not shown in FIG. 39) that extend outwardly from the outer surface of the distal tip 2522 in regions between the groupings of slits 2544 to allow for fluid communication between neighboring valves 2524. Although FIG. 39 shows the raised regions on the inside surface of the tip, the raised regions could be situated on the external surface to achieve similar effects.

Figure 40:
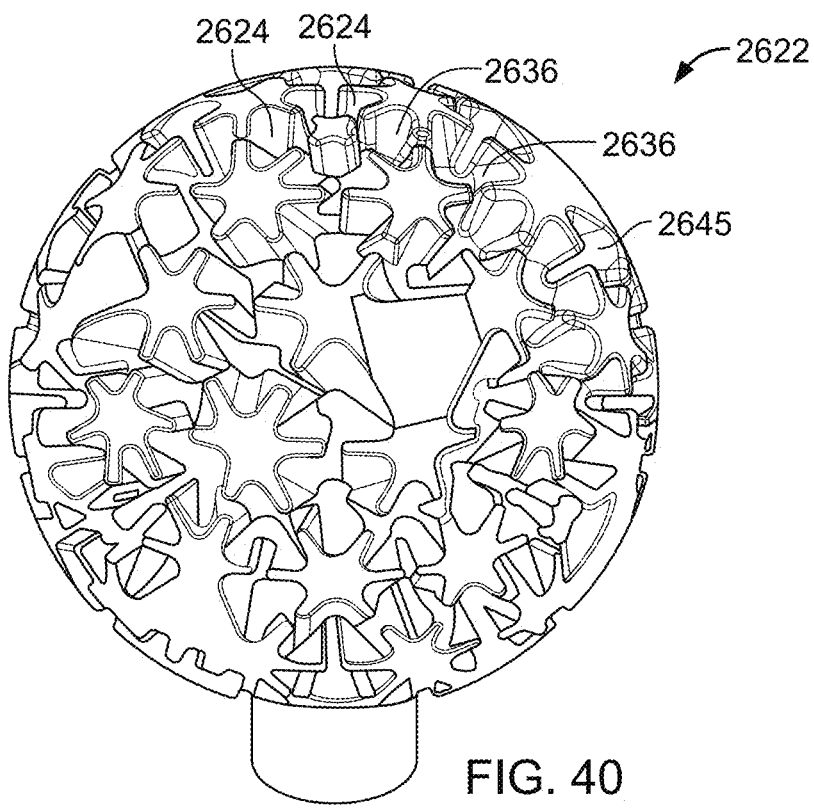
FIGS. 40 and 41 are perspective and cross-sectional views, respectively, of a conformable tip, which includes channels extending between recessed regions.
Figure 41:
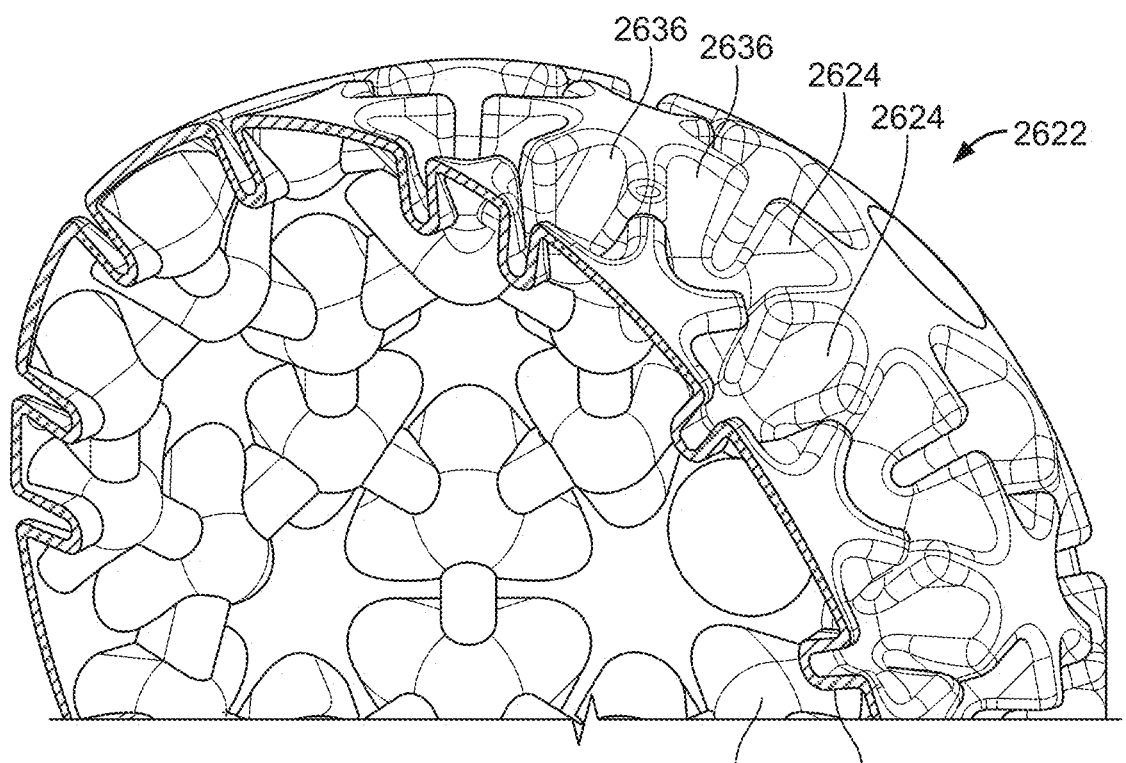

While certain distal tips described above, such as the distal tip 122 illustrated in FIGS. 2-5, include recessed regions and have generally smooth outer surfaces between the recessed regions, those smooth outer surfaces can alternatively be formed to define channels that permit fluid flow therethrough. These channels could have a U-profile (or V-profile) and replace the valve ribs, functionally. FIGS. 40 and 41 illustrate a distal tip 2622 that includes U-shaped projections 2642 that extend between valve recesses 2636 that have the same general configuration as the recesses 136 described above with respect to the distal tip 122 illustrated in FIG. 5. The projections 2642 operate in much the same way as the ribs 142 of the distal tip 122 described above. In particular, the projections 2642 provide added stiffness to the regions of the distal tip 2622 between the recesses 2636 and thus assist within opening of valves 2624 within those recesses 2636. Each of the projections 2642 includes opposing surfaces forming a channel 2645 with a U-shaped profile that extends between neighboring recesses 2636. This design can help to ensure that saline exiting open valves 2624 in the recesses 2636 is able to flow out of the distal tip 2622 and along the tissue by preventing the tissue from forming a complete seal with the outer surface regions surrounding the open valves 2624.

Furthermore, these channels 2645 can be advantageously used when having a conformal tip with holes rather than valves. In this scenario, irrigation holes are connected with a network of channels guaranteeing that fluid irrigation is still active in regions where the tip is pressed against tissue.

Other techniques can also be used to help prevent fluid stasis in the region of tissue contact. As show in FIG. 17, for example, a distal tip 622 has a very similar construction to the distal tip 122 discussed above. Unlike the distal tip 122, the distal tip 622 illustrated in FIG. 17 includes projections 660 that extend outwardly from regions of the outer surface between adjacent recessed regions 636. These projections 660 cause separation between the patient's tissue and portions of the outer surface of the distal tip 622 that surround the recessed regions 636, which form the shape activated valves 624. As a result, the projections 660 help to ensure that fluid is able to exit the open valves 624 and flow between the outer surface of the distal tip 622 and the patient's tissue as opposed to simply stagnating within the recessed regions 636 associated with the open valves 624. In addition, the projections 660 can amplify deformation of the valves 624 and thus facilitate opening of the valves 624 in regions of the distal tip 622 contacted by tissue. The projections 660 can also increase friction between the distal tip 622 and the patient, leading to improved mechanical stability and reduced movement of the catheter during ablation delivery.

Figure 18:
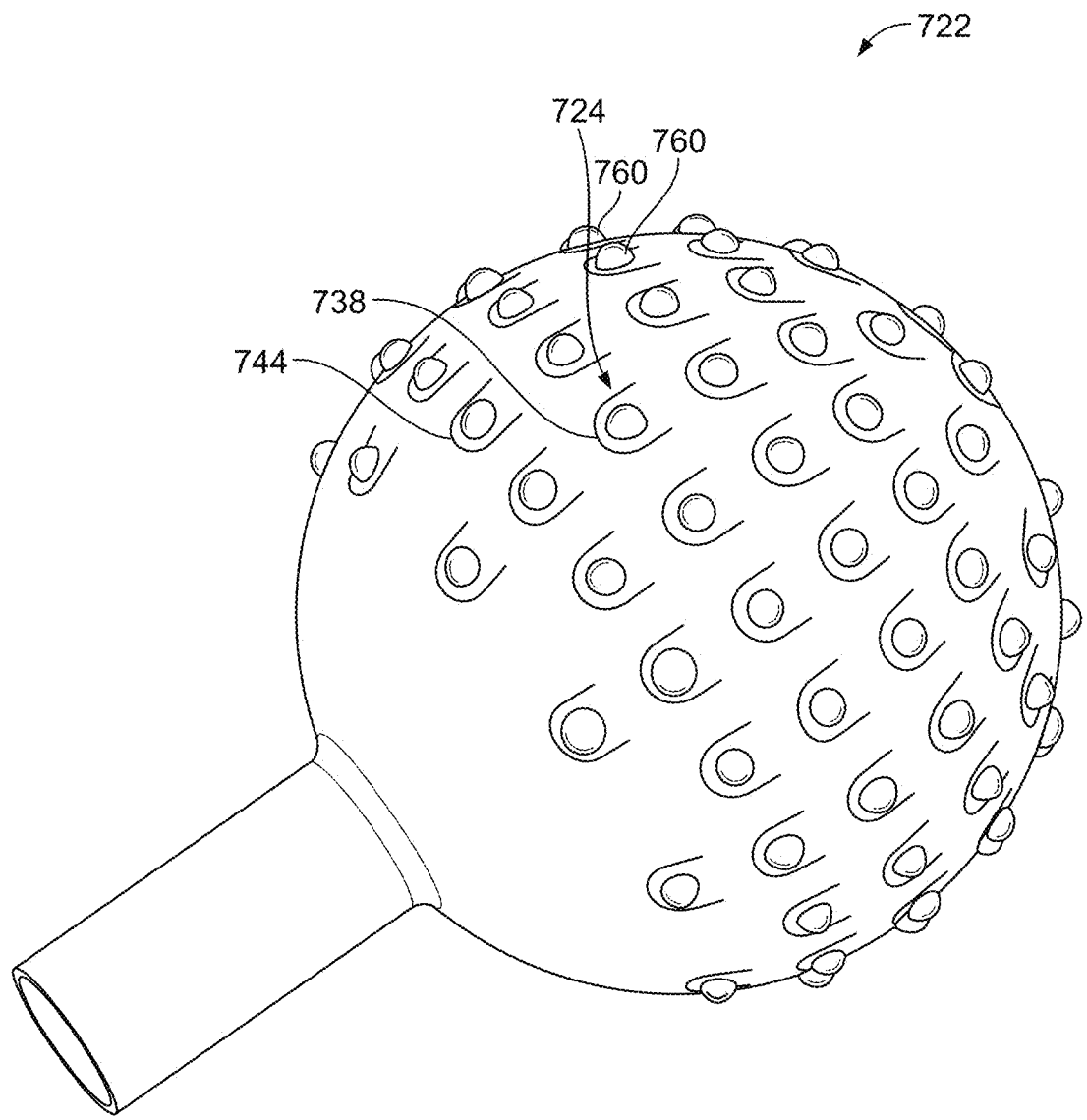
FIG. 18 is a perspective view of a conformable tip, which includes U-shaped slits forming valve flaps from which projections extend.

While the distal tips described above include generally linear slits, various other shaped slits and types of valves can be used. As shown in FIG. 18, for example, a distal tip 722 includes multiple U-shaped slits 744 that form flaps 738 that act as valves 724 around the distal tip 722. Projections 760 extend outwardly from the outer surfaces of the flaps 738. The projections 760 help to ensure that the flaps 738 move inwardly to a greater extent than neighboring flapless regions of the distal tip 722 when a radially inward force is applied to the outer surface of the distal tip 722. The projections 760, therefore, facilitate opening of the valves 724 in response to inwardly applied forces. The resiliency of the flaps 738 causes the flaps 738 to return to their original positions upon removal of the radially inward forces. Therefore, the valves 724 have the capability of reclosing if the user needs to reposition the distal tip 722 such that the contact points of the distal tip 722 change during use.

In order to help ensure that tissue adjacent the flaps 738 do not contact and create a seal with regions of the outer surface surrounding the valves 724, which can make it difficult for fluid to be distributed to other tissue regions, additional smaller projections (not shown) can extend from the flapless regions between neighboring valves 724. These smaller projections help to ensure that certain portions of the tissue remain spaced from the surface of the distal tip 722 such that fluid can flow between the tissue and the distal tip 722 rather than flowing elsewhere.

Figure 19:
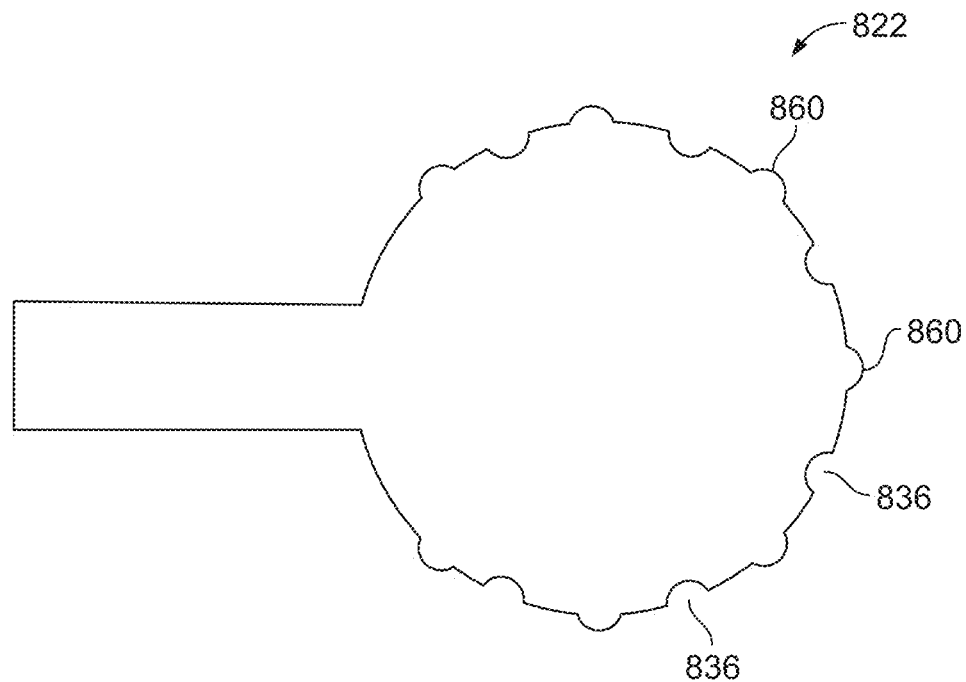
FIGS. 19 and 20 schematically illustrate a conformable tip, which includes projections and recessed regions including slits, in an undeformed configuration and in a deformed configuration, respectively.
Figure 20:
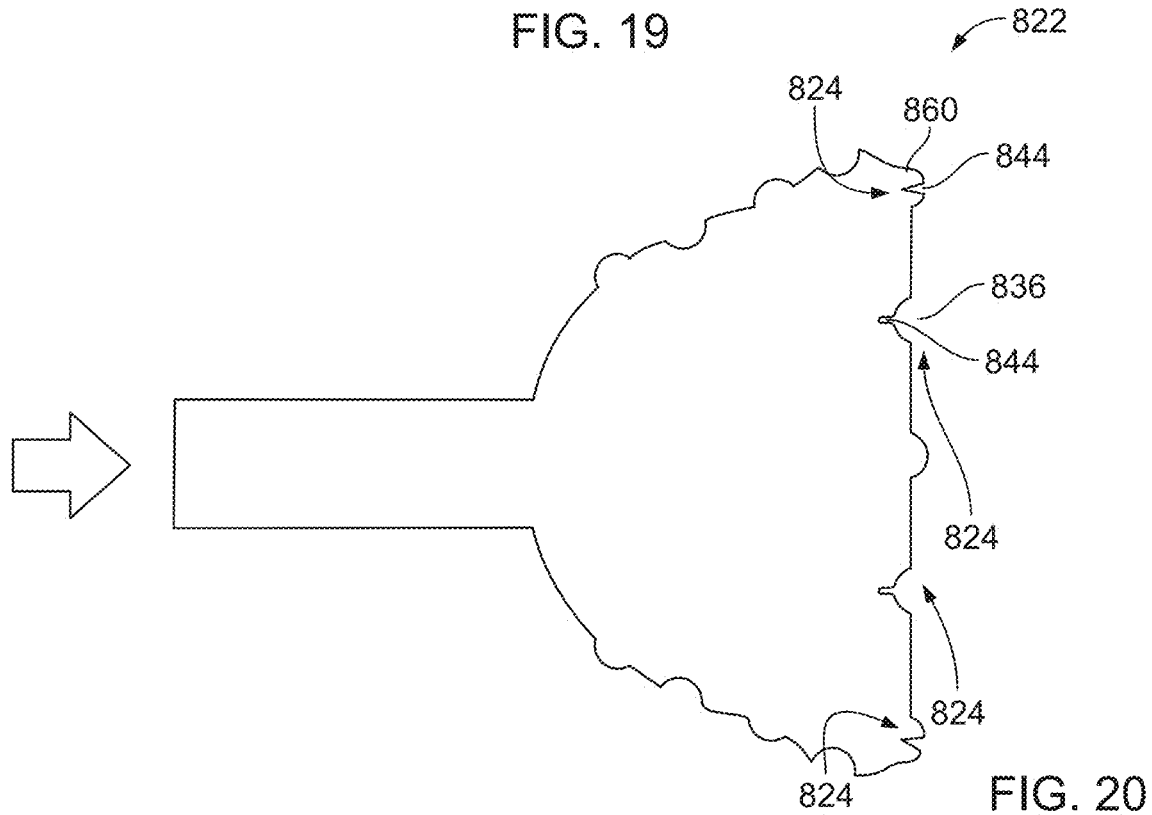

FIGS. 19 and 20 illustrate a distal tip 822 that includes hemispherical projections 860 that extend outwardly from the outer surface of the tip 822 and hemi-spherical recesses 836 that extend inwardly from the outer surface of the tip 822. Valves 824 are formed by slits 844 (shown in FIG. 20) that extend through the portions of the body forming the projections 860 and the recesses 836. The slits 844 in the recesses 836 operate in a manner similar to the slits 144 of the distal tip 122 described above. Specifically, as the wall of the distal tip 822 is deformed radially inward and forms a flat or concave shape, tension created at the inner surface of the distal tip 822 widens the slits 844 in the recesses 836, thereby opening those valves 824. In contrast, the projections 860 in those flattened or concave regions of the tip 822 tend to experience compressive forces, which cause the slits 844 to close tighter. Those valves 824 behave in the opposite manner when the tip 822 is deformed in a manner to take on a more convex shape. FIG. 20 shows the distal tip 822 being advanced distally into tissue such that a radially inward force is applied to a distal end region of the tip 822 by the tissue. As a result, the distal end region of the tip 822 has moved proximally and has become flat or concave in shape. The valves 824 of the recesses 836 in the flat or concave region have been opened due to tensile forces at the inner surface of the distal tip 822 widening those slits 844, while the valves 824 of the projections 860 in the flat or concave region have been closed due to compressive forces at the outer surface of the distal tip 822 narrowing those slits 844. At the same time, a circumferential region of the tip 822 at which the tip 822 transitions from its normal convex configuration to the deformed flat or concave configuration has taken on an even more convex shape than the original configuration. As a result, the valves 824 of the projections 860 in the circumferential region have been opened due to tensile forces at the outer surface of the distal tip 822 widening those slits 844, while the valves 824 of the recesses 836 in the circumferential region have been closed due to compressive forces at the inner surface of the distal tip 822 narrowing those slits 844. Thus, providing valves 824 in both the recessed regions 836 and the projections 860 of the distal tip 822 can help to ensure that saline is delivered via open valves 824 to all regions of the tissue that are in contact with or near contact with the distal tip 822.

Figure 21:
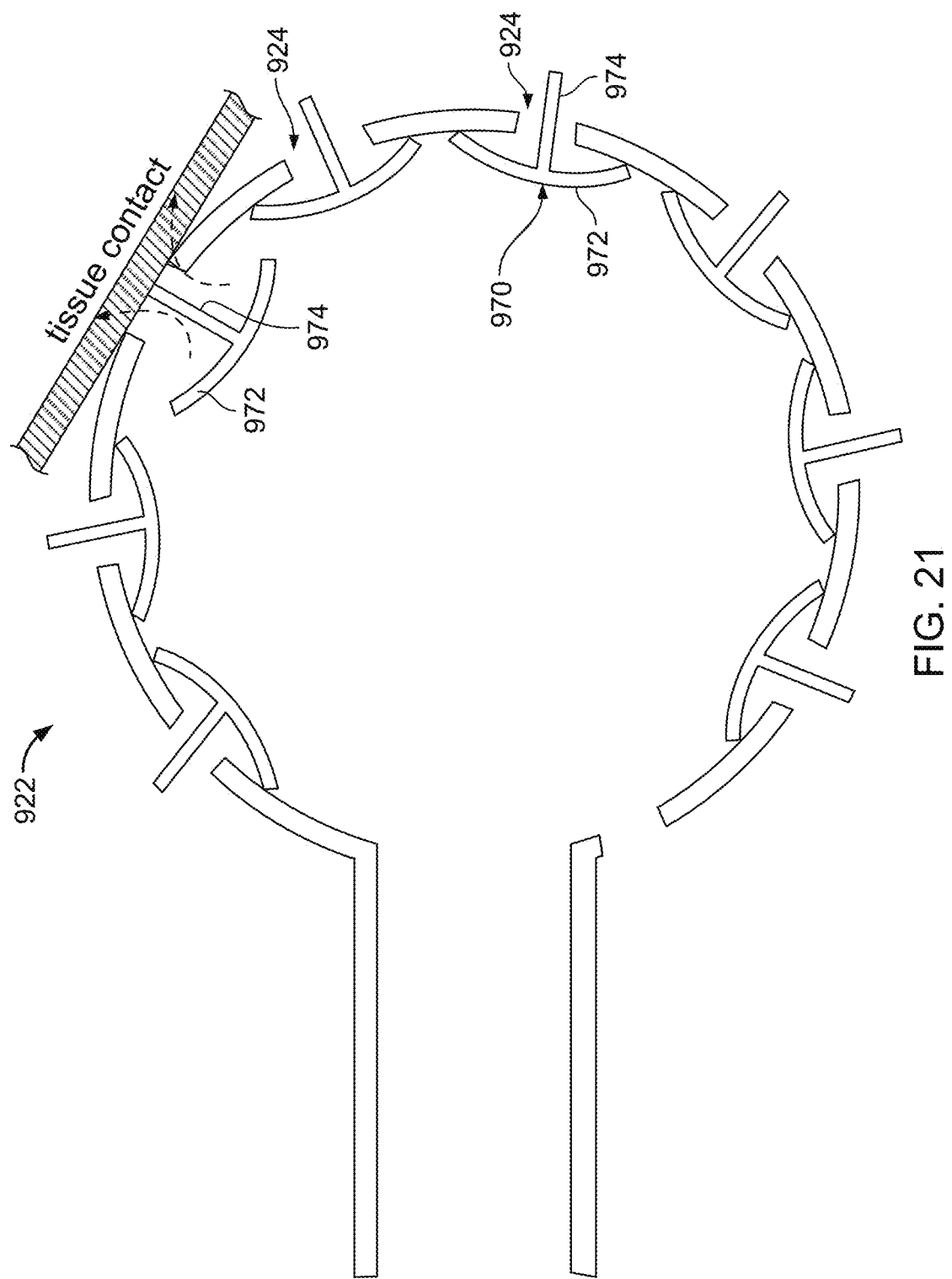
FIG. 21 is a schematic, cross-sectional illustration of a conformable tip, which includes umbrella valves.

In some implementations, additional force-activated structures can be positioned adjacent valve flaps of the distal tip to help prevent leaking from closed valves while permitting fluid to escape via opened valves. Referring to FIG. 21, for example, a distal tip 922 has multiple flap valves 924 formed in it side wall. The flap valves 924 can have constructions similar to the various valves described above. For example, the body of the distal tip 922 can include one or more slits that form valves that can be opened upon deformation of the distal tip 922. The distal tip 922 also includes an umbrella valve 970 associated with each of the flap valves 924 formed in the body of the distal tip 922. The umbrella valves 970 include a sealing portion 972 disposed inside the distal tip 922 and a projection 974 that is connected to the sealing portion 972 and extends outwardly from the outer surface of the distal tip 922. The umbrella valves 970 are displaceable with respect to the wall of the distal tip 922. The umbrella valves 970 are also biased to a position in which the sealing portion 972 is pressed against an inner surface of the distal tip 922 to hold the associated flap valve 924 in a closed position. They are biased in this way primarily by the elasticity of the material from which they are constructed in combination with internal pressure within the distal tip 922 resulting from irrigation. In some examples, they are also biased by a compliant, elastic member (not shown) that attaches the valve element to the tip. The elastic member could in some implementations be part of the tip, itself. Upon being contacted by tissue, as schematically shown in FIG. 21, the projection 974 and the sealing portion 972 of the umbrella valve 970 slide radially inwardly. As the sealing portion 972 moves away from the inner surface of the distal tip 922, the flap is free to also move radially inward to open the flap valve 924. The use of such umbrella valves 970 in combination with the flap valves 924 of the type discussed above can help to reduce (e.g., minimize) the amount of saline that is allowed to escape from the distal tip via closed flap valves 924 during a treatment.

While only the distal tip 122 has been explicitly described as having a structure that provides added support in the proximal region of the tip to prevent deformation of the proximal region of the tip in response to proximal forces applied to the distal region of the tip, it should be understood that each of the various other distal tips described herein can include a similar proximal support.

The various distal tips described herein can alternatively or additionally include various other types of proximal support structures that help to prevent the proximal region of the distal tip from deforming proximally due to a proximal force applied to the distal region of the tip or from excessive bending as a result of a lateral load. For example, as an alternative to or in addition to providing a thickened wall along the proximal end region of the distal tip, the proximal end region of the distal tip can be formed of a more rigid material than the distal region of the distal tip.

Figure 22:
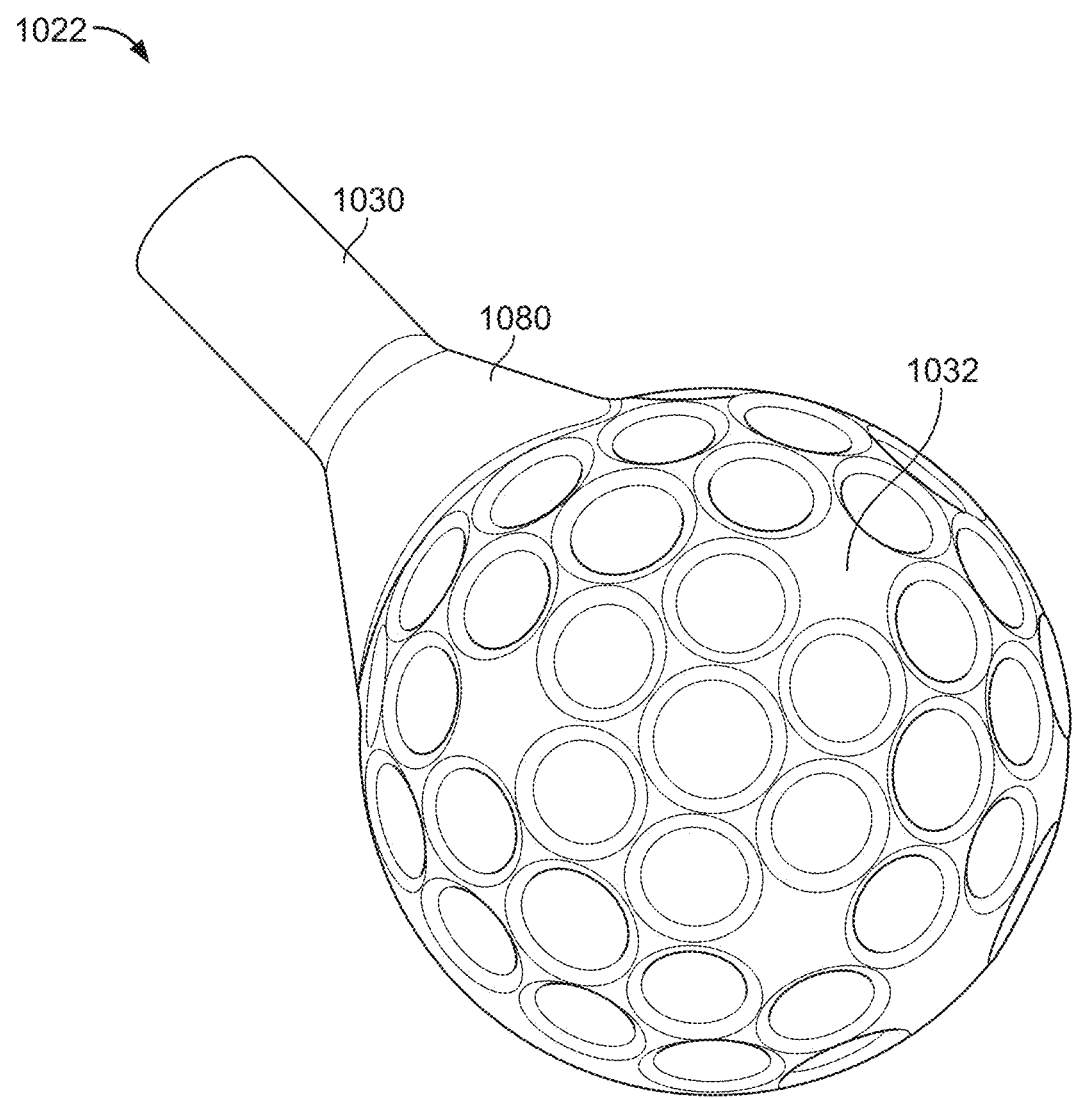
FIG. 22 is a perspective view of a conformable tip, which includes a conical support structure along its proximal end region.

FIG. 22 illustrates a distal tip 1022 that includes a conical support structure 1080 extending between a neck 1030 of the distal tip 1022 and a proximal end region of a spherical body 1032 of the distal tip 1022. The conical structure 1080 can be a solid structure that acts much like a thickened wall region of the distal tip 122 discussed above. Alternatively, the conical support structure 1080 can be a hollow member, which can reduce the total amount of material required to form the distal tip. In either case, the conical support structure 1080 can be either integrally formed with the neck 1030 and body 1032 of the distal tip 1022 or can be separately formed and then attached (e.g., thermally or adhesively bonded) to the neck 1030 and body 1032 of the distal tip 1022.

Figure 23:
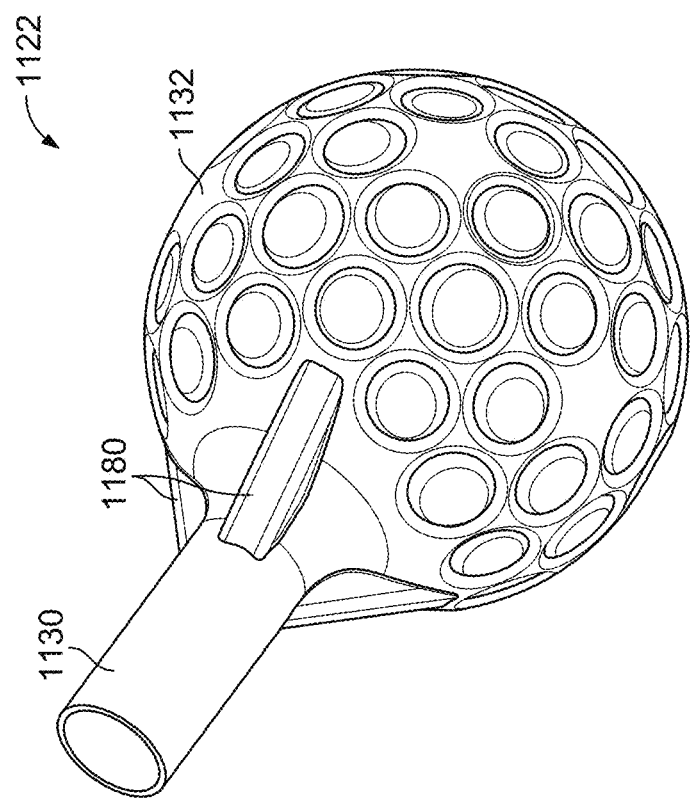

Other types of support structures can alternatively or additionally be used to limit deformation of the proximal end region of the distal tip. In certain implementations, for example, the proximal end region of the distal tip includes strengthening ribs. FIG. 23, for example, illustrates a distal tip 1122 including external support ribs 1180 that extend from a neck 1130 of the distal tip 1122 to a proximal end region of a spherical body 1132 of the distal tip 1122. The distal tip 1122 typically includes three or four support ribs 1180 that are equally spaced (e.g., spaced by about 120 degrees or about 90 degrees) about the circumference of the spherical body 1132 of the distal tip 1122. Although the support ribs 1180 are illustrated as solid members, they can alternatively be formed as hollow members to reduce the amount of material required to form the support ribs 1180.

Figure 24:
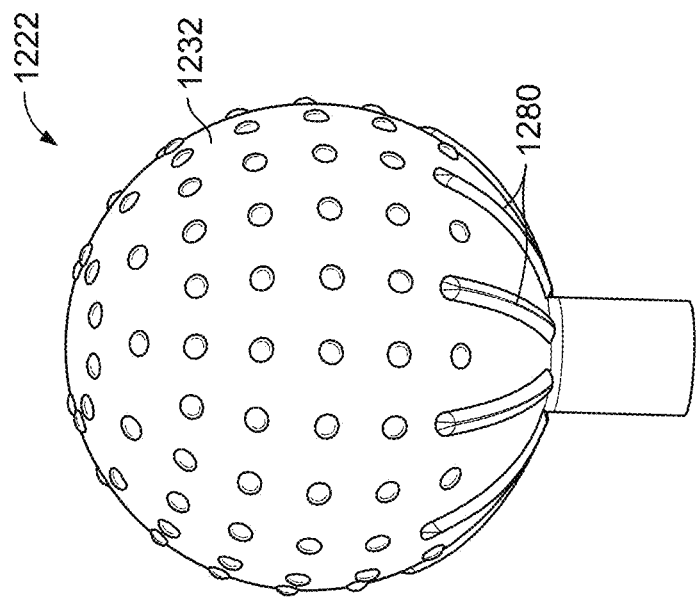
FIGS. 23 and 24 are perspective views of conformable tips that include rib structures extending along their proximal end regions.

FIG. 24 illustrates a distal tip 1222 that includes multiple ribs 1280 that extend along the outer surface of the proximal end region of a spherical body 1232 of the distal tip 1222. In certain implementations, the ribs 1280 are formed of the same material as the spherical body 1232 of the distal tip 1222. In such implementations, the increased thickness of that material in the regions including the ribs 1280 provide the proximal end region of the tip 1222 with increased rigidity. In other implementations, the ribs 1280 are formed of harder materials and are attached (e.g., thermally, adhesively bonded or molded) to the spherical body 1232 of the distal tip 1222. The use of harder materials to form the ribs 1280 can ensure that sufficient rigidity is imparted to the proximal end region of the distal tip 1222 while limiting the overall thickness of the proximal end region of the distal tip 1222.

Figure 25:
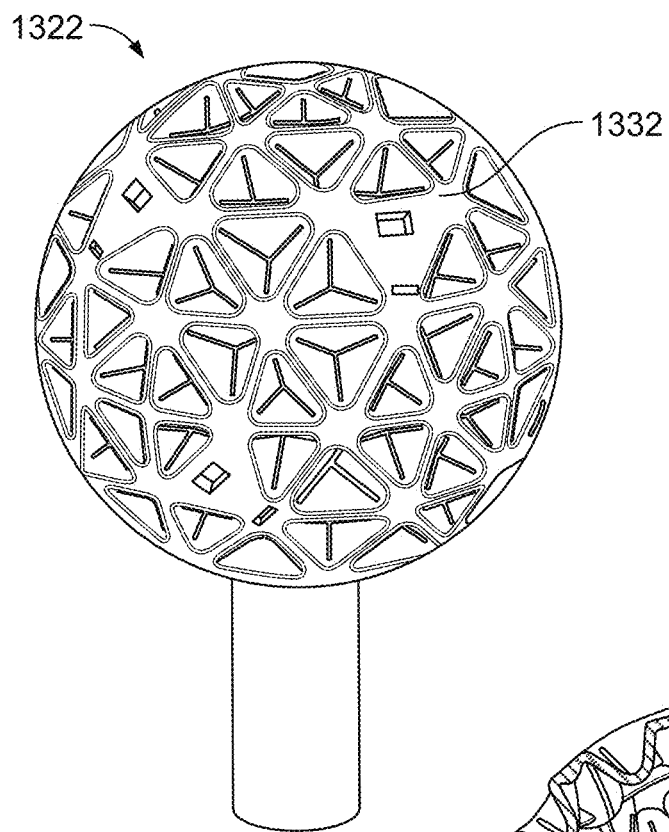
FIGS. 25 and 26 are perspective and cross-sectional views, respectively, of a conformable tip, which includes multiple ribs extending along its inner surface.
Figure 26:
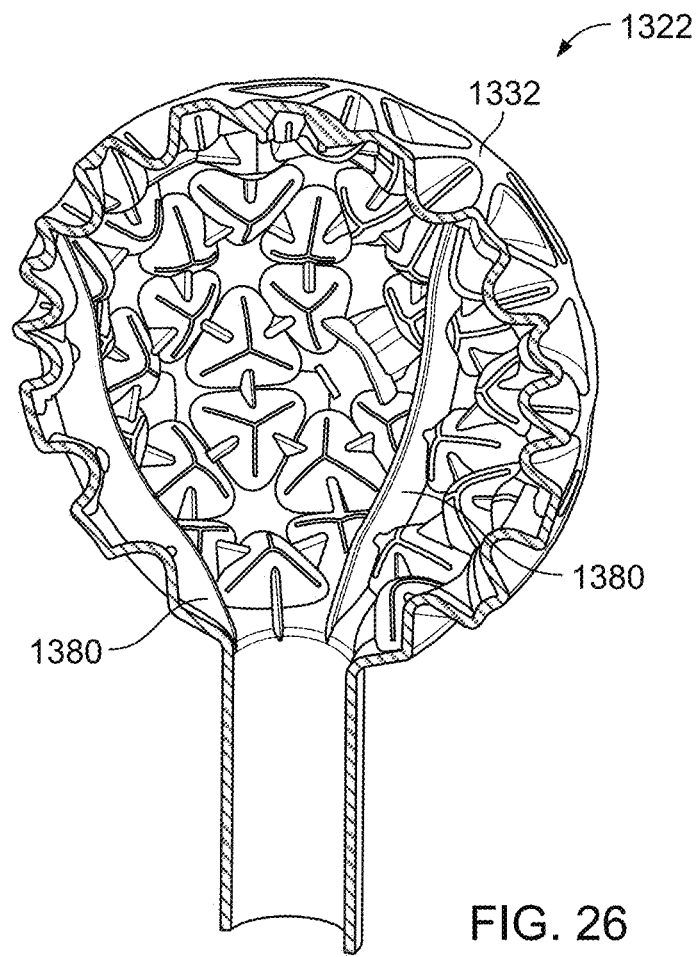

While the distal tips 1122, 1222 illustrated in FIGS. 23 and 24 include support ribs that extend along the outer surfaces of those tips, the support ribs can alternatively extend along the inner surfaces of the tips or can be embedded or encapsulated within the material of the distal tip. FIGS. 25 and 26, for example, illustrate perspective and cross-sectional views, respectively, of a distal tip 1322 including support ribs 1380 that extend from an inner surface of the distal tip 1322. These support ribs 1380 typically extend along ⅓ to ⅔ (e.g., ½) of the length of the distal tip 1322. The distal tip 1322 typically includes three or four support ribs that are equally spaced (e.g., spaced by about 120 degrees or about 90 degrees) about the circumference of a spherical body 1332 of the distal tip 1322. Because the ribs 1380 are positioned inside the distal tip 1322, the outer surface of the distal tip 1322 is free of projections, as shown in FIG. 25.

Figure 42:
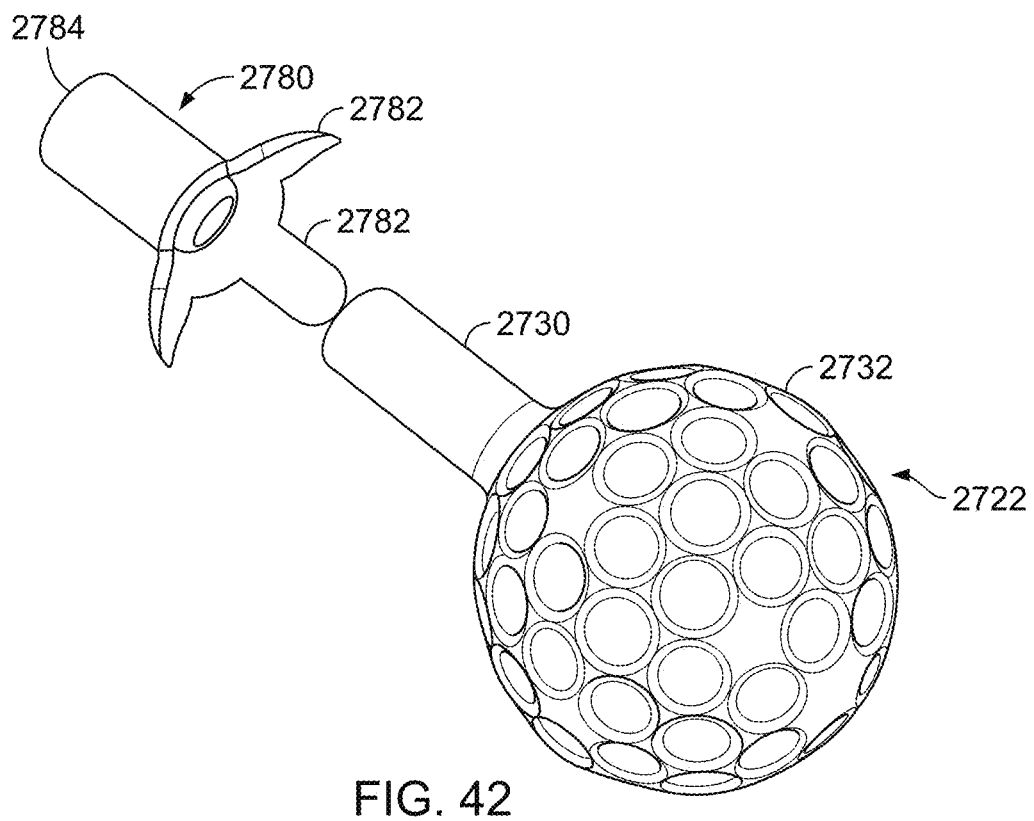
FIGS. 42 and 43 are perspective views of a distal tip and support structure assembly in a disassembled and assembled configuration, respectively.
Figure 43:
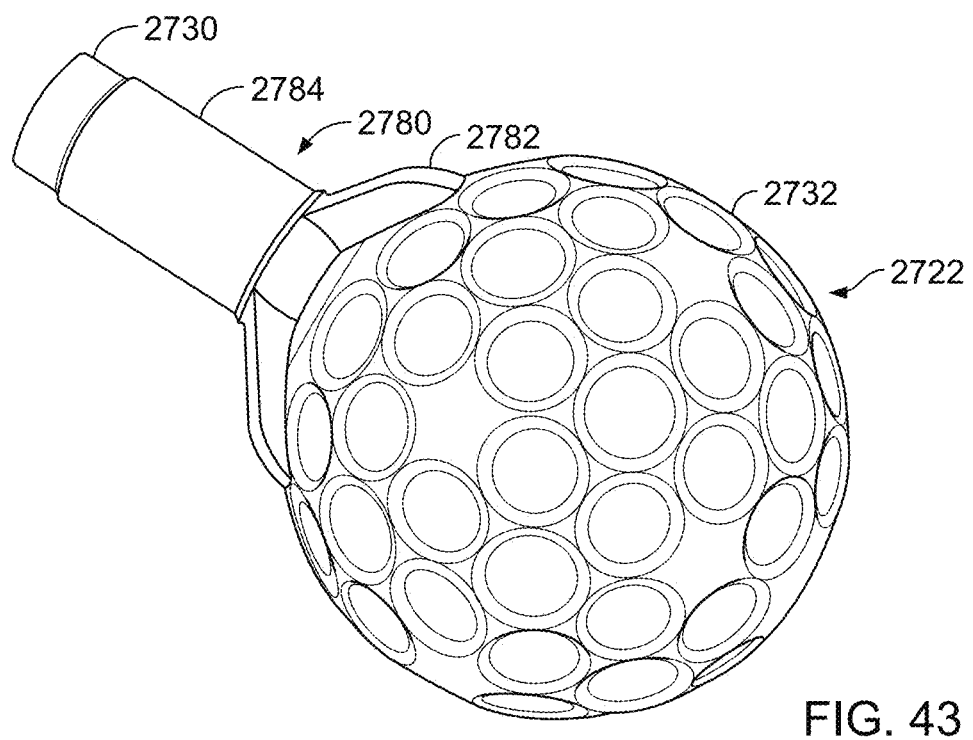

In some implementations, support structures are formed as separate components from the distal tips described herein and then attached to the distal tip to support desired regions of the tips. As shown in FIGS. 42 and 43, for example, a support structure 2780 is configured to fit over a neck 2730 of a distal tip 2722 to support a proximal end region of a spherical body 2732 of the distal tip 2722. The support structure 2780 includes multiple fingers 2782 that extend radially and distally from the distal end of a tubular member 2784. The support structure 2780 can be slid onto the neck 2730 of the distal tip 2722 and then attached to (e.g., thermally or adhesively bonded to) the neck 2730 and/or the spherical body 2732 of the distal tip 2722. Alternatively or additionally, the support structure 2780 can be attached to or axially fixed relative to the distal end region of the catheter shaft to which the distal tip 2722 is attached. The fingers 2782 and the tubular member 2784 of the support structure 2780 are more rigid than the wall of the distal tip 2722 and/or their combined stiffness with the wall when assembled is sufficient to prevent undesired deformation or deflection of the tip. The support structure 2780 can, for example, be formed of a harder material than the wall of the distal tip 2722 and/or can have a greater thickness than the wall of the distal tip 2722. Due to the rigidity of the support structure 2780, the support structure 2780 can help to prevent the proximal end region of the distal tip 2722 from deforming in response to a proximally applied force or a sideways force applied to the distal tip 2722.

Figure 27:
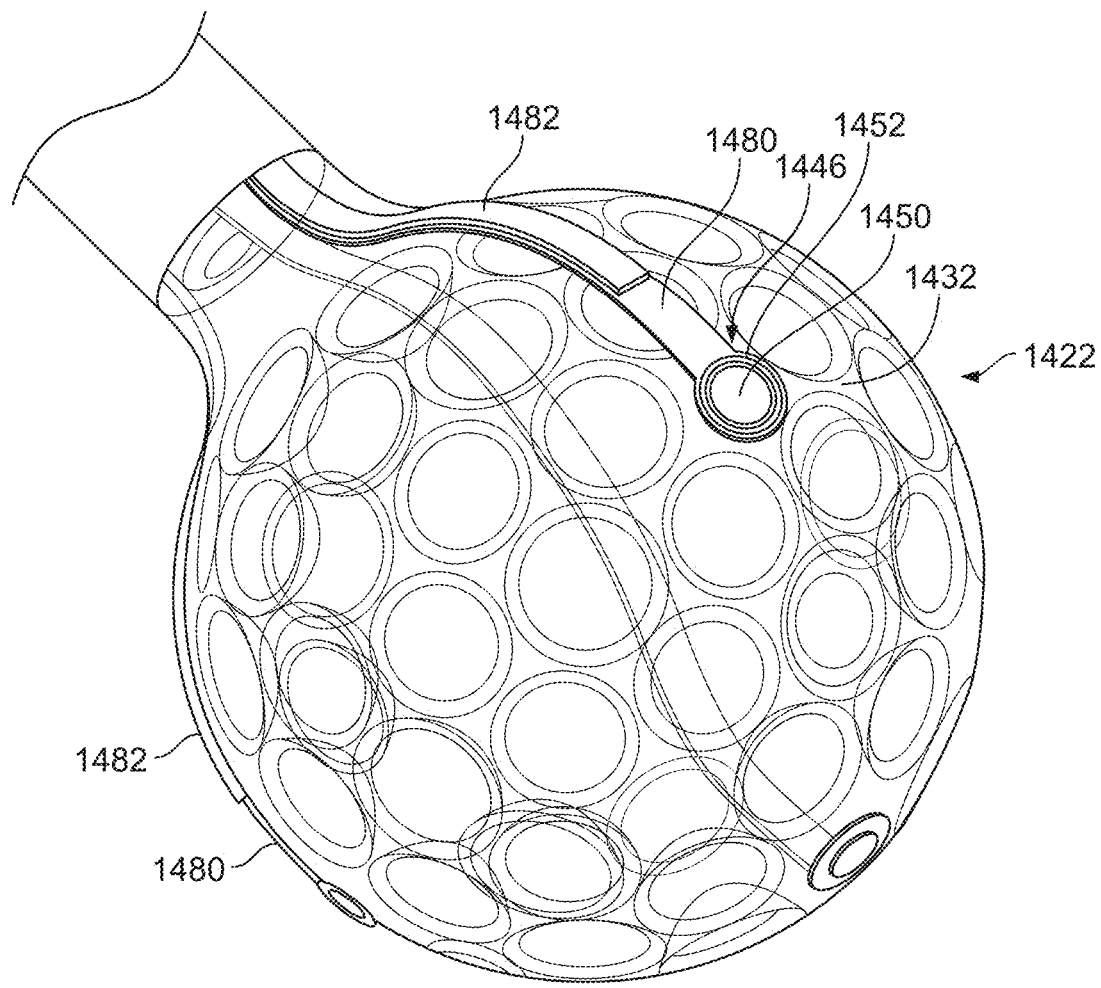
FIG. 27 is a perspective view of a conformable tip, which includes an alternative type of support structure extending along its proximal end region.

FIG. 27 illustrates a distal tip 1422 that includes three flexible printed circuit fingers 1480 that extend along and are attached to the outer surface of a spherical body 1432 of the distal tip 1422. Stiffening strips 1482 are attached to the outer surfaces of the flexible printed circuit fingers 1480 to provide structural support to the proximal end region of the tip 1422. The assemblies of the fingers 1480 and strips 1482 are approximately equally spaced (e.g., spaced by about 120 degrees) about the circumference of the spherical body 1432 of the distal tip 1422.

In some implementations, the stiffening strips 1482 are formed of a superelastic material, such as Nitinol, which can experience significant levels of strain without permanent deformation. As a result of this property, the stiffening strips 1482 formed of a superelastic material can be compressed while the distal tip is held in its collapsed configuration and then reliably return to their original curved shape as the distal tip is allowed to expand. Other materials from which the stiffening strips 1482 can be formed include metals (e.g., stainless steel) and polymers (e.g., polyimide or polyether ether ketone (PEEK)). The printed flexible circuit fingers 1480 can be formed of any of various different materials that are typically used for forming such strips.

Outer electrodes 1446 including concentric conductive members 1450, 1452 of the type described above with respect to the distal tip 122 are attached to the outer surfaces of the flexible printed circuit material. Inner electrodes in the form of metal pads are attached to the inner surfaces of the flexible printed circuits fingers 1480 and are exposed to the interior of the distal tip 1422. Thermistors are attached to the inner surfaces of the flexible printed circuit fingers 1480, opposite the outer electrodes, and can be used to detect the temperature of their associated outer electrodes.

Figure 28:
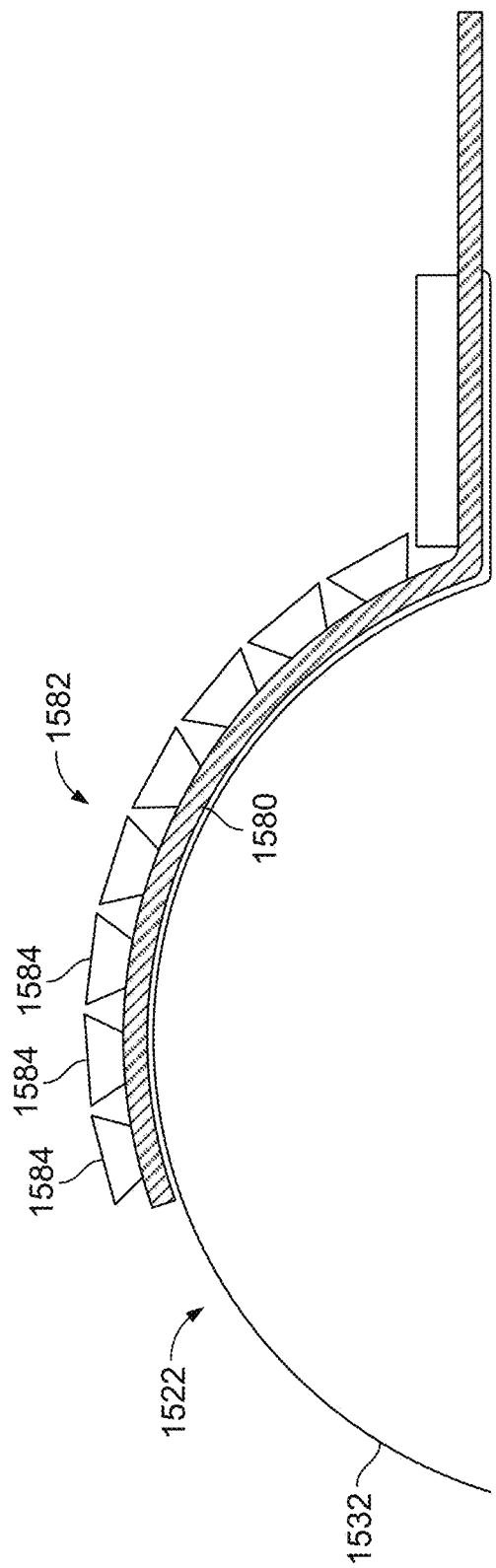
FIG. 28 is a schematic illustration of support members that can be positioned along a proximal end region of conformable tip.

Referring to FIG. 28, a distal tip 1522 includes a flexible printed circuit finger 1580 that extends along the proximal end region of a spherical body 1532 of the distal tip 1522. A patterned layer 1582 of stiffening material is applied to the finger 1580. Specifically, the material is applied to the flexible printed circuit material in multiple discrete segments 1584 that increase in width as they extend away from the flexible printed circuit material to provide asymmetrical bending behaviors. In the illustrated implementation, the segments 1584 are in the shape of trapezoids, but any of various other shapes that are wider along a top edge than along a bottom edge can be used. This arrangement allows for a radial inward force (i.e., a downward force in the illustrated view) that is applied to the proximal end region of the distal tip 1522 (i.e., the region of the distal tip 1522 along which the flexible printed circuit fingers 1580 and stiffening segments 1584 extend) to inwardly deflect the proximal end region of the distal tip 1522. As a result of this inward force, the discrete segments 1584 of stiffening material will be spaced apart. In contrast, the discrete segments 1584 of stiffening material will limit (e.g., prevent) the proximal end region of the distal tip 1522 from deflecting outward (e.g., in response to a proximal force applied to the distal end region of the distal tip 1522). Such a force would compress the discrete segments 1584 of stiffening material together. Due to the close proximity of the neighboring discrete segments 1584 and the stiffness of those segments, very little movement in the radial outward direction (i.e., in the upward direction in the illustrated view) will be allowed. In some cases, as few as one trapezoid (or other functionally equivalent shape) and one rigid element near the neck provides asymmetric bending behavior.

While the stiffening strips or segments 1482, 1582 of the distal tips 1422, 1522 illustrated in FIGS. 27 and 28 have been described as being attached to flexible printed circuit fingers 1480, 1580, the stiffening strips or segments 1482, 1582 can alternatively be integrally formed with the flexible printed circuit fingers 1480, 1580. In other implementations, no stiffening strips are added to the flexible printed circuit fingers. In such implementations, for example, portions of the flexible printed fingers extending along the proximal end region of the distal tip are simply increased in thickness to provide added support to the proximal region of the distal tip.

The various distal tips described herein can also include stiffening strips that are independent of any flexible printed circuit fingers that those tips might have. The distal tip can, for example, include separate stiffening strips that extend along the outer surface of the proximal end region in much the same way that the flexible printed circuit fingers 1480 extend along the outer surface of the distal tip 1422 illustrated in FIG. 27. The stiffening strips can be attached (e.g., thermally or adhesively bonded) to the outer surface of the distal tip or can simply rest along the outer surface of the distal tip in an unattached configuration. The stiffening strips could alternatively extend along and attach to the inner surface of the distal tip or could be embedded or encapsulated within the wall of the distal tip. Any of the various materials discussed above with respect to the stiffening strips 1482 illustrated in FIG. 27 can be used to form these stiffening strips.

Figure 30:
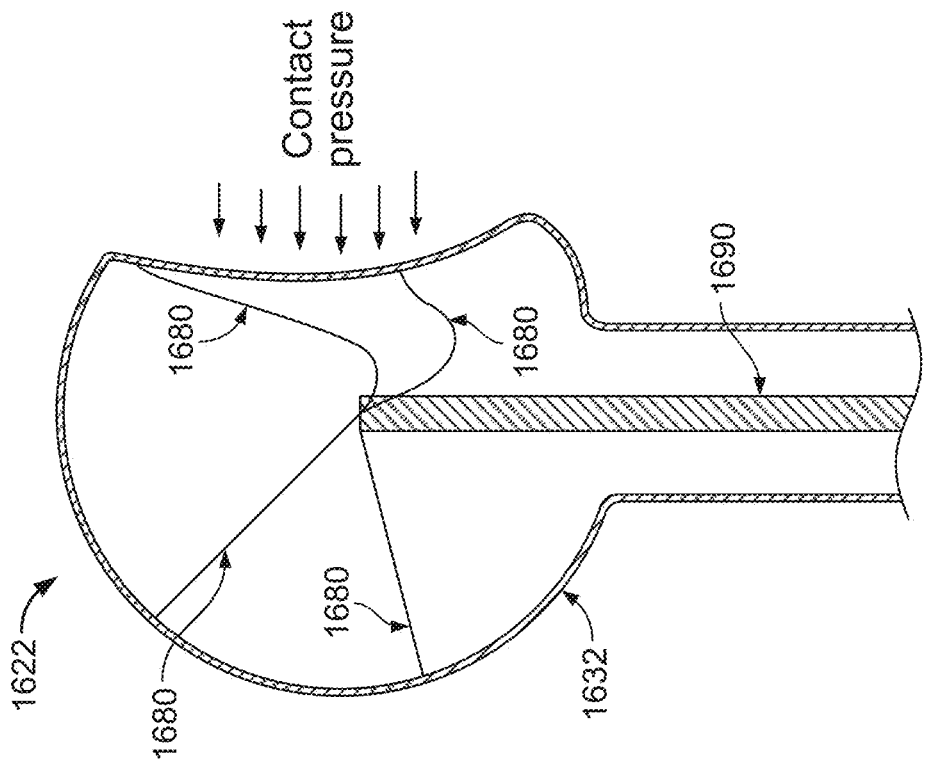
FIGS. 29 and 30 schematically illustrate a conformable tip, which includes support tethers, in an undeformed configuration and in a deformed configuration, respectively.
Figure 29:
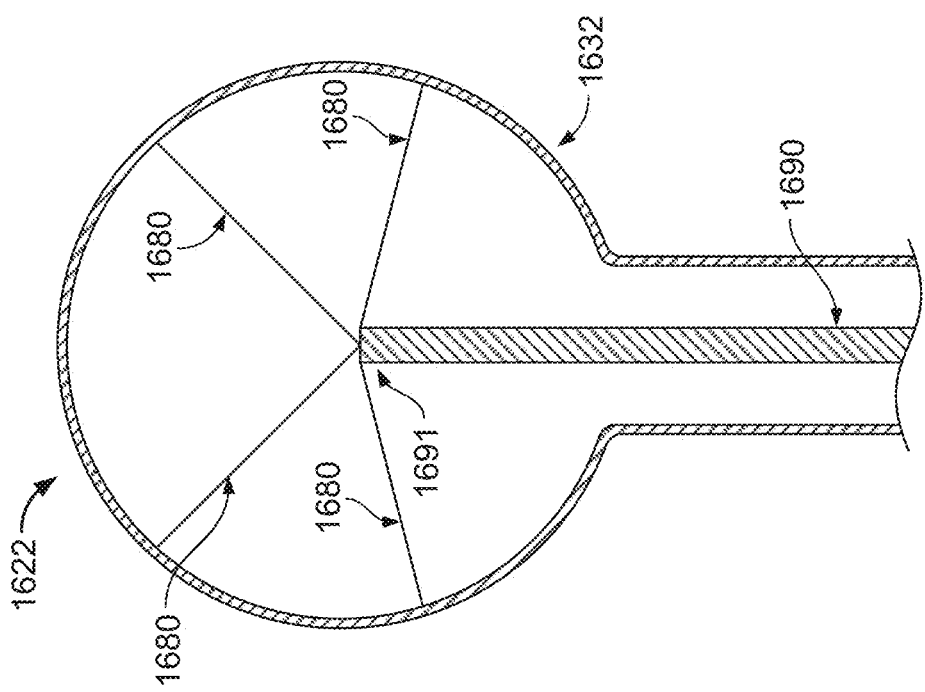

As an alternative to or in addition to stiffening members extending along the surface of the distal tip, tensioning tethers can be used limit the amount of radial outward deflection or deformation that the distal tip can experience. As shown in FIGS. 29 and 30, for example, a stiff member 1690, which is attached at its proximal end region to a catheter shaft, extends into the interior of a spherical body 1632 of a distal tip 1622, which is also attached at its proximal end region to the catheter shaft. Each of multiple tethers 1680 is anchored at one end to a distal end region 1691 of the stiff member 1690 and at its other end to the distal tip 1622 (e.g., the inner surface of the distal tip 1622). The tethers 1680 are in light tension when the distal tip 1622 is in its normal, undeformed configuration. The tethers 1680 can withstand higher tensile forces, however, in the event that a radially outward force is applied to a portion of the distal tip 1622 to which the tether 1680 is attached. The tethers 1680 are typically in the form of a wire or string and can be formed of any of various different materials, including metals (e.g., stainless steel) and polymers (e.g., Kevlar). Braided or solid core wires can be used.

FIG. 30 illustrates one side of the distal tip 1622 being inwardly deformed by a radially inwardly directed contact pressure. Because the tethers 1680 have a low buckling stiffness and are thus very complaint in compression, the tethers 1680 in the right hemisphere of the distal tip 1622 (i.e., the hemisphere to which the contact force is being applied) have buckled, allowing the inward deformation of the distal tip 1622. The resulting outward forces applied to the opposite side of the distal tip 1622 have placed the tethers 1680 in the left hemisphere in tension. These tethers 1680 limit (e.g., prevent) radial outward movement of the distal tip 1622 and thus helps to ensure that deformation of the distal tip 1622 occurs in those regions of the distal tip 1622 that are in contact with tissue.

While only four tethers are illustrated in FIGS. 29 and 30, it should be understood that more tethers can be used. Further, the tethers can be attached to any regions of the balloon for which outward deformation is undesired. In some examples, the tethers are formed from electrical wires extending to various electrodes and/or sensors of the ablation catheter.

While certain distal tips have been described as including conductive ink in some implementations other types of conductive layers can be used.

While the ablation electrode has been described in the form of a continuous conductive layer applied to the inner surface of the distal tip any of various other patterns can alternatively be used. In some implementations, the ablation electrode occupies a smaller area of the distal tip to provide increased resistive heating of the saline within the distal tip. As shown in FIG. 31, for example, the inner surfaces of proximal and distal end regions of a distal tip 1722 each include an ablation electrode in the form of a conductive layer 1720, but a central region 1721 of the distal tip 1722 is free of conductive material forming two discrete electrodes. Each of the two discrete regions having the conductive layer 1720 is connected to its own dedicated wire for receiving electrical energy from the ablation generator 116. This arrangement can be used to heat the saline to a desired temperature with one of the electrodes (e.g. the proximal one) before the saline exits the distal tip 1722.

During use, saline is delivered via an irrigation lumen 1794 of the catheter shaft to the interior of the distal tip 1722. When it is desired to heat the saline, the energy can be applied to a proximal region of the conductive layer 1720 only. As the current passes through the saline from a proximal end region of the distal tip 1722 toward a distal end region of the distal tip 1722 (e.g., when valves at the distal end region of the distal tip 1722 are opened due to contact with tissue), the impedance caused by the saline results in resistive heating that raises the temperature of the saline. When it is desired to ablate tissue with less heating of the saline in the distal tip 1722, electrical energy can be applied to both a proximal and a distal regions of the conductive layer 1720. These schemes can be used, for example, to avoid endocardial sparing as previously described.

As shown in FIG. 31, the ablation catheter is equipped with a temperature sensor 1790 (e.g., thermistor) that can be used to monitor the temperature of the saline within the distal tip 1722. Temperature data can be received by the control unit in the catheter interface unit 108 from the catheter via wires extending through the catheter shaft, and the control unit can cause the ablation generator 116 to deliver electrical energy in a manner to achieve the desired saline temperature.

As an alternative to or in addition to using two discrete regions each having an ablation electrode to heat the saline within the distal tip, other heating techniques can be used. As shown in FIG. 32, for example, an ablation catheter includes a distal tip 1822 having an ablation electrode 1820 on its inner surface in the form of conductive coating. A heating element 1892 is positioned within the catheter shaft along an irrigation lumen 1894 leading to the distal tip 1822 and can be used to heat the saline flowing into the distal tip. The control unit of the catheter interface unit 108 can control the heating element 1892 (i.e., can control the amount of electrical energy applied to the heating element 1892) based on temperature data received from the temperature sensor 1890. The heating element 1892 can, for example, be activated only when it is desired to heat the saline.

While the above-described distal tips include ablation electrodes in the form of conductive layers, other types of ablation electrodes can alternatively or additionally be used with any of those distal tips. In certain implementations, for example, the material of the spherical body and the neck of the distal tip is loaded with an electrically conductive material such that material of the spherical body and the neck can transmit energy to saline within the distal tip. In certain implementations, for example, the distal tip is formed of a polymer that is loaded with electrically conductive particles. Examples of suitable polymers include silicone, SEBS, polyurethane, Nylon, and PEBAX. Examples of suitable electrically conductive particles include silver particles, glass coated silver particles, carbon particles, and gold particles. To prevent the energy from being transmitted directly to the blood or tissue of the patient outside the distal tip by the electrically conductive material of the spherical body and the neck, the outer surface of the distal tip can be coated with an electrically insulating material, such as silicone, parylene, or polyurethane.

Figure 33:
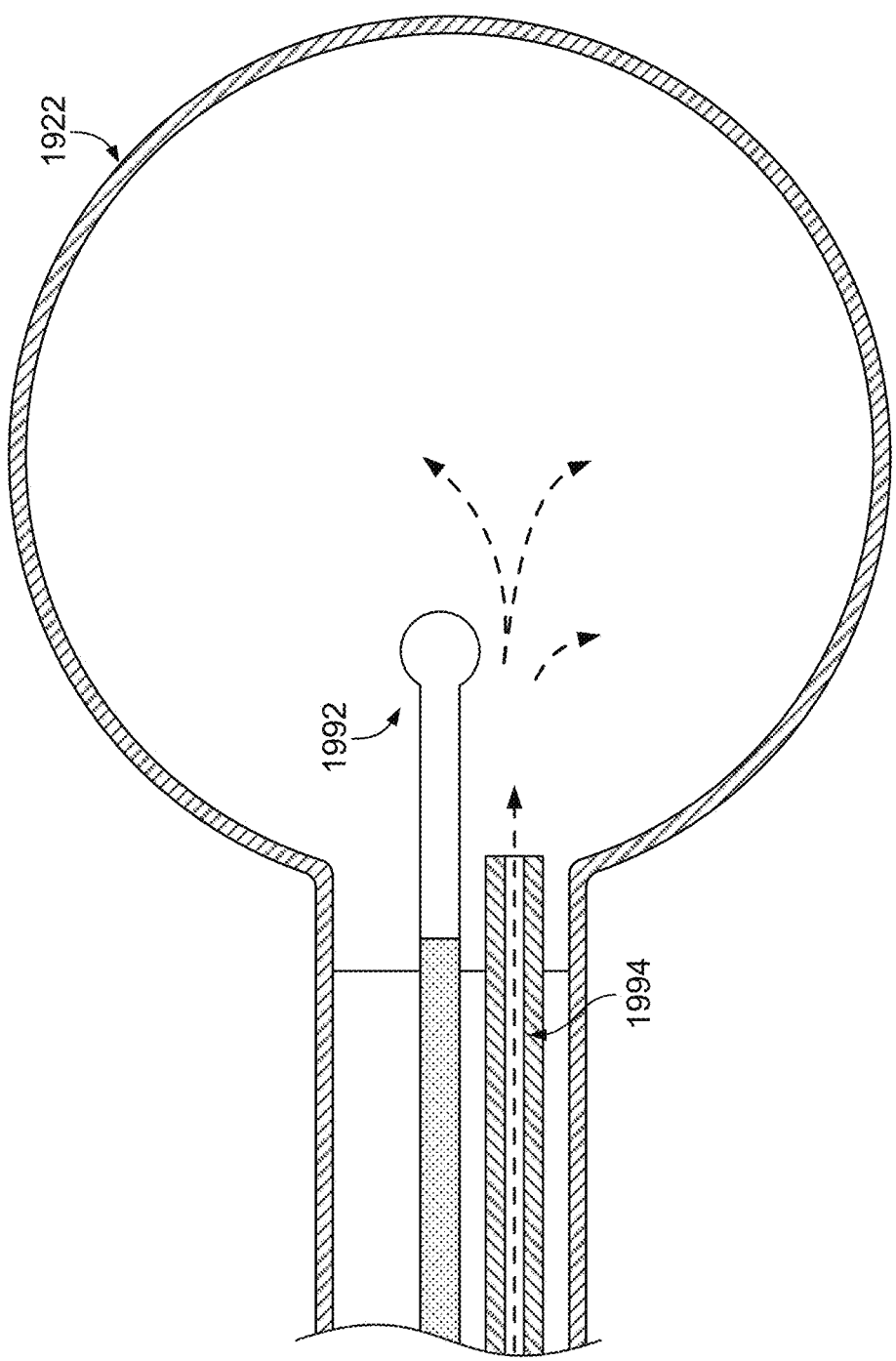
FIG. 33 is a cross-sectional view of the distal end region of an ablation catheter that includes an ablation electrode disposed in the interior region of a conformable tip.

In some implementations, as shown in FIG. 33, a rod-shaped ablation electrode 1992 extends distally from the distal end of the catheter shaft and into the interior of the distal tip 1922. The saline (indicated by dashed arrows in FIG. 33) exits the irrigation lumen 1994 of the catheter shaft and fills the interior of the distal tip 1922. As the distal tip fills with saline, the saline will contact the ablation electrode 1992, allowing energy to be transmitted from the ablation electrode 1992 to or through the saline. This arrangement typically results in the ablation electrode 1992 being positioned close to the tissue being ablated, which can reduce the impedance to tissue and allow more power to be delivered. Various schemes can be employed to increase the surface area of the ablation electrode 1992 and therefore reduce its impedance while keeping its volume low. For example, the surface area of the rod or wire can be increased by adding exposed branches or strands of wire or coiling an exposed length of it within the tip. Alternatively, the electrode could be comprised of a convoluted strip or surface of conductive material.

While the ablation electrode 1992 has been described as being fixedly attached to the distal end of the catheter shaft, the ablation electrode can alternatively be axially displaceable within the catheter shaft and the distal tip. In some implementations, for example, the ablation electrode can be integrated with a push rod that is used to collapse the distal tip prior to insertion of the distal tip into the patient. The ablation electrode can, for example, be in the form of a bulbous element attached to the distal end of the push rod. This configuration can provide the ablation electrode with an increased surface area, while using the relatively thin rod to deliver the energy to the ablation electrode. This can help to limit the total volume of space within the distal tip occupied by the push rod and the ablation electrode.

While various types of ablation electrodes have been described, other types of ablation electrodes can be used. In certain implementations, for example, the ablation electrode can be implemented as a collection of thin conducting threads that either extend along the irrigation lumen and/or extend into the interior region of the distal tip.

Figure 34:
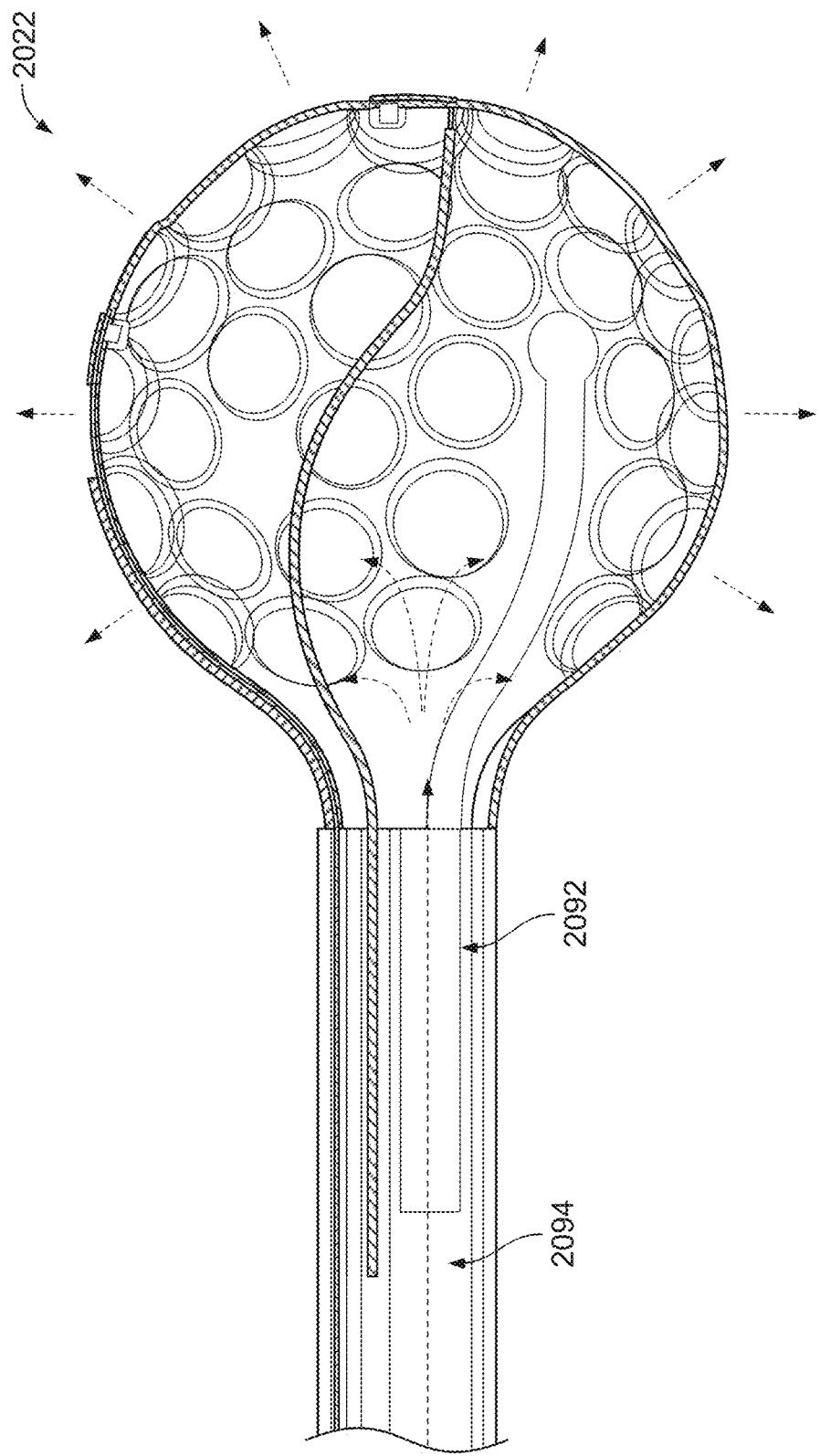
FIG. 34 is a schematic illustration of the distal end region of an ablation catheter that includes an ablation electrode positioned along an irrigation lumen extending through a shaft of the catheter.

While the ablation electrodes of many of the distal tips above have been described as being positioned within the distal tip, the ablation electrode can alternatively or additionally be located in other regions of the ablation catheter. FIG. 34, for example, illustrates an ablation electrode 2092 positioned along an irrigation lumen 2094 of the catheter shaft. The ablation electrode 2092 is in the form of a tube that forms a portion of the irrigation lumen 2094. The ablation electrode 2092 can be formed of one or more electrically conductive materials, such as platinum, platinum-iridium alloy, gold, or stainless steel. The saline flowing through the lumen 2094 acts as a conducting medium that carries energy from the ablation electrode 2092 to tissue of the patient as the saline exits the distal tip 2022. In addition, the continuous flow of the saline acts to cool the ablation electrode 2092 in order to avoid steaming at the ablation electrode/saline interface.

In some implementations, to further cool the ablation electrode 2092, the ablation electrode 2092 can be configured such that its outer surface is flush with the outer surface of the catheter shaft. The outer surface can also be coated with a thin insulator, such as parylene. This allows additional cooling of the metal though the blood. In certain implementations, the electrode is made from one or more materials, such as platinum iridium or gold, that provide additional cooling benefits to the ablation electrode.

In some implementations, the ablation electrode can be situated on the outer rather than the inner surface of the conformable distal tip which includes shape activated valves. With this implementation, energy will not be selectively applied using saline, however, selective cooling using the shape activated valves can still be accomplished. Many of the other benefits, as described elsewhere, including the conforming of the tip to tissue and of the sensing components can still be accomplished.

In some implementations holes or slits not having valve action can be implemented. With this implementation energy and saline will not be selectively applied. Many of the other benefits, as described elsewhere, including the conforming of the tip to tissue with its beneficial impact on lesion characteristics and of the sensing components can still be accomplished.

While the neck 130 of the distal tip 122 has been described as being attached to the catheter shaft 128 using a compression fit and/or a mechanical connection, any of various other attachment techniques can alternatively or additionally be used to attach the distal tip 122 and the various other distal tips described herein to the catheter shaft. In certain implementations, for example, an electrically conductive adhesive is disposed between the outer surface of the catheter shaft and the inner surface of the neck to secure those components together. The electrically conductive adhesive, in addition to providing a securing function, can facilitate transmission of electrical energy from the conductive ring at the distal end of the catheter shaft to the ablation electrode applied to the inner surface of the neck. Examples of electrically conductive adhesives that can be used include silver-filled silicone RTV adhesive, Loctite 3888, for example.

While many of the distal tips discussed above have been described as including thermistors, other types of temperature sensors, such as thermocouples, can alternatively or additionally be used. For example, ink-based thermocouples can be applied directly to the outer surface of the tip. Alternatively, or additionally, ink based thermistors, thin-film elements (e.g., ink-on-flex circuits assembled on the tip), and other temperature sensors can be used.

Figure 35:
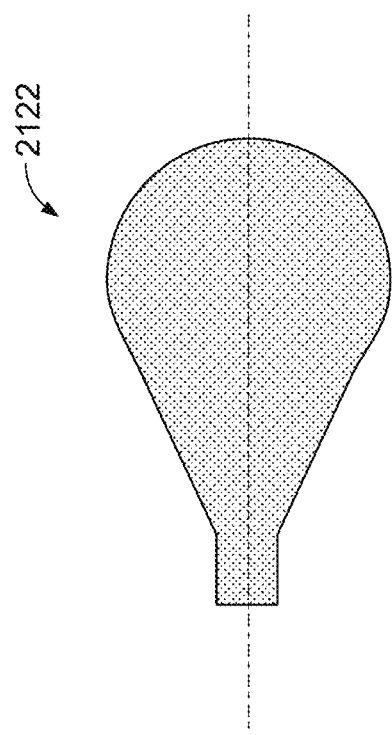
FIGS. 35-38 illustrate various shapes of conformable tips for ablation catheters.
Figure 36:
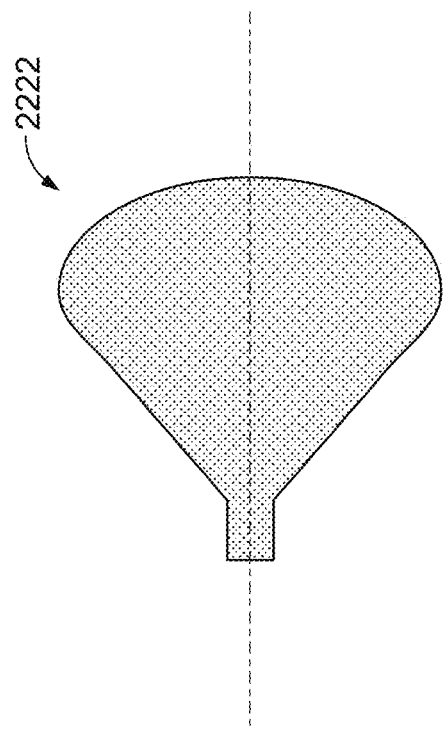
Figure 37:
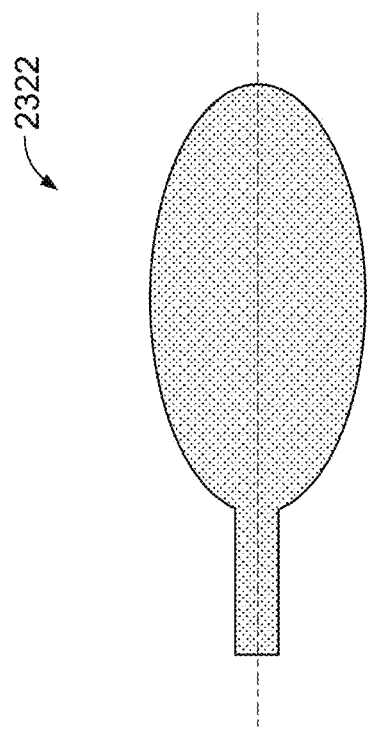
Figure 38:
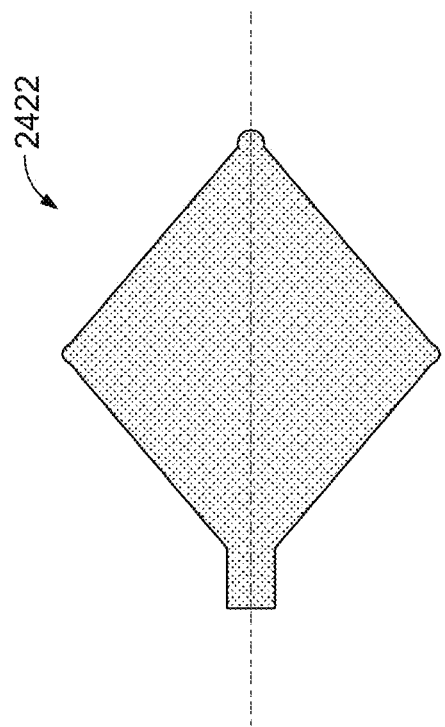

While the distal tips discussed above have been described as having a spherical shape, distal tips of other shapes can be used. The shape of the distal tip can, for example, be selected to correspond to the shape of an anatomical feature to be treated or to perform a particular type of procedure desired. FIGS. 35 and 36 illustrate distal tips 2122, 2222 that have tear drop and garlic clove shapes, respectively. The distal section of the body of each of these tips is generally rounded or hemispherical and the proximal section tapers to a smaller diameter toward the proximal end. Such a distal tip shape can provide more structural support in the proximal section while maintaining a large surface area in the distal section, which allows for the formation of large lesions. In certain implementations, as shown in FIG. 37, a distal tip 2322 having a football shape or hammerhead shark shape can be used. This type of tip can be particularly beneficial when ablation along a line of contact with tissue is desired. FIG. 38 illustrates an opposed-cones shaped distal tip 2422, which can be used to make a lesion in the form of a circle when the conformable tip is pressed into an opening (e.g. of a vein) of arbitrary diameter. Any of various other asymmetric shapes can alternatively be implemented in order to selectively ablate in one area, or to fit the distal tip into a particularly shaped anatomical structure.

While the distal tip has generally been described as being loaded with a radiopaque additive such as a barium sulfate or bismuth additive, other materials and/or inks could be used to permit the distal tip to be visualized using fluoroscopy, during an ablation treatment. In some implementations, a stiffening material, e.g., Nitinol, can be added to the distal tip to facilitate visualization during an ablation treatment.

The distal section of the catheter shaft 128 can be implemented as single lumen. In other implementations, the catheter shaft includes two or more lumens. In certain implementations, for example, the catheter shaft includes multiple lumens for separately housing the various wires and cables and tube transporting the fluid.

While the ablation catheter 104 has been described as a bi-directional, steerable catheter, the catheter can alternatively be a unidirectional, steerable catheter. For example, rather than having two wires that are circumferentially spaced by about 180 degrees and are attached to the ring positioned at the distal end of the catheter shaft, a single wire can extend along the catheter shaft and be attached to the ring. In addition, while the catheter has been described as including a deflectable or steerable catheter shaft, non-steerable catheter shafts can alternatively be used in combination with or independently from a fixed-curve or articulating sheath, or robotic navigation systems While the ablation catheter 104 has been described as including an insertion sheath that is retractable for constraining the distal tip 122 in a collapsed configuration, other types of sheaths can be used. In some implementations, for example, the sheath designed to be torn away from the catheter shaft 128 after insertion of the distal tip 122 into the patient. In this example, the torn sheath can be removed from the catheter shaft 128.

While the tips of many ablation catheters described herein have been described as expanding to a larger size after delivery into the patient, in some implementations a tip of an ablation catheter can expand to a larger size after being delivered to the treatment site.

While the ablation catheters above have been described as including a sheath to constrain the distal tip in a collapsed configuration while the ablation catheter is being inserted through an introducer sheath into the patient, other types of devices can alternatively or additionally be used to constrain the distal tip 122 in its collapsed configuration. In some implementations, for example, the ablation catheter includes an axially displaceable rod positioned within a lumen of the catheter shaft. The distal end of the rod typically terminates in or near the distal tip 122. In certain implementations, the distal end of the rod is attached to (e.g., mechanically attached to or adhesively bonded to) the inner surface of the distal end of the distal tip. The distal end of the rod can include a bulbous head or some other type of blunt feature to help prevent damage to the distal tip due to contact between the distal end of the rod and the inner surface of the distal tip. The proximal end of the rod extends proximally from the proximal end of the handle such that the user is able to grasp and manipulate the portion of the rod proximal to the handle. Prior to insertion of the ablation catheter into the patient, the user can push the rod in the distal direction. When doing so, the distal end of the rod contacts the inner surface of the distal end of the distal tip, causing the distal tip to lengthen and partially collapse. This technique reduces the overall diameter of the distal tip, allowing it to be more easily inserted into the patient. The rod can also incorporate the ablation electrode in certain implementations.

While measured or monitored values have generally been described as impedance values, other values, or parameters can be used. For example, voltage values and current values, and so forth can be additionally or alternatively be measured or monitored.

While data collected form the various sensors (e.g., electrodes, thermistors, etc.) has been described as being sent to the catheter interface unit 108 for processing, the data can alternatively be sent to other devices for processing. In certain implementations, for example, data is sent from sensors of the ablation catheter to the mapping system 112 and/or recording system 111.

While the catheter interface unit 108, the recording system 111, the mapping system 112, the irrigation pump 114, and the ablation generator 116 have been described as separate components, in certain implementations, two or more of those components are integrated into a single machine. In some implementations, for example, the catheter interface unit is integrated with the ablation generator and the irrigation pump. In certain implementations, all of these components are integrated into a single machine.

While the catheter interface unit 108 has been largely described as including a current source for generating a current signal (e.g., a sinusoidal current signal at a particular frequency), the catheter interface unit 108 can alternatively or additionally include a voltage source for generating voltage waveforms. In some implementations, the catheter interface unit 108 is configured to generate a sinusoidal or square wave voltage that is applied across the various electrodes, and the resultant current running through the electrodes can be measured. In some implementations, a combination of voltage and current measurements can be used to determine impedances between electrodes.

While the systems above have been described as comparing impedance values (e.g., impedance between any combination of electrodes or electrode components, including the external electrodes 146, the internal electrodes 148, the ablation electrode 120, the return electrode 118, the central conductive component 150 of the external electrodes 146, the annular conductive component 152 of the external electrodes 146, etc.) to threshold values in order to make determinations (e.g., determinations related to contact between tissue and electrode(s), determinations related to valve state(s), etc.), other implementations are possible. For example, in some implementations, impedance values (or, e.g., combinations of impedance values) between the central conductive component 150 of external electrodes 146 and the annular conductive component 152 of external electrodes 146 can be used to determine a degree of contact between the tissue and the external electrodes 146 (e.g., rather than or in addition to simply making a binary determination of whether external electrodes 146 are in contact with the tissue).

In some implementations, particular impedance values (or, e.g., combinations of particular impedance values between various electrodes) can correspond to open/closed states of various values. The open/closed states of various values can be mapped to an impedance profile of the electrodes. In some implementations, impedance values between various electrodes can be measured, and the open/closed states of various valves can be determined based on this cumulative impedance information (e.g., rather than based on comparisons between the impedance values and corresponding thresholds). In some implementations, impedance values can be used to determine a degree of closure of various valves (e.g., rather than or in addition to simply making a binary determination of whether values are open or closed).

While the systems above have been described as using saline to carry the energy from the ablation electrode to the patient's tissue, any of various other biocompatible electrically conductive fluids can alternatively or additionally be used. In some examples, the saline is a hypertonic saline allowing improved energy delivery, e.g., through lower impedance.

In addition, while many of the ablation catheters described above rely on electrically conductive fluids to carry the RF energy from the ablation electrode to the tissue, in some implementations, the ablation catheter is configured to transmit RF energy directly from the ablation catheter to the tissue of the patient. In some such implementations, for example, the ablation electrode extends along the distal tip of the ablation catheter and directly contacts the tissue to be ablated. Alternatively, or additionally, the energy can be conducted from the ablation electrode to the tissue of the patient via electrically conductive bodily fluids of the patient.

While the systems and methods described above relate to RF ablation, in certain implementations, other types of energy can be used with these systems and methods. For example, irreversible electroporation includes a sequence of brief but high voltage energy application to induce tissue apoptosis and form a lesion. One of the challenges associated with irreversible electroporation includes energy loss during energy delivery to a target tissue. Energy loss is particularly problematic in endocardial applications where most of the energy is shunted away from tissue towards blood due to blood's higher conductivity. Just as with RF ablation, the systems and methods described herein are also particularly well suited for irreversible electroporation because, for example, the conformal tip, shape activated valves, relatively large catheter tip-tissue contact area, and ability to know catheter state prior to energy application allow selective application of the electroporation energy to target tissue.

While the ablation catheter 104 has been described as being used to perform a cardiac ablation treatment, the ablation catheter 104 can alternatively or additionally be used to carry out various other types of treatments. These other treatments include, but are not limited to: the ablation of tumors, the ablation of uterine tissue to control excessive uterine bleeding, renal and carotid denervation, and selective drug and biological agent delivery.

The systems, methods, and techniques described herein can be implemented, at least in part, on a computing device and/or a mobile computing device. For example, the catheter interface unit 108 (FIG. 1) can be implemented as a computing device and/or a mobile computing device. In some implementations, the mobile computing device can be configured to display information related to the ablation procedure.

The computing device can represent various forms of digital computers, such as laptops, desktops, workstations, personal digital assistants, servers, blade servers, mainframes, and other appropriate computers. The mobile computing device can represent various forms of mobile devices, such as personal digital assistants, cellular telephones, smartphones, and other similar computing devices. The components described herein, their connections and relationships, and their functions, are meant to be examples only, and are not meant to be limiting.

The computing device can include a processor, a memory, and a storage device. The processor can process instructions for execution within the computing device, including instructions stored in the memory or on the storage device to display graphical information for a GUI on an external input/output device, such as a display. In some implementations, multiple processors can be used, as appropriate, along with multiple memories and types of memory. Also, multiple computing devices can be connected, with each device providing portions of the necessary operations (e.g., as a server bank, a group of blade servers, or a multi-processor system).

The memory can store information within the computing device. In some implementations, the memory is a volatile memory unit or units. In some implementations, the memory is a non-volatile memory unit or units. The memory can also be another form of computer-readable medium, such as a magnetic or optical disk.

The storage device is capable of providing mass storage for the computing device. In some implementations, the storage device can be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, the processor), can perform one or more methods, such as those described above. The instructions can also be stored by one or more storage devices such as computer- or machine-readable mediums (for example, the memory, the storage device, or memory on the processor). In some implementations, the memory can store information received by the mapping system 112, the recording system 111, the irrigation pump 114, and/or the ablation generator 116 described above with reference to FIG. 1.

In some implementations, the computing device can include expansion ports, which can include various communication ports (e.g., USB, Bluetooth, Ethernet, wireless Ethernet) that can be coupled to one or more input/output devices, such as a keyboard, a pointing device, a scanner, or a networking device such as a switch or router, e.g., through a network adapter.

The computing device can be implemented in a number of different forms. For example, the computing device can be implemented as a standard server, or multiple times in a group of such servers. In addition, the computing device can be implemented in a personal computer such as a laptop computer. The computing device can also be implemented as part of a rack server system. Alternatively, components from the computing device can be combined with other components in a mobile device, such as a mobile computing device. Each of such devices can contain one or more of the computing device and the mobile computing device, and an entire system can be made up of multiple computing devices communicating with each other.

The mobile computing device can include a processor, a memory, an input/output device such as a display, a communication interface, and a transceiver, among other components. The mobile computing device can also be provided with a storage device, such as a micro-drive or other device, to provide additional storage.

The processor can execute instructions within the mobile computing device, including instructions stored in the memory. The processor can be implemented as a chipset of chips that include separate and multiple analog and digital processors. The processor can provide, for example, for coordination of the other components of the mobile computing device, such as control of user interfaces, applications run by the mobile computing device, and wireless communication by the mobile computing device.

The processor can communicate with a user through a control interface and a display interface coupled to the display. The control interface can receive commands from a user and convert them for submission to the processor. In addition, an external interface can provide communication with the processor, so as to enable near area communication of the mobile computing device with other devices. The external interface can provide, for example, for wired communication in some implementations, or for wireless communication in other implementations, and multiple interfaces can also be used.

The mobile computing device can be configured to display information related to the ablation procedure. For example, the mobile computing device can be configured to present a digital readout of the actual power, voltage and current being delivered, the calculated impedance (e.g., based on measured current and voltage) between electrodes (e.g., between the ablation electrode 120 and the return electrode 118) during the delivery of energy, the measured temperature detected by the various sensors, the number of times the ablation generator 116 has been activated, and/or the total elapsed time during which energy has been delivered to the patient. In some implementations, the mobile computing device can display data that represents the shape of the distal tip 122 or the shape and/or progress of the lesion being generated by the ablation catheter 104. In some implementations, the mobile computing device can display the screenshots described above with reference to FIGS. 9 and 10 or similar screen shots.

The memory can store information within the mobile computing device. The memory can be implemented as one or more of a computer-readable medium or media, a volatile memory unit or units, or a non-volatile memory unit or units. An expansion memory can also be provided and connected to the mobile computing device through an expansion interface, which can include, for example, a SIMM (Single In Line Memory Module) card interface. The expansion memory can provide extra storage space for the mobile computing device, or can also store applications or other information for the mobile computing device. Specifically, the expansion memory can include instructions to carry out or supplement the processes described above.

In some implementations, instructions are stored in an information carrier. The instructions, when executed by one or more processing devices (for example, the processor), can perform one or more methods, such as those described above. The instructions can also be stored by one or more storage devices, such as one or more computer or machine-readable mediums (for example, the memory, the expansion memory, or memory on the processor). In some implementations, the instructions can be received in a propagated signal, for example, over the transceiver or the external interface.

The mobile computing device can communicate wirelessly through the communication interface, which can include digital signal processing circuitry where necessary. The communication interface can provide for communications under various modes or protocols understood to those skilled in the art. Such communication can occur, for example, through the transceiver using a radio-frequency. In addition, short-range communication can occur, such as using a Bluetooth, WiFi, or other such transceiver. In addition, a GPS (Global Positioning System) receiver module can provide additional navigation- and location-related wireless data to the mobile computing device, which can be used as appropriate by applications running on the mobile computing device.

The mobile computing device can also communicate audibly using an audio codec, which can receive spoken information from a user and convert it to usable digital information. The audio codec can likewise generate audible sound for a user, such as through a speaker, e.g., in a handset of the mobile computing device.

The mobile computing device can be implemented in a number of different forms. For example, the mobile computing device can be implemented as a cellular telephone. The mobile computing device can also be implemented as part of a smart-phone, a tablet, a personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementations in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) can include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device for displaying information to the user and a keyboard and a pointing device by which the user can provide input to the computer. Other kinds of devices can be used to provide for interaction with a user as well.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

C. Additional Examples

Several aspects of the present technology are set forth in the following examples.

1. An ablation catheter comprising:
a catheter body defining a fluid delivery lumen, and
a deformable tip secured to the catheter body,
wherein the ablation catheter is configured to permit liquid communication between an interior of the deformable tip and an exterior of the deformable tip in response to a deformation of the tip.

2. The catheter of example 1 wherein the deformable tip is formed of an elastomeric material.

3. The catheter of example 1 or example 2 further comprising a conductive member configured to deliver current to liquid within the deformable tip such that liquid passing from the interior of the deformable tip to the exterior of the deformable tip can convey RF energy away from the deformable tip.

4. The catheter of example 1, 2, or 3 wherein the ablation catheter is configured to emit RF energy away from the deformable tip in response to the deformation of the deformable tip.

5. The catheter of example 4 wherein the RF energy is transmitted from the interior of the deformable tip to the exterior of the deformable tip via liquid exiting the deformable tip.

6. The catheter of example 1, 2, 3, 4, or 5 wherein the deformable tip comprises one or more valves, and wherein the one or more valves are configured to open in response to the deformation of the deformable tip.

7. The catheter of example 6 wherein the one or more valves comprise one or more slits extending through a wall of the deformable tip.

8. The catheter of example 6 or example 7 wherein the one or more valves comprise 3-legged slits extending through the wall of the deformable tip.

9. The catheter of example 7 or example 8 wherein the one or more slits extend through a recessed region of the wall of the deformable tip.

10. The catheter of example 9 wherein the recessed region of the wall of the deformable tip is tetrahedral-shaped.

11. The catheter of example 9 wherein the recessed region of the wall of the deformable tip is hemispherical.

12. The catheter of example 6, 7, 8, 9, or 10 wherein the deformable tip comprises support regions between adjacent valves.

13. The catheter of example 12 wherein the support regions comprise ribs.

14. The catheter of example 13 wherein the ribs are attached at opposite ends to walls of adjacent valves.

15. The catheter of example 1, 2, 3, 4, 5, 6, 7, 8, 9, 10, 11, 12, 13, or 14 wherein a support structure is configured to support a proximal end region of the deformable tip.

16. The catheter of example 15 wherein the support structure includes one or more ribs that extend along the proximal end region of the deformable tip.

17. The catheter of example 15 or example 16 wherein the support structure is integral with a wall of the deformable tip.

18. The catheter of example 15 or example 16 wherein the support structure is a component that is attached to the deformable tip.

19. The catheter of example 15, 16, 17, or 18 wherein the support structure comprises a plurality of fingers that extend along the proximal end region of the deformable tip.

20. The catheter of example 19 further comprising one or more electrodes attached to one or more of the fingers.

21. The catheter of example 20 wherein the fingers are flexible printed circuits arranged to transmit signals to and from the one or more electrodes.

22. The catheter of example 1, 2, 3, 4, 5, 6, 7, 8, 9, 10, 11, 12, 13, 14, 15, 16, 17, 18, 19, 20, or 21 wherein the deformable tip has a thickness of 0.20 mm or less.

23. The catheter of example 1, 2, 3, 4, 5, 6, 7, 8, 9, 10, 11, 12, 13, 14, 15, 16, 17, 18, 19, 20, 21, or 22 further comprising a conductive material along an inner surface of the deformable tip.

24. The catheter of example 23 wherein the conductive material is conductive to RF energy.

25. The catheter of example 23 or example 24 wherein the conductive material is a conductive layer.

26. The catheter of example 23, 24, or 25 wherein the conductive layer comprises conductive ink.

27. The catheter of example 23, 24, 25, or 26 wherein the conductive material extends along at least a portion of a neck of the deformable tip, and wherein the neck is secured to the catheter body such that the conductive material contacts a conductive element exposed along an outer surface of the catheter body.

28. The catheter of example 25, 26, or 27 wherein the conductive layer covers substantially an entire inner surface of the deformable tip.

29. The catheter of example 1, 2, 3, 4, 5, 6, 7, 8, 9, 10, 11, 12, 13, 14, 15, 16, 17, 18, 19, 20, 21, 22, 23, 24, 25, 26, 27, or 28 further comprising a conductive material along an inner surface of the deformable tip.

30. The catheter of example 1, 2, 3, 4, 5, 6, 7, 8, 9, 10, 11, 12, 13, 14, 15, 16, 17, 18, 19, 20, 21, 22, 23, 24, 25, 26, 27, 28, or 29 wherein a body of the deformable tip comprises a conductive material.

31. The catheter of example 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 further comprising an insulating layer along an outer surface of a/the body of the deformable tip.

32. The catheter of example 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 wherein a/the body of the deformable tip comprises a polymeric material containing conductive particles.

33. The catheter of example 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 wherein the ablation catheter is configured to cause liquid to flow from the interior of the deformable tip toward an object that is in contact with and deforming the deformable tip.

34. The catheter of example 33 wherein the object is tissue.

35. An ablation catheter comprising:
a catheter body;
a tip secured to the catheter body, wherein an inner surface of the tip includes a conductive layer, and wherein the tip comprises one or more valves configured to permit liquid communication from an interior of the tip to an exterior of the tip.

36. The ablation catheter of example 35 wherein the tip is deformable.

37. The catheter of example 36 wherein the deformable tip is formed of an elastomeric material.

38. The catheter of example 35, 36, or 37 wherein the conductive layer is configured to deliver current to liquid within the tip such that liquid passing from the interior of the tip to the exterior of the tip can convey RF energy away from the tip.

39. The catheter of example 35, 36, 37, or 38 wherein the ablation catheter is configured to emit RF energy away from the tip.

40. The catheter of example 39 wherein the RF energy is transmitted from the interior of the tip to the exterior of the tip via liquid exiting the tip.

41. The catheter of example 35, 36, 37, 38, 39, or 40 wherein the one or more valves are configured to open in response to deformation of the tip.

42. The catheter of example 35, 36, 378, 38, 39, 40, or 41 wherein the one or more valves comprise one or more slits extending through a wall of the tip.

43. The catheter of example 42 wherein the one or more slits extend through a recessed region of the wall of the tip.

44. The catheter of example 35, 36, 37, 38, 39, 40, 41, 42, or 43 wherein the tip comprises support regions between adjacent valves.

45. The catheter of example 44 wherein the support regions comprise ribs.

46. The catheter of example 45 wherein the ribs are attached at opposite ends to walls of adjacent valves.

47. The catheter of example 35, 36, 37, 38, 39, 40, 41, 42, 43, 44, 45, or 46 wherein a support structure is configured to support a proximal end region of the tip.

48. The catheter of example 35, 36, 37, 38, 39, 40, 41, 42, 43, 44, 45, 46, or 47 wherein the tip has a thickness of 0.20 mm or less.

49. The catheter of example 35, 36, 37, 38, 39, 40, 41, 42, 43, 44, 45, 46, 47, or 48 wherein the conductive layer is conductive to RF energy.

50. The catheter of example 35, 36, 37, 38, 39, 40, 41, 42, 43, 44, 45, 46, 47, 48, or 49 wherein the conductive layer comprises conductive ink.

51. The catheter of example 35, 36, 37, 38, 39, 40, 41, 42, 43, 44, 45, 46, 47, 48, 49, or 50 wherein the conductive layer extends along at least a portion of a neck of the tip, and wherein the neck is secured to the catheter body such that the conductive layer contacts a conductive element exposed along an outer surface of the catheter body.

52. The catheter of example 35, 36, 37, 38, 39, 40, 41, 42, 43, 44, 45, 46, 47, 48, 49, 50, or 51 wherein the conductive layer covers substantially an entire inner surface of the tip.

53. The catheter of example 35, 36, 37, 38, 39, 40, 41, 42, 43, 44, 45, 46, 47, 48, 49, 50, 51, or 52 wherein the ablation catheter is configured to cause liquid to flow from the interior of the tip toward an object that is in contact with and deforming the tip.

54. An ablation catheter comprising:
a catheter body defining a fluid delivery lumen;
a deformable tip secured to the catheter body, the deformable tip in fluid communication with the fluid delivery lumen; and
one or more deformable valves protruding from the deformable tip,
wherein the one or more deformable valves define respective one or more slits, and wherein each slit is openable in response to deformation of the deformable tip.

55. The ablation catheter of example 54 wherein the one or more deformable valves protrude radially outward from the deformable tip.

56. The ablation catheter of example 54 wherein the one or more deformable valves protrude radially inward from the deformable tip.

57. The ablation catheter of example 54, 55, or 56 wherein the one or more deformable valves are integral with the deformable tip.

58. The ablation catheter of example 54, 55, 56, or 57 wherein the deformable tip is configured such that a fluid from the fluid delivery lumen flows through a slit in response to a deformation of a respective deformable valve of the one or more deformable valves.

59. The ablation catheter of example 54, 55, 56, 57, or 58 wherein the deformable tip is configured such that fluid from the fluid delivery lumen exits the deformable tip through a slit in response to a deformation of a respective deformable valve of the one or more deformable valves.

60. The ablation catheter of example 58 or example 59 wherein a flow rate of liquid exiting the deformable tip increases as a degree of deformation of the deformable tip increases.

61. The ablation catheter of example 54, 55, 56, 57, 58, 59, or 60 wherein the deformable tip is formed of an elastomeric material.

62. The ablation catheter of example 54, 55, 56, 57, 58, 59, 60, or 61 further comprising a conductive member configured to deliver current to liquid within the deformable tip such that liquid passing from an interior of the deformable tip to an exterior of the deformable tip can convey RF energy away from the deformable tip.

63. The ablation catheter of example 54, 55, 56, 57, 58, 59, 60, 61, or 62 wherein the ablation catheter is configured to emit RF energy away from the deformable tip in response to the deformation of the deformable tip.

64. The ablation catheter of example 63 wherein the RF energy is transmitted from an interior of the deformable tip to an exterior of the deformable tip via liquid exiting the deformable tip.

65. The ablation catheter of example 54, 55, 56, 57, 58, 59, 60, 61, 62, 63, or 64 wherein the deformable tip comprises support regions between adjacent valves.

66. The ablation catheter of example 65 wherein the support regions comprise ribs.

67. The ablation catheter of example 66 wherein the ribs are attached at opposite ends to walls of adjacent valves.

68. The ablation catheter of example 54, 55, 56, 57, 58, 59, 60, 61, 62, 63, 64, 65, 66, or 67 wherein a support structure is configured to support a proximal end region of the deformable tip.

69. The ablation catheter of example 54, 55, 56, 57, 58, 59, 60, 61, 62, 63, 64, 65, 66, 67, or 68 wherein the deformable tip has a thickness of 0.20 mm or less.

70. The ablation catheter of example 54, 55, 56, 57, 58, 59, 60, 61, 62, 63, 64, 65, 66, 67, 68, or 69 further comprising a conductive material along an inner surface of the deformable tip.

71. The ablation catheter of example 70 wherein the conductive material is conductive to RF energy.

72. The ablation catheter of example 70 or example 71 wherein the conductive material is a conductive layer.

73. The ablation catheter of example 72 wherein the conductive layer comprises conductive ink.

74. The ablation catheter of example 70, 71, 72, or 73 wherein the conductive material extends along at least a portion of a neck of the deformable tip, and wherein the neck is secured to the catheter body such that the conductive material contacts a conductive element exposed along an outer surface of the catheter body.

75. The ablation catheter of example 70, 71, 72, 73, or 74 wherein the conductive material covers substantially an entire inner surface of the deformable tip.

76. The ablation catheter of example 54, 55, 56, 57, 58, 59, 60, 61, 62, 63, 64, 65, 66, 67, 68, 69, 70, 71, 72, 73, 74, or 75 wherein a body of the deformable tip comprises a conductive material.

77. The ablation catheter of example 54, 55, 56, 57, 58, 59, 60, 61, 62, 63, 64, 65, 66, 67, 68, 69, 70, 71, 72, 73, 74, 75, or 76 further comprising an insulating layer along an outer surface of a/the body of the deformable tip.

78. The ablation catheter of example 54, 55, 56, 57, 58, 59, 60, 61, 62, 63, 64, 65, 66, 67, 68, 69, 70, 71, 72, 73, 74, 75, 76, or 77 wherein a/the body of the deformable tip comprises a polymeric material containing conductive particles.

79. The ablation catheter of example 54, 55, 56, 57, 58, 59, 60, 61, 62, 63, 64, 65, 66, 67, 68, 69, 70, 71, 72, 73, 74, 75, 76, 77, or 78 wherein the ablation catheter is configured to cause liquid to flow from an interior of the deformable tip toward an object that is in contact with and deforming the deformable tip.

80. An ablation catheter comprising:
a catheter body;
a deformable tip secured to the catheter body, wherein an end region of the deformable tip comprises a support structure configured to limit deformation of the end region in response to a proximal or lateral force applied to the deformable tip.

81. The ablation catheter of example 80 wherein the end region of the deformable tip is a proximal end region of the deformable tip.

82. The ablation catheter of example 80 or example 81 wherein the end region of the deformable tip comprises a proximal surface of a body of the deformable tip.

83. The ablation catheter of example 80, 81, or 82 wherein the end region of the deformable tip comprises a neck of the deformable tip.

84. The ablation catheter of example 80, 81, 82, or 83 wherein the support structure includes one or more ribs that extend along the end region of the deformable tip.

85. The ablation catheter of example 80, 81, 82, 83, or 84 wherein the support structure is integral with a wall of the deformable tip.

86. The ablation catheter of example 80, 81, 82, 83, or 84 wherein the support structure is a component that is attached to the deformable tip.

87. The ablation catheter of example 80, 81, 82, 83, 84, 85, or 86 wherein the support structure comprises a plurality of fingers that extend along the end region of the deformable tip.

88. The ablation catheter of example 87 further comprising one or more electrodes attached to one or more fingers of the plurality of fingers.

89. The ablation catheter of example 88 wherein the one of more fingers are flexible printed circuits arranged to carry signals to and from the one or more electrodes.

90. The ablation catheter of example 88 or example 89 wherein the one or more electrodes are flexible printed circuits.

91. The ablation catheter of example 87, 88, 89, or 90 further comprising a patterned layer of stiffening material on the plurality of fingers, wherein the patterned layer comprises multiple discrete segments that increase in width as the multiple discrete segments extend away from the plurality of fingers.

92. The ablation catheter of example 91 wherein the multiple discrete segments are wider along a top edge of the multiple discrete segments than along a bottom edge of the multiple discrete segments.

93. The ablation catheter of example 91 or example 92 wherein the multiple discrete segments are configured to inhibit a radial inward force applied to the end region of the deformable tip from inwardly deflecting the end region of the deformable tip.

94. The ablation catheter of example 80, 81, 82, 83, 84, 85, 86, 87, 88, 89, 90, 91, 92, or 93 wherein the support structure comprises a stiff member that is attached the catheter body and that extends into an interior of the deformable tip, and wherein a plurality of tethers is anchored at one end to the stiff member and at another end to the deformable tip.

95. The ablation catheter of example 80, 81, 82, 83, 84, 85, 86, 87, 88, 89, 90, 91, 92, 93, or 94 wherein the deformable tip is formed of an elastomeric material.

96. The ablation catheter of example 80, 81, 82, 83, 84, 85, 86, 87, 88, 89, 90, 91, 92, 93, 94, or 95 further comprising a conductive member configured to deliver current to liquid within the deformable tip such that liquid passing from an interior of the deformable tip to an exterior of the deformable tip can convey RF energy away from the deformable tip.

97. The ablation catheter of example 80, 81, 82, 83, 84, 85, 86, 87, 88, 89, 90, 91, 92, 93, 94, 95, or 96 wherein the ablation catheter is configured to emit RF energy away from the deformable tip in response to deformation of the deformable tip.

98. The ablation catheter of example 96 or example 97 wherein the RF energy is transmitted from an interior of the deformable tip to an exterior of the deformable tip via liquid exiting the deformable tip.

99. The ablation catheter of example 80, 81, 82, 83, 84, 85, 86, 87, 88, 89, 90, 91, 92, 93, 94, 95, 96, 97, or 98 wherein the deformable tip comprises one or more valves, and wherein the one or more valves are configured to open in response to deformation of the deformable tip.

100. The ablation catheter of example 99 wherein the one or more valves comprise one or more slits extending through a wall of the deformable tip.

101. The ablation catheter of example 99 or example 100 wherein the deformable tip comprises support regions between adjacent valves.

102. The ablation catheter of example 101 wherein the support regions comprise ribs.

103. The ablation catheter of example 102 wherein the ribs are attached at opposite ends to walls of the adjacent valves.

104. The ablation catheter of example 80, 81, 82, 83, 84, 85, 86, 87, 88, 89, 90, 91, 92, 93, 94, 95, 96, 97, 98, 99, 100, 101, 102, or 103 wherein the deformable tip has a thickness of 0.20 mm or less.

105. The ablation catheter of example 80, 81, 82, 83, 84, 85, 86, 87, 88, 89, 90, 91, 92, 93, 94, 95, 96, 97, 98, 99, 100, 101, 102, 103, or 104 further comprising a conductive material on a surface of the deformable tip.

106. The ablation catheter of example 105 wherein the conductive material is conductive to RF energy.

107. The ablation catheter of example 104 or example 105 wherein the conductive material is a conductive layer.

108. The ablation catheter of example 107 wherein the conductive layer comprises conductive ink.

109. The ablation catheter of example 107 or example 108 wherein the conductive layer covers substantially an entire inner surface of the deformable tip.

110. The ablation catheter of example 80, 81, 82, 83, 84, 85, 86, 87, 88, 89, 90, 91, 92, 93, 94, 95, 96, 97, 98, 99, 100, 101, 102, 103, 104, 105, 106, 107, 108, or 109 wherein a body of the deformable tip comprises a conductive material.

111. The ablation catheter of example 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, or 110 further comprising an insulating layer along a surface of a/the body of the deformable tip.

112. The ablation catheter of example 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, or 111 wherein a/the body of the deformable tip comprises a polymeric material containing conductive particles.

113. The ablation catheter of example 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, or 112 wherein the ablation catheter is configured to cause liquid to flow from an interior of the deformable tip toward an object that is in contact with and deforming the deformable tip.

114. A method comprising:
viewing a deformable tip of an ablation catheter via fluoroscopy; and
advancing the ablation catheter toward an object until a deformation of the deformable tip is viewed.

115. The method of example 114 wherein advancing the ablation catheter includes advancing the ablation catheter until a predetermined level of deformation of the deformable tip is viewed.

116. The method of example 115 wherein the predetermined level of deformation of the deformable tip is a deformation that displaces a surface of the deformable tip by ⅓ to ½ of an undeformed diameter of the deformable tip.

117. The method of example 114, 115, or 116 further comprising identifying a contact region between the deformable tip and the object based on the viewing.

118. The method of example 117 wherein the contact region is graphically displayed on a graphical user interface.

119. The method of example 117 or example 118 further comprising increasing an area of contact between the deformable tip and the object by further advancing the ablation catheter.

120. The method of example 114, 115, 16, 117, 118, or 119 wherein the deformation of the deformable tip causes one or more valves of the deformable tip to open such that liquid emits from an interior of the deformable tip to an exterior of the deformable tip.

121. The method of example 114, 115, 116, 117, 118, 119, or 120 further comprising collecting data from one or more sensors of the ablation catheter.

122. The method of example 121 further comprising determining a shape of the deformable tip based on the collected data.

123. The method of example 122 wherein the shape of the deformable tip is graphically displayed on a graphical user interface.

124. The method of example 121, 122, or 123 wherein the one or more sensors are electrodes.

125. The method of example 121, 122, 123, or 124 further comprising determining a temperature of the deformable tip based on the collected data.

126. The method of example 125 wherein the temperature of the deformable tip is graphically displayed on a graphical user interface.

127. The method of example 121, 122, 123, 124, 125, or 126 wherein the one or more sensors are temperature sensors.

128. The method of example 121, 122, 123, 124, 125, 126, or 127 wherein the one or more sensors are secured to the deformable tip.

129. The method of example 114, 115, 116, 117, 118, 119, 120, 121, 122, 123, 124, 125, 126, 127, or 128 wherein the object is tissue, and wherein the method further comprises ablating the tissue.

130. The method of example 129 wherein ablating the tissue comprises delivering RF energy to the tissue.

131. The method of example 130 wherein delivering RF energy to the tissue comprises delivering liquid from an interior of the deformable tip to an exterior of the deformable tip, the liquid serving as a conduit for the RF energy.

132. The method of example 131 wherein the liquid travels from the interior of the deformable tip to the exterior of the deformable tip via valves of the deformable tip that open when a portion of the deformable tip comprising the valves is deformed.

133. An ablation catheter comprising:
a catheter body including a fluid delivery lumen;
a deformable tip secured to the catheter body, the deformable tip including a conductive material; and
one or more electrodes secured to an exterior surface of the deformable tip.

134. The ablation catheter of example 133 wherein the one or more electrodes are secured directly to the exterior surface of the deformable tip.

135. The ablation catheter of example 133 wherein the one or more electrodes are secured to a member that extends along the exterior surface of the deformable tip and that is secured to the exterior surface of the deformable tip.

136. The ablation catheter of example 133, 134, or 135 further comprising one or more temperature sensors in thermal communication with the one or more electrodes, and wherein the one or more temperature sensors are thermally insulated from the conductive material and/or from fluid contained in the deformable tip.

137. The ablation catheter of example 136 wherein the one or more temperature sensors thermally communicate with the one or more electrodes through a nonconductive material.

138. The ablation catheter of example 137 wherein the nonconductive material is a polyamide.

139. The ablation catheter of example 136, 137, or 138 wherein the one or more temperature sensors are thermistors.

140. The ablation catheter of example 133, 134, 135, 136, 137, 138, or 139 wherein the one or more electrodes comprise one or more pairs of concentric electrodes secured to the exterior surface of the deformable tip, and wherein each pair of concentric electrodes comprises a central conductive member and an annular conductive member surrounding the central conductive member.

141. The ablation catheter of example 140 wherein the one or more pairs of concentric electrodes are configured to generate a bipolar signal.

142. The ablation catheter of example 140 or example 141 wherein the one or more pairs of concentric electrodes are configured in a manner such that values resulting from current driven between the central conductive member and the annular conductive member can be used to determine contact between the deformable tip and tissue.

143. The ablation catheter of example 140, 141, or 142 wherein the one or more pairs of concentric electrodes are configured in a manner such that values resulting from voltage driven between the central conductive member and the annular conductive member can be used to determine contact between the deformable tip and tissue.

144. The ablation catheter of example 133, 134, 135, 136, 137, 138, 139, 140, 141, 142, or 143 wherein the ablation catheter is configured to heat liquid that passes through the fluid delivery lumen and into the deformable tip.

145. The ablation catheter of example 133, 134, 135, 136, 137, 138, 139, 140, 141, 142, 143, or 144 wherein the conductive material is a first conductive material, and wherein the first conductive material is secured to an inner surface of a proximal end region of the deformable tip, and further wherein a second conductive material is secured to an inner surface of a distal end region of the deformable tip for heating liquid in the deformable tip.

146. The ablation catheter of example 145 wherein the first conductive material and the second conductive material are electrodes.

147. The ablation catheter of example 146 further comprising one or more wires connected to the electrodes secured to the inner surface of the deformable tip for delivering electrical energy from a generator to the electrodes secured to the inner surface of the deformable tip.

148. The ablation catheter of example 133, 134, 135, 136, 137, 138, 139, 140, 141, 142, 143, 144, 145, 146, or 147 comprising a heating element positioned along the fluid delivery lumen of the catheter body.

149. The ablation catheter of example 148 wherein the heating element comprises a tubular electrode positioned along the catheter body, and wherein the tubular electrode defines a portion of the fluid delivery lumen and is configured to heat liquid that passes through the fluid delivery lumen.

150. The ablation catheter of example 133, 134, 135, 136, 137, 138, 139, 140, 141, 142, 143, 144, 145, 146, 147, 148, or 149 comprising a rod-shaped electrode that extends distally from a distal end of the catheter body and into an interior of the deformable tip, and wherein the rod-shaped electrode is configured to heat liquid that passes through the fluid delivery lumen and into the interior of the deformable tip.

151. The catheter of example 133, 134, 135, 136, 137, 138, 139, 140, 141, 142, 143, 144, 145, 146, 147, 148, 149, or 150 wherein the deformable tip is formed of an elastomeric material.

152. The catheter of example 133, 134, 135, 136, 137, 138, 139, 140, 141, 142, 143, 144, 145, 146, 147, 148, 149, 150, or 151 wherein the conductive material is configured to deliver current to liquid within the deformable tip such that liquid passing from an interior of the deformable tip to an exterior of the deformable tip can convey RF energy away from the deformable tip.

153. The catheter of example 133, 134, 135, 136, 137, 138, 139, 140, 141, 142, 143, 144, 145, 146, 147, 148, 149, 150, 151, or 152 wherein the ablation catheter is configured to emit RF energy away from the deformable tip in response to deformation of the deformable tip.

154. The catheter of example 152 or example 153 wherein the RF energy is transmitted from an interior of the deformable tip to an exterior of the deformable tip via liquid exiting the deformable tip.

155. The catheter of example 133, 134, 135, 136, 137, 138, 139, 140, 141, 142, 143, 144, 145, 146, 147, 148, 149, 150, 151, 152, 153, or 154 wherein the deformable tip has a thickness of 0.20 mm or less.

156. The catheter of example 133, 134, 135, 136, 137, 138, 139, 140, 141, 142, 143, 144, 145, 146, 147, 148, 149, 150, 151, 152, 153, 154, or 155 wherein the conductive material is positioned along a surface of the deformable tip.

157. The catheter of example 133, 134, 135, 136, 137, 138, 139, 140, 141, 142, 143, 144, 145, 146, 147, 148, 149, 150, 151, 152, 153, 154, 155, or 156 wherein the conductive material is conductive to RF energy.

158. The catheter of example 133, 134, 135, 136, 137, 138, 139, 140, 141, 142, 143, 144, 145, 146, 147, 148, 149, 150, 151, 152, 153, 154, 155, 156, or 157 wherein the conductive material is a conductive layer.

159. The catheter of example 158 wherein the conductive layer comprises conductive ink.

160. The catheter of example 158 or example 159 wherein the conductive layer covers substantially an entire inner surface of the deformable tip.

161. The catheter of example 133, 134, 135, 136, 137, 138, 139, 140, 141, 142, 143, 144, 145, 146, 147, 148, 149, 150, 151, 152, 153, 154, 155, 156, 157, 158, 159, or 160 wherein a body of the deformable tip comprises the conductive material.

162. The catheter of example 133, 134, 135, 136, 137, 138, 139, 140, 141, 142, 143, 144, 145, 146, 147, 148, 149, 150, 151, 152, 153, 154, 155, 156, 157, 158, 159, 160 or 161 further comprising an insulating layer along a surface of a/the body of the deformable tip.

163. The catheter of example 133, 134, 135, 136, 137, 138, 139, 140, 141, 142, 143, 144, 145, 146, 147, 148, 149, 150, 151, 152, 153, 154, 155, 156, 157, 158, 159, 160, 161, or 162 wherein a/the body of the deformable tip comprises a polymeric material containing conductive particles.

164. The catheter of example 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, or 163 wherein the ablation catheter is configured to cause liquid to flow from an interior of the deformable tip toward an object that is in contact with and deforming the deformable tip.

165. A tissue ablation method, comprising:
delivering energy to tissue during a first phase, wherein an energy generator used to generate the delivered energy is set to a first power setting during the first phase;
delivering energy to the tissue during a second phase, wherein the energy generator used to generate the delivered energy is set to a second power setting during the second phase, and wherein the second power setting is different than the first power setting such that a penetration depth of the delivered energy into the tissue during the second phase differs from a penetration depth of the delivered energy into the tissue during the first phase.

166. The tissue ablation method of example 165 wherein the second power setting is higher than the first power setting such that the penetration depth of the delivered energy into the tissue during the second phase is greater than the penetration depth of the delivered energy into the tissue during the first phase.

167. The tissue ablation method of example 165 or example 166 further comprising delivering a cooling fluid to the tissue at a first flow rate during the first phase.

168. The tissue ablation method of example 167 further comprising delivering the cooling fluid to the tissue at a second flow rate during the second phase, wherein the second flow rate is different than from the first flow rate.

169. The tissue ablation method of example 165, 166, 167, or 168 further comprising delivering energy to the tissue during a third phase, wherein the energy generator used to generate the delivered energy is set to a third power setting during the third phase, and wherein the third power setting is different than the first and the second power settings.

170. The tissue ablation method of example 169 further comprising delivering the cooling fluid to the tissue at a third flow rate during the third phase, wherein the third flow rate is different than the first and the second flow rates.

171. The tissue ablation method of example 170 wherein the third flow rate is lower than the first and the second flow rates.

172. The method of example 165, 166, 167, 168, 169, 170, or 171 wherein the energy delivered to the tissue ablates the tissue.

173. The method of example 165, 166, 167, 168, 169, 170, 171, or 172 wherein the energy delivered to the tissue is RF energy.

174. The method of example 173 wherein the RF energy is delivered to the tissue by delivering liquid from an interior of a deformable tip of an ablation catheter to an exterior of the deformable tip of the ablation catheter, the liquid serving as a conduit for the RF energy.

175. The method of example 174 wherein the liquid travels from the interior of the deformable tip to the exterior of the deformable tip via valves of the deformable tip that open when a portion of the deformable tip comprising the valves is deformed.

176. The method of example 165, 166, 167, 168, 169, 170, 171, 172, 173, or 174 further comprising collecting data from one or more sensors of the ablation catheter.

177. The method of example 176 further comprising determining a shape of the deformable tip based on the collected data.

178. The method of example 177 further comprising graphically displaying the shape of the deformable tip on a graphical user interface.

179. The method of example 176, 177, or 178 further comprising determining a contact region between the deformable tip and the tissue based on the collected data.

180. The method of example 179 further comprising graphically displaying the contact region on a graphical user interface.

181. The method of example 176, 177, 178, 179, or 180 wherein the one or more sensors are electrodes.

182. The method of example 176, 177, 178, 179, 180, or 181 further comprising determining a temperature of the deformable tip based on the collected data.

183. The method of example 182 further comprising graphically displaying the temperature of the deformable tip on a graphical user interface.

184. The method of example 176, 177, 178, 179, 180, 181, 182, or 183 wherein the one or more sensors are temperature sensors.

185. The method of example 176, 177, 178, 179, 180, 181, 182, 183, or 184 wherein the one or more sensors are secured to the deformable tip.

186. An ablation catheter comprising:
a catheter body;
a deformable tip secured to the catheter body,
wherein the ablation catheter is configured to emit RF energy in a direction 330° or less about the deformable tip.

187. An ablation catheter comprising:
a catheter body;
a deformable tip secured to the catheter body wherein, the deformable tip includes one or more valves, and wherein the deformable tip is configured such that valves in no more than 90 percent of a surface area of the deformable tip open when the deformable tip is deformed by tissue.

188. An ablation catheter comprising:
a catheter body;
a deformable tip secured to the catheter body, wherein the deformable tip comprises one or more valves, and wherein the deformable tip comprises at least one support region associated with each of the one or more valves.

189. The catheter of example 188 wherein the support regions are located between adjacent valves.

190. The catheter of example 188 or example 189 wherein the support regions comprise ribs.

191. The catheter of example 190 wherein the ribs are attached at opposite ends to walls of adjacent valves.

192. A method comprising:
measuring a first value or set of values resulting from an electrical current driven between two or more electrodes secured to a deformable tip of a catheter,
measuring a second value or set of values resulting from an electrical current driven between the two or more electrodes secured to the deformable tip of the catheter, and
determining a state of one or more valves of the deformable tip based on a comparison between the first and second values or the first and second sets of values.

193. The method of example 192 wherein determining the state of the one or more valves comprises determining whether the one or more valves are open or closed.

194. The method of example 192 or example 193 wherein determining the state of the one or more valves comprises determining the state of at least one valve in a first region of the deformable tip and determining the state of at least one valve in a second region of the deformable tip.

195. The method of example 194 wherein determining the state of the valves in the first and second regions of the deformable tip comprises determining whether the valves in the first and second regions of the deformable tip are open or closed.

196. The method of example 192, 193, 194, or 195 wherein at least one of the two or more electrodes is within the deformable tip.

197. The method of example 192, 193, 194, 195, or 196 wherein at least one of the two or more electrodes is outside of the deformable tip.

198. The method of example 192, 193, 194, 195, 196, or 197 wherein the electrical current is driven between at least one electrode within the deformable tip and an electrode outside of the deformable tip.

199. The method of example 192, 193, 194, 195, 196, 197, or 198 wherein a location of an opened valve in the one or more valves corresponds to a geometrical configuration of the deformable tip.

200. The method of example 199 further comprising generating a visual representation of the geometrical configuration of the deformable tip.

201. The method of example 192, 193, 194, 195, 196, 197, 198, 199, or 200 wherein at least one of the two or more electrodes is a concentric electrode that includes a central conductive member and an annular conductive member surrounding the central conductive member.

202. The method of example 192, 193, 194, 195, 196, 197, 198, 199, 200, or 201 further comprising generating a visual representation of a location of an opened valve in one or more valves.

203. The method of example 192, 193, 194, 195, 196, 197, 198, 199, 200, 201, or 202 wherein the first value or set of values is associated with the deformable tip in a known state, and wherein the second value or set of values is associated with the deformable tip in an unknown state.

204. The method of example 203 wherein the known state is a state in which all valves of the deformable tip are closed.

D. Conclusion

The above detailed descriptions of implementations of the technology are not intended to be exhaustive or to limit the technology to the precise form disclosed above. Although specific implementations of, and examples for, the technology are described above for illustrative purposes, various equivalent modifications are possible within the scope of the technology, as those skilled in the relevant art will recognize. For example, while steps are presented in a given order, alternative implementations can perform steps in a different order. Furthermore, the various implementations described herein can also be combined to provide further implementations.

From the foregoing, it will be appreciated that specific implementations of the technology have been described herein for purposes of illustration, but well-known structures and functions have not been shown or described in detail to avoid unnecessarily obscuring the description of the implementations of the technology. Where the context permits, singular or plural terms can also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms can also include the plural or singular term, respectively. Additionally, the terms "comprising," "including," "having" and "with" are used throughout to mean including at least the recited feature(s) such that any greater number of the same feature and/or additional types of other features are not precluded. To the extent any materials incorporated herein by reference conflict with the present disclosure, the present disclosure controls.

From the foregoing, it will also be appreciated that various modifications can be made without deviating from the technology. For example, various components of the technology can be further divided into subcomponents, or that various components and functions of the technology can be combined and/or integrated. Furthermore, although advantages associated with certain implementations of the technology have been described in the context of those implementations, other implementations can also exhibit such advantages, and not all implementations need necessarily exhibit such advantages to fall within the scope of the technology.

The invention claimed is:

1. An ablation catheter comprising:
a catheter body having an outer diameter and defining a fluid delivery lumen, and
a deformable tip secured to the catheter body,
wherein the deformable tip (i) comprises one or more valves that are configured to open in response to inward deformation of the deformable tip upon contact with target tissue and (ii) has an inner diameter greater than the outer diameter of the catheter body, and
wherein the ablation catheter is configured to permit liquid communication between an interior of the deformable tip and an exterior of the deformable tip in response to a deformation of the tip.

2. The catheter of claim 1 wherein the deformable tip is formed of an elastomeric material.

3. The catheter of claim 1 further comprising a conductive member configured to deliver current to liquid within the deformable tip such that liquid passing from the interior of the deformable tip to the exterior of the deformable tip can convey RF energy away from the deformable tip.

4. The catheter of claim 1 wherein the ablation catheter is configured to emit RF energy away from the deformable tip in response to the deformation of the deformable tip.

5. The catheter of claim 4 wherein the RF energy is transmitted from the interior of the deformable tip to the exterior of the deformable tip via liquid exiting the deformable tip.

6. The catheter of claim 1 wherein the one or more valves comprise one or more slits extending through a wall of the deformable tip.

7. The catheter of claim 6 wherein the one or more valves comprise 3-legged slits extending through the wall of the deformable tip.

8. The catheter of claim 6 wherein the one or more slits extend through a recessed region of the wall of the deformable tip.

9. The catheter of claim 8 wherein the recessed region of the wall of the deformable tip is tetrahedral-shaped.

10. The catheter of claim 8 wherein the recessed region of the wall of the deformable tip is hemispherical.

11. The catheter of claim 1 wherein the deformable tip comprises support regions between adjacent valves.

12. The catheter of claim 11 wherein the support regions comprise ribs.

13. The catheter of claim 12 wherein the ribs are attached at opposite ends to walls of adjacent valves.

14. The catheter of claim 1 wherein a support structure is configured to support a proximal end region of the deformable tip.

15. The catheter of claim 14 wherein the support structure includes one or more ribs that extend along the proximal end region of the deformable tip.

16. The catheter of claim 14 wherein the support structure is integral with a wall of the deformable tip.

17. The catheter of claim 14 wherein the support structure is a component that is attached to the deformable tip.

18. The catheter of claim 14 wherein the support structure comprises a plurality of fingers that extend along the proximal end region of the deformable tip.

19. The catheter of claim 18 further comprising one or more electrodes attached to one or more of the fingers.

20. The catheter of claim 19 wherein the fingers are flexible printed circuits arranged to transmit signals to and from the one or more electrodes.

21. The ablation catheter of claim 1 wherein the interior of the deformable tip is configured to receive fluid from the fluid delivery lumen.

22. An ablation catheter, comprising:
a catheter body having an outer diameter;
a deformable tip carried by a distal end portion of the catheter body, wherein the deformable tip has an inner diameter greater than the outer diameter of the catheter body; and
a shape-activated valve in a region of the deformable tip, wherein the shape-activated valve is configured to open in response to inward deformation of the deformable tip resulting from contact between the region and target tissue to permit liquid communication between an interior of the deformable tip and an exterior of the deformable tip.

* * * * *